(12) United States Patent
Peretz et al.

(10) Patent No.: US 11,427,531 B2
(45) Date of Patent: Aug. 30, 2022

(54) MODULATORS OF POTASSIUM ION AND TRPV1 CHANNELS AND USES THEREOF

(71) Applicant: Ramot at Tel-Aviv University Ltd., Tel-Aviv (IL)

(72) Inventors: Asher Peretz, Tel-Aviv (IL); Bernard Attali, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/754,386

(22) PCT Filed: Oct. 9, 2018

(86) PCT No.: PCT/IL2018/051094
§ 371 (c)(1),
(2) Date: Apr. 8, 2020

(87) PCT Pub. No.: WO2019/073471
PCT Pub. Date: Apr. 18, 2019

(65) Prior Publication Data
US 2020/0308102 A1    Oct. 1, 2020

Related U.S. Application Data

(60) Provisional application No. 62/569,631, filed on Oct. 9, 2017.

(51) Int. Cl.
*C07C 233/22* (2006.01)
*C07C 237/20* (2006.01)
*A61K 31/165* (2006.01)
*A61P 25/02* (2006.01)
*A61P 43/00* (2006.01)

(52) U.S. Cl.
CPC .......... *C07C 233/22* (2013.01); *A61K 31/165* (2013.01); *A61P 25/02* (2018.01); *C07C 237/20* (2013.01); *A61P 43/00* (2018.01)

(58) Field of Classification Search
None
See application file for complete search history.

(56) References Cited

U.S. PATENT DOCUMENTS

| | | | |
|---|---|---|---|
| 3,938,995 A * | 2/1976 | Gompf | G03C 7/26 430/367 |
| 6,291,442 B1 | 9/2001 | Yellen | |
| 6,593,349 B2 | 7/2003 | Mcnaughton-Smith et al. | |
| 9,464,052 B2 * | 10/2016 | Edwards | A61P 21/00 |

(Continued)

FOREIGN PATENT DOCUMENTS

| WO | WO 2004/035037 | 4/2004 |
|---|---|---|
| WO | WO 2009/037707 | 3/2009 |

(Continued)

OTHER PUBLICATIONS https://en.wikipedia.org/wiki/Arene_substitution_pattern, downloaded on Apr. 22, 2021 (Year: 2021).*

(Continued)

*Primary Examiner* — Amy C Bonaparte

(57) ABSTRACT

Novel compounds usable in modulating an activity or function of a voltage-dependent potassium channel and/or of TRPV1 are provided. The compounds are represented by Formula I as described and defined in the specification.

23 Claims, 36 Drawing Sheets

(56) References Cited

U.S. PATENT DOCUMENTS

| | | | |
|---|---|---|---|
| 9,675,567 B2* | 6/2017 | Edwards | A61K 31/445 |
| 2003/0055095 A1 | 3/2003 | Baragi et al. | |
| 2005/0250833 A1 | 11/2005 | Attali et al. | |
| 2011/0245250 A1* | 10/2011 | Edwards | A61K 31/5375 |
| | | | 514/237.8 |

FOREIGN PATENT DOCUMENTS

| | | |
|---|---|---|
| WO | WO 2009/071947 | 6/2009 |
| WO | WO 2010/010380 | 1/2010 |
| WO | WO 2019/073471 | 4/2019 |

OTHER PUBLICATIONS

Gonzalez ("K+ Channels: Function-Structural Overview" Comprehensive Physiology, 2012, p. 2087-2149) (Year: 2012).*
Bachmann ("Voltage-Gated Potassium Channels as Regulators of Cell Death" Frontiers in Cell and Developmental Biology, 2020, p. 1-17) (Year: 2020).*
Ambrosino ("Activation of Kv7 Potassium Channels Inhibits Intracellular Ca2+ Increases Triggered by TRPV1-Mediated Pain-Inducing Stimuli in F11 Immortalized Sensory Neurons" Int. J. Mol. Sci. 2019, 20, p. 4322) (Year: 2019).*
"Q3C—Tables and List Guidance for Industry", distributed by the FDA in Jun. 2017, downloaded from https://www.fda.gov/media/71737/download on Dec. 20, 2021. (Year: 2017).*
International Search Report and the Written Opinion dated Dec. 19, 2018 From the International Searching Authority Re. Application No. PCT/IL2018/051094. (14 Pages).

* cited by examiner

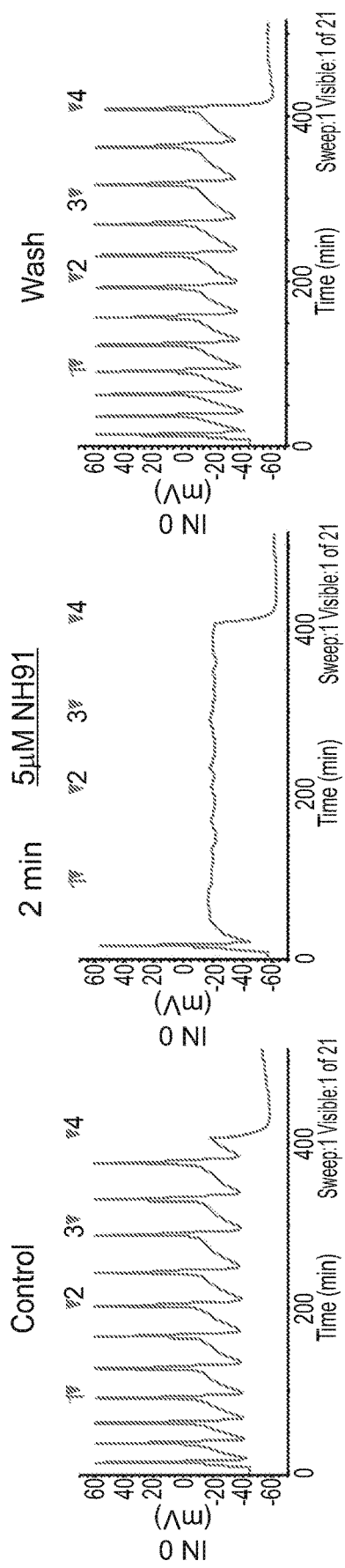
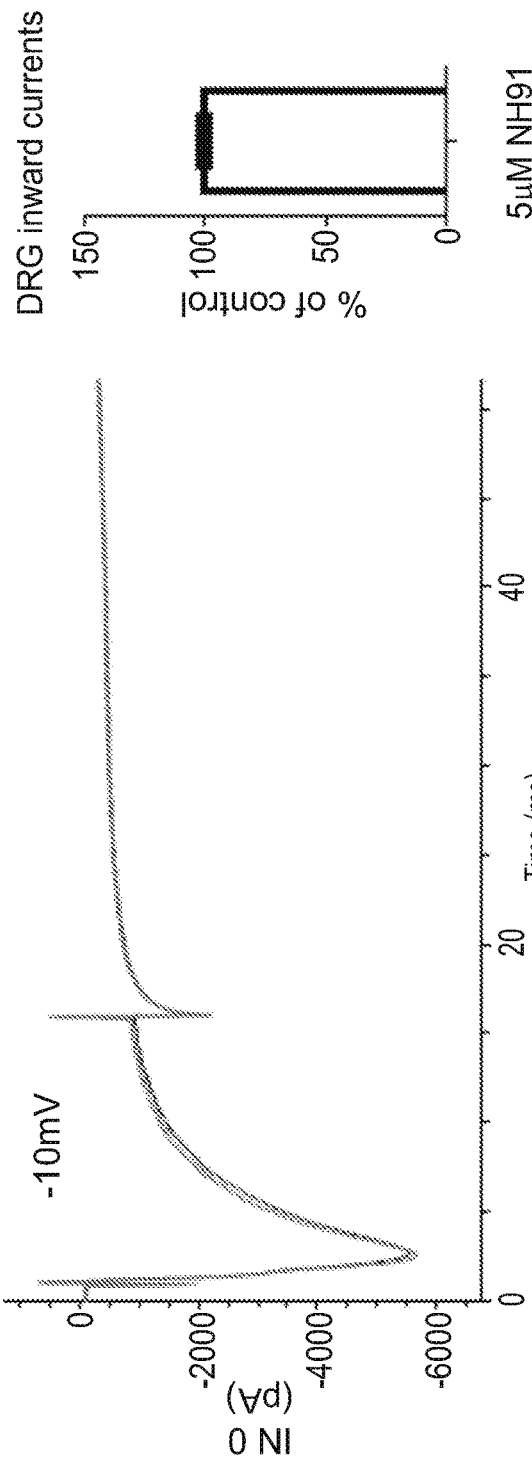
FIG. 15A
FIG. 15B
FIG. 15C

MW: 439.4
logP: 5.148
TPSA: 61.36

MW: 404.9
logP: 4.521
TPSA: 61.36

MW: 4222.9
logP: 4.612
TPSA: 61.36

MW: 422.9
logP: 4.612
TPSA: 61.36

MW: 399.3
logP: 4.387
TPSA: 61.36

MW: 404.9
logP: 4.67
TPSA: 61.36

| Compound | Chemical Structure | Molecular Weight |
|---|---|---|
| NH55 | 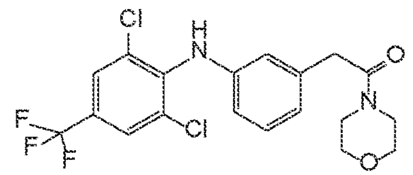 | 432.1 |
| NH56 | 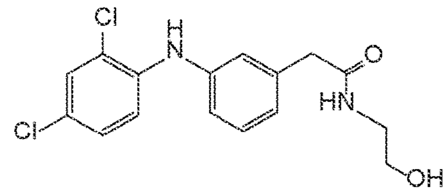 | 338.1 |
| NH57 | 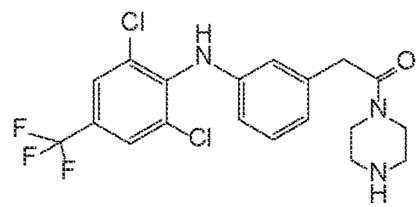 | 431.1 |
| NH58 | 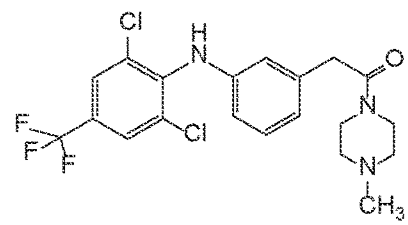 | 445.1 |
| NH59 | 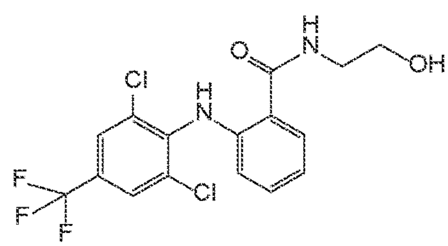 | 392 |
| NH60 | 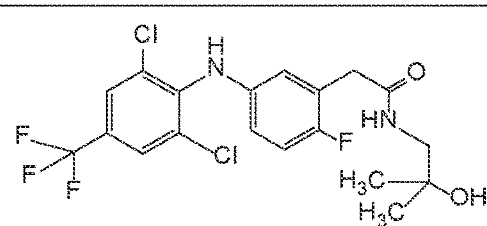 | 434.1 |

FIG. 20 - Continued - 1
| Compound | Chemical Structure | Molecular Weight |
|---|---|---|
| NH61 | 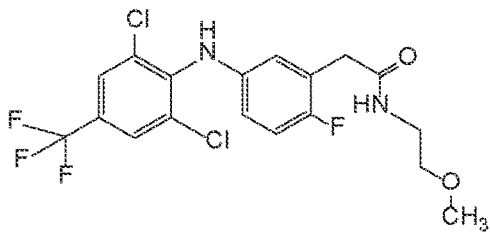 | 438.1 |
| NH62 | 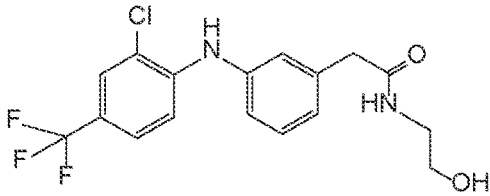 | 372.1 |
| NH63 | 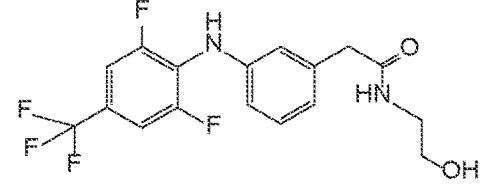 | 374.1 |
| NH64 | 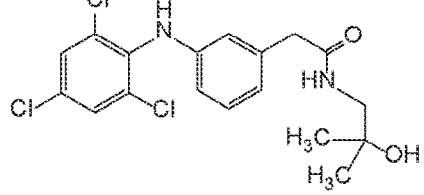 | 400.1 |
| NH65 | 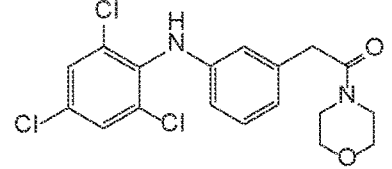 | 398 |
| NH66 | 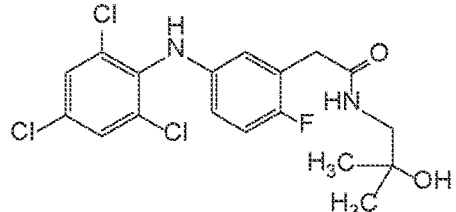 | 418 |

FIG. 20 - Continued - 2

| Compound | Chemical Structure | Molecular Weight |
|---|---|---|
| NH67 | 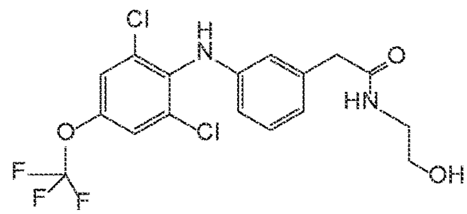 | 422 |
| NH68 | 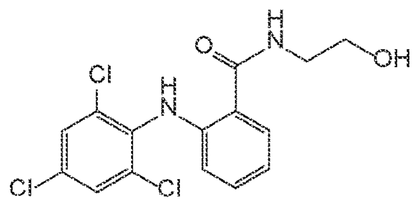 | 358 |
| NH69 | 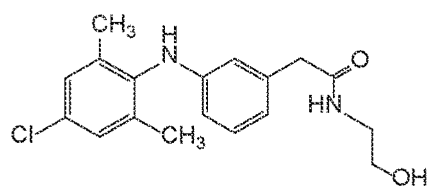 | 332.1 |
| NH70 | 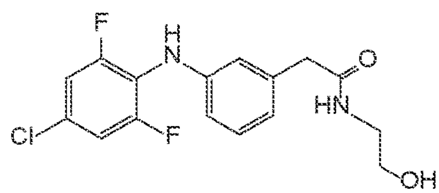 | 340.1 |
| NH71 | 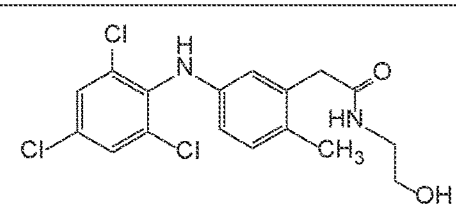 | 386.0 |
| NH72 | 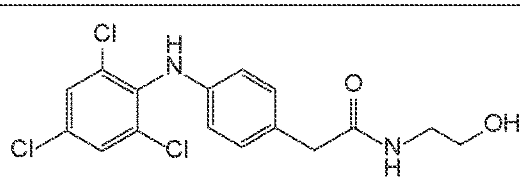 | 372.0 |

FIG. 20 - Continued - 3
| Compound | Chemical Structure | Molecular Weight |
|---|---|---|
| NH73 | 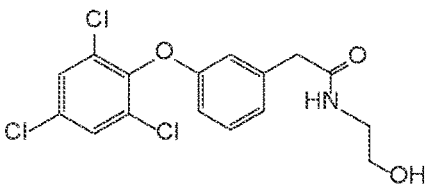 | 373.0 |
| NH74 | 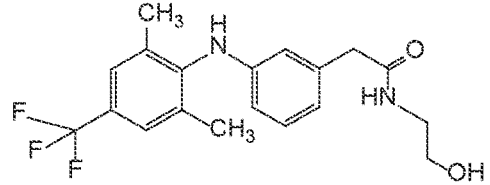 | 366.2 |
| NH75 | 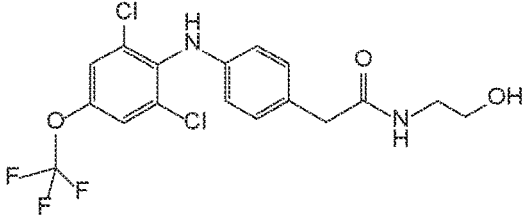 | 422.0 |
| NH76 | 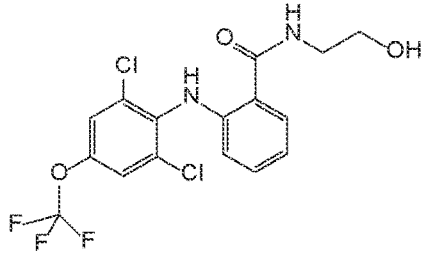 | 408.0 |
| NH77 | 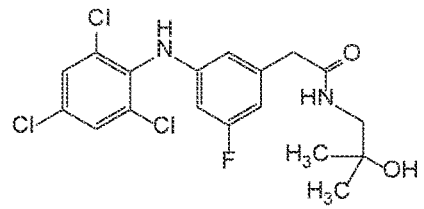 | 390.0 |
| NH78 | 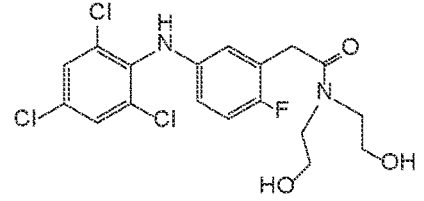 | 434.0 |

FIG. 20 - Continued - 4

| Compound | Chemical Structure | Molecular Weight |
|---|---|---|
| NH79 | 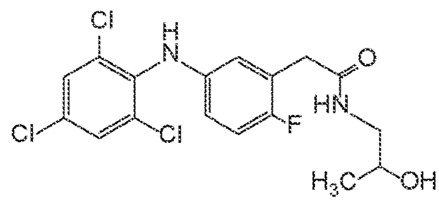 | 404.0 |
| NH80 | 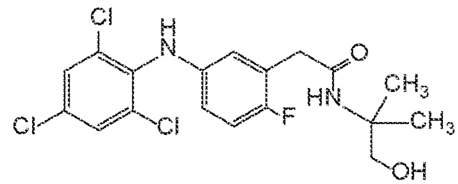 | 418.0 |
| NH81 | 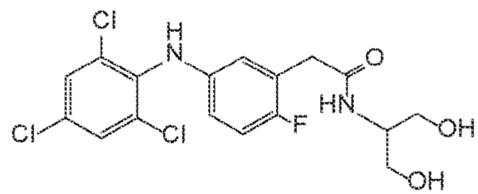 | 420.0 |
| NH82 | 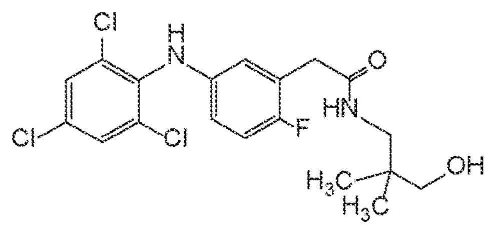 | 432.1 |
| NH83 | 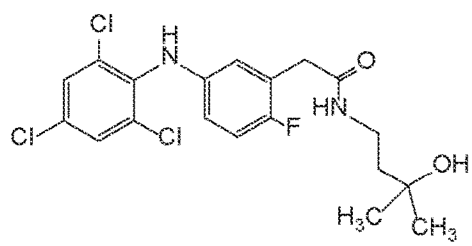 | 432.1 |
| NH84 | 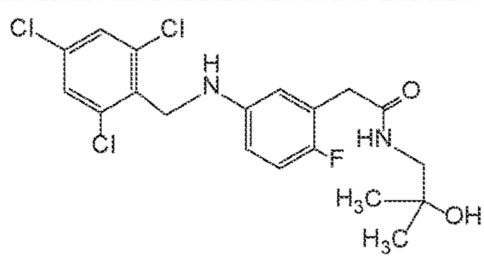 | 432.1 |

FIG. 20 - Continued - 5
| Compound | Chemical Structure | Molecular Weight |
|---|---|---|
| NH85 | 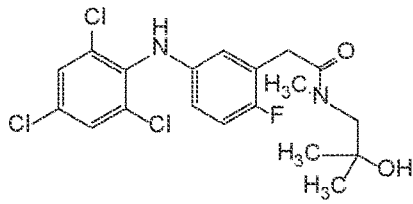 | 432.1 |
| NH86 | 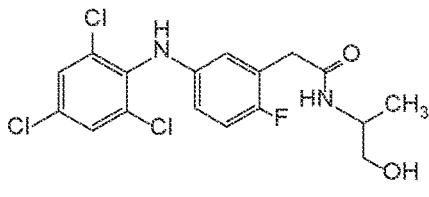 | 404.0 |
| NH87 | 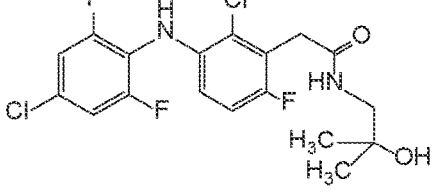 | 420.1 |
| NH88 | 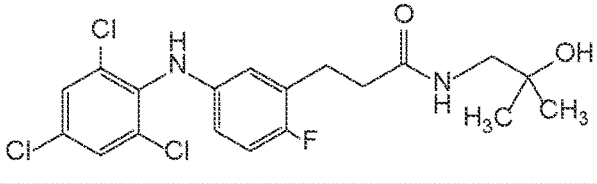 | 432.1 |
| NH89 | 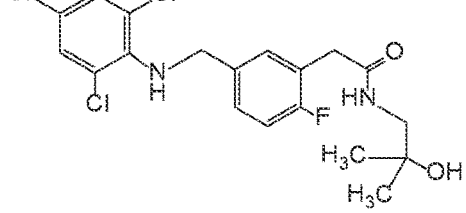 | 432.1 |
| NH90 | 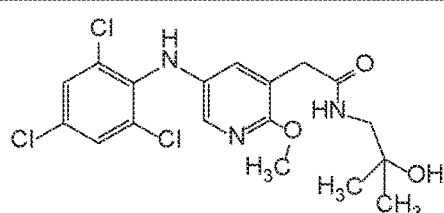 | 431.1 |

FIG. 20 - Continued - 6
| Compound | Chemical Structure | Molecular Weight |
|---|---|---|
| NH91 | 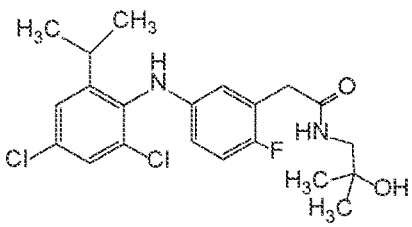 | 426.1 |
| NH92 | 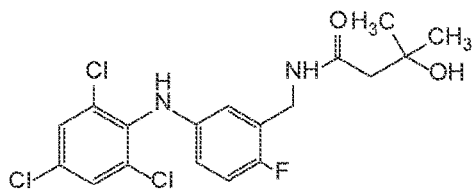 | 418.0 |
| NH93 | 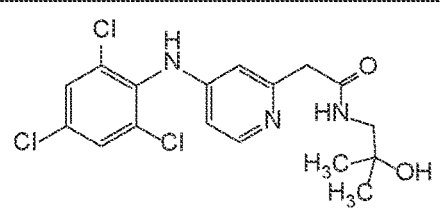 | 401.0 |
| NH101 | 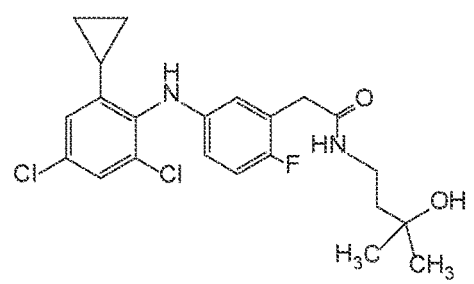 | 439.35 |
| NH103 | 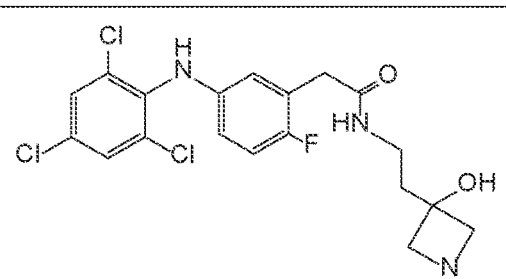 | 446.73 |

FIG. 20 - Continued - 7
| Compound | Chemical Structure | Molecular Weight |
|---|---|---|
| NH108 | 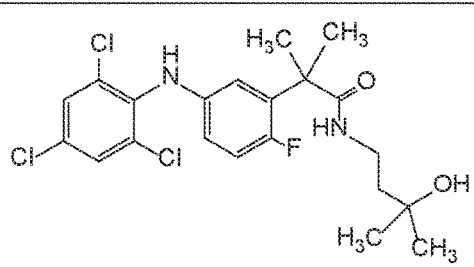 | 461.78 |
| NH109 | 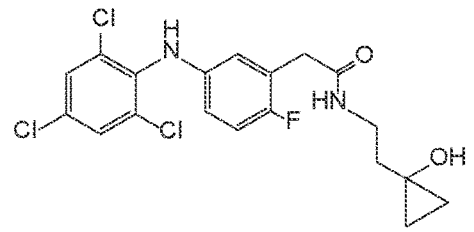 | 431.72 |
| NH110 | 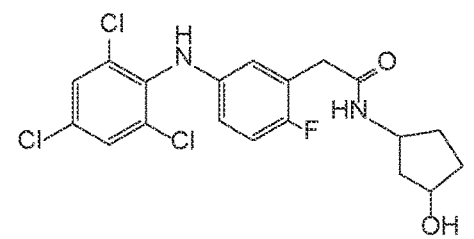 | 431.72 |
| NH112 | 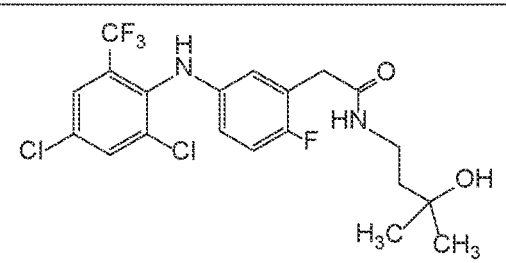 | 467.28 |

MODULATORS OF POTASSIUM ION AND TRPV1 CHANNELS AND USES THEREOF

RELATED APPLICATIONS

This application is a National Phase of PCT Patent Application No. PCT/IL2018/051094 having International filing date of Oct. 9, 2018, which claims the benefit of priority under 35 USC § 119(e) of U.S. Provisional Patent Application No. 62/569,631 filed on Oct. 9, 2017. The contents of the above applications are all incorporated by reference as if fully set forth herein in their entirety.

FIELD AND BACKGROUND OF THE INVENTION

The present invention, in some embodiments thereof, relates to novel derivatives of diphenylamine and, more particularly, but not exclusively, to diphenylamine derivatives featuring a dual activity as modulators of both potassium ion and TRPV1 channels, which are usable in the treatment of various pathologies that are related to these channels, such as neuropathic pain.

Voltage-dependent potassium (Kv) channels conduct potassium ions ($K^+$) across cell membranes in response to change in the membrane voltage and thereby can regulate cellular excitability by modulating (increasing or decreasing) the electrical activity of the cell.

Functional Kv channels exist as multimeric structures formed by the association of four alpha and four beta subunits. The alpha subunits comprise six transmembrane domains, a pore-forming loop and a voltage-sensor and are arranged symmetrically around a central pore. The beta or auxiliary subunits interact with the alpha subunits and can modify the properties of the channel complex to include, but not be limited to, alterations in the channel's electrophysiological or biophysical properties, expression levels or expression patterns.

Functional Kv channels can exist as multimeric structures formed by the association of either identical or dissimilar Kv alpha and/or Kv beta subunits.

Nine Kv channel alpha subunit families have been identified and are termed Kv1-Kv9. As such, there is an enormous diversity in Kv channel function that arises as a consequence of the multiplicity of sub-families, the formation of both homomeric and heteromeric subunits within sub-families and the additional effects of association with beta subunits [M. J. Christie, Clinical and Experimental Pharmacology and Physiology, 1995, 22 (12), 944-951].

The Kv7 channel family consists of at least five members which include one or more of the following mammalian channels: Kv7.1, Kv7.2, Kv7.3, Kv7.4, Kv7.5 and any mammalian or non-mammalian equivalent or variant (including splice variants) thereof. Alternatively, the members of this family are termed KCNQ1, KCNQ2, KCNQ3, KCNQ4 and KCNQ5 respectively [Dalby-Brown et al., Current Topics in Medicinal Chemistry, 2006, 6, 999-1023].

The five members of this family differ in their expression patterns. The expression of Kv7.1 is restricted to the heart, peripheral epithelial and smooth muscle, whereas the expression of Kv7.2-Kv7.4 is limited to the nervous system to include the hippocampus, cortical neurons and dorsal root ganglion neurons [for a review see, for example, Delmas. P & Brown. D, Nature, 2005, 6, 850-862].

The neuronal Kv7 channels have been demonstrated to play key roles in controlling neuronal excitation. Kv7 channels, in particular Kv7.2/Kv7.3 heterodimers, underlie the M-current, a non-activating potassium current found in a number of neuronal cell types. The current has a characteristic time and voltage dependence that results in stabilization of the membrane potential in response to multiple excitatory stimuli. In this way, the M-current is central to controlling neuronal excitability [for a review, see, for example, Delmas. P & Brown. D, Nature, 2005, 6, 850-862].

Potassium channels have been associated with a number of physiological processes, including regulation of heartbeat, dilation of arteries, release of insulin, excitability of nerve cells, and regulation of renal electrolyte transport. Modulators of potassium channels are therefore prime pharmaceutical candidates, and the development of new modulators as therapeutic agents is an on-going research effort.

Thus, given the key physiological role of Kv7 channels in the nervous system and the involvement of these channels in a number of diseases, the development of modulators of Kv7 channels is very desirable.

Potassium channels modulators are divided to channel-openers and channel-blockers. A potassium channel opener that has gained much attention is retigabine (N-(2-amino-4-(4-fluorobenzylamino)-phenyl)carbamic acid ethyl ester). Retigabine is highly selective for KCNQ-type potassium channels consisting of the subunits Kv7.2 and Kv7.3, which was first described in 1993 in EP0554543. Use of retigabine for treating neuropathic pain was disclosed in, for example, U.S. Pat. No. 6,117,900 and EP1223927. Compounds related to retigabine have also been proposed for use as potassium channel modulators, see, for example, U.S. Pat. No. 6,472,165.

However, retigabine has been reported to have multiple effects in neuronal cells. These include sodium and calcium channel blocking activity (Rundfeldt, C, 1995, Naunyn-Schmiederberg's Arch Pharmacol, 351 (Suppl): R160) and effects on GABA (γ-aminobutyric acid) synthesis and transmission in rat neurons (Kapetanovic, I. M., 1995, Epilepsy Research, 22, 167-173, Rundfeldt, C, 1995, Naunyn-Schmiederberg's Arch Pharmacol, 351 (Suppl):R160).

Other KCNQ potassium channel modulators have been described in, for example, U.S. patent application Ser. No. 10/075,521, which teaches 2,4-disubstituted pyrimidine-5-carboxamide derivatives as Kv7 modulator; U.S. patent application Ser. No. 10/160,582, which teaches cinnamide derivatives as voltage-dependent potassium channel modulators; U.S. Pat. No. 5,565,483 and U.S. patent application Ser. Nos. 10/312,123, 10/075,703 and 10/075,522, which teach 3-substituted oxindole derivatives as voltage-dependent potassium channel modulators; U.S. Pat. No. 5,384,330, which teaches 1,2,4-triamino-benzene derivatives as potassium channel modulators; and U.S. Pat. No. 6,593,349 which teaches bisarylamines derivatives as voltage-dependent potassium channel modulators. U.S. Pat. No. 6,291,442 teaches compounds comprising two or three aromatic rings having a free carboxyl or a carboxyl being linked, via an ester bond, to a lower alkyl ester, attached to one of the rings, for the modulation of Shaker class of voltage gated potassium channels.

WO2004/035037 and U.S. Patent Application Publication No. 20050250833 teach derivatives of N-phenylanthranilic acid and 2-benzimidazolone as potassium channel openers, especially voltage-dependent potassium channels such as Kv7.2 1, Kv7.3 and KCv7.2/7.3 channels, as well as neuron activity modulators.

WO 2009/037707 teaches additional derivatives of N-phenylanthranilic as potassium channel and/or TRPV1 modulators. An exemplary modulator disclosed in WO 2009/037707 is referred to as NH29:

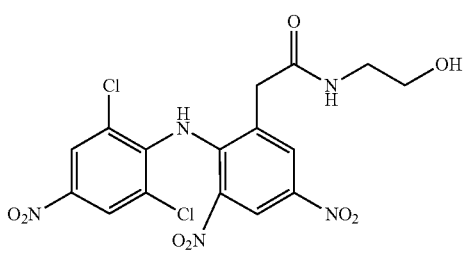

NH29

WO 2009/071947 and WO 2010/010380 teach derivatives of diphenylamine as potassium channel modulators. Exemplary modulators disclosed in WO 2009/037707 is referred to as NH34 and NH43:

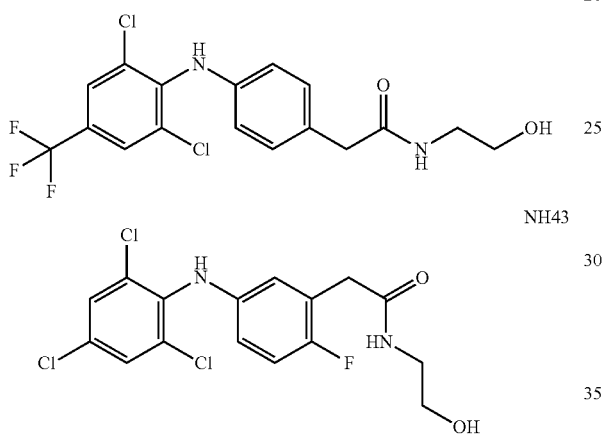

Transient receptor potential vanilloid type 1 (TRPV1) receptor is a ligand-gated non-selective cation channel activated by heat (typically above 43° C.), low pH (<6) and endogenous lipid molecules such as anandamide, N-arachidonoyl-dopamine, N-acyl-dopamines and products of lipoxygenases (e.g., 12- and 15-(S)-HPETE) termed endovanilloids. Apart from peripheral primary afferent neurons and dorsal root ganglia, TRPV1 receptor is expressed throughout the brain. Recent evidence shows that TRPV1 receptor stimulation by endocannabinoids or by capsaicin leads to analgesia and this effect is associated with glutamate increase and the activation of OFF cell population in the rostral ventromedial medulla (RVM).

TRPV1 has also been found to be involved in the regulation of body temperature, anxiety and mediation of long-term depression (LTD) in the hippocampus. TRPV1 channels are also located on sensory afferents, which innervate the bladder. Inhibition of TRPV1 has been shown to ameliorate urinary incontinence symptoms.

TRPV1 modulators have been described in, for example, WO 2007/054480, which teaches the effect of 2-(benzimidazol-1-yl)-acetamide derivatives in the treatment of TRPV1 related diseases. WO 2008/079683 teaches compounds being a conjugated two-ring system of cyclohexyl and phenyl for inhibiting TRPV1 receptor. EP01939173 teaches O-substituted-dibenzyl urea- or thiourea-derivatives as TRPV1 receptor antagonists. WO 2008/076752 teaches benzoimidazole compounds as potent TRPV1 modulators and EP01908753 teaches TRPV1 modulators being heterocyclidene acetamide derivatives.

The potassium channel Kv7.2/3 and the cation non-selective channel TRPV1 are co-expressed in the main pain pathways of the peripheral nociceptive system (DRG sensory neurons), which convey pain signals and have opposite functions. TRPV1 channels trigger the pain signals, while Kv7.2/3 channels inhibit them. Compounds that simultaneously function as openers of Kv7.2 and blockers of TRPV1 can depress neuronal hyper-excitability such as neuropathic pain.

SUMMARY OF THE INVENTION

According to an aspect of some embodiments of the present invention there is provided a compound represented by Formula I:

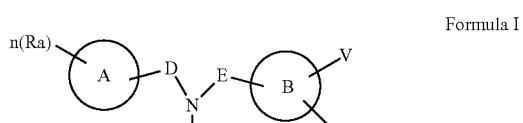

Formula I wherein:

A and B are each independently selected from an aryl and a heteroaryl;

D is $(CR_dR_e)u$;

E is $(CR_fR_g)v$;

u and v are each independently 0 or 1;

n is an integer of from 1 to 5;

m is an integer of from 0 to 5;

Re, Rd, Rf and Rg are each independently selected from hydrogen, alkyl, cycloalkyl, halo, haloalkyl, haloalkoxy, alkoxy, aryl, heteroaryl, heteroalicyclic, aryloxy, hydroxy, amine, alkylamine, thiohydroxy, thioalkoxy, thioaryloxy, cyano, carboxylate, amide, carbamate, sulphonyl and sulphonamide;

Ra and Rb are each independently a substituent selected from alkyl, cycloalkyl, halo, haloalkyl, haloalkoxy, alkoxy, aryl, heteroaryl, heteroalicyclic, aryloxy, hydroxy, amine, alkylamine, thiohydroxy, thioalkoxy, thioaryloxy, cyano, carboxylate, amide, carbamate, sulphonyl, and sulphonamide, or, alternatively, at least two of Ra substituent, Re, Rd and $R_1$ form together an alicyclic or heterocylic ring and/or at least two of Rb substituent, Rf and Rg for together an alicylic or heterocyclic ring, wherein when n is greater than 1, each Ra is the same or different substituent, and when m is greater than 1, each Rb is the same or different substituent;

$R_1$ is hydrogen, alkyl, cycloalkyl or aryl; and

V is $(CR_2R_3)k-C(=O)-NR_4-Z$, and is at the meta position with respect to the $N-R_1$, wherein:

k is an integer of from 0 to 2;

$R_2$ and $R_3$ are each independently selected from hydrogen, halo, alkyl, cycloalkyl, and aryl;

$R_4$ is hydrogen, alkyl, cycloalkyl, or aryl; and

Z is represented by Formula II:

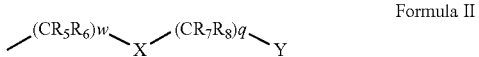

Formula II wherein:

w and q are each independently an integer of from 0 to 4, provided that w+q is at least 2;

X is selected from O and $NR_9$, or is absent;

Y is selected from $OR_{10}$ and $SR_{10}$;

$R_5$, $R_6$, $R_7$ and $R_8$ are each independently selected from hydrogen, halo, alkyl, haloalkyl, cycloalkyl, heteroalicyclic, aryl, alkylamino, alkoxy, haloalkoxy and aryloxy, or, alternatively, two of $R_5$, $R_6$, $R_7$, $R_8$ and $R_9$ form together an alicyclic or heteroalicyclic ring; and $R_{10}$ is selected from hydrogen, alkyl, cycloalkyl and aryl, or, alternatively, two of $R_5$, $R_6$, $R_7$, $R_8$, $R_9$ and $R_{10}$ form together an alicyclic or heteroalicyclic ring, provided that:

at least one of Ra is selected from alkyl, haloalkyl, cycloalkyl and aryl; and/or at least one of Rb is halo; and/or at least one of $R_5$, $R_6$, $R_7$ and $R_8$ is alkyl, cycloalkyl, heteroalicyclic or aryl; and/or at least two of $R_5$, $R_6$, $R_7$, $R_8$ and $R_9$ form together an alicyclic or heteroalicyclic ring.

According to some of any of the embodiments described herein, A is aryl.

According to some of any of the embodiments described herein, B is aryl.

According to some of any of the embodiments described herein, A and B are each an aryl.

According to some of any of the embodiments described herein, A and B are each phenyl.

According to some of any of the embodiments described herein, $R_1$ is hydrogen.

According to some of any of the embodiments described herein, u is 0.

According to some of any of the embodiments described herein, v is 0.

According to some of any of the embodiments described herein, each of u and v is 0.

According to some of any of the embodiments described herein, A and B are each phenyl; $R_1$ is hydrogen; and each of u and v is 0.

According to some of any of the embodiments described herein, m is other than 0 and at least one of the Rb substituent(s) is halo.

According to some of any of the embodiments described herein, m is 1.

According to some of any of the embodiments described herein, the halo is at the para position with respect to the $NR_1$.

According to some of any of the embodiments described herein, the halo is fluoro.

According to some of any of the embodiments described herein, n is 3, 4 or 5, preferably 3.

According to some of any of the embodiments described herein, at least two of the Ra substituents are selected from halo and alkoxy.

According to some of any of the embodiments described herein, at least two of the Ra substituents are each halo.

According to some of any of the embodiments described herein, the halo is chloro.

According to some of any of the embodiments described herein, at least one of the Ra substituent(s) is selected from alkyl, haloalkyl, cycloalkyl, aryl, alkoxy, alkylamino, heteroaryl and heteroalicyclic, or, alternatively, two Ra substituents form together a cyclic ring.

According to some of any of the embodiments described herein, at least one of the Ra substituent(s) is selected from alkyl, haloalkyl, cycloalkyl and aryl.

According to some of any of the embodiments described herein, at least one of the Ra substituent(s) is alkyl or cycloalkyl.

According to some of any of the embodiments described herein, at least one of the Ra substituents is at the ortho position with respect to the $NR_1$.

According to some of any of the embodiments described herein, at least one of the Ra substituent(s) is alkyl, haloalkyl, cycloalkyl, aryl, alkoxy, alkylamino, heteroaryl or heteroalicyclic, and is at the ortho position with respect to the $NR_1$.

According to some of any of the embodiments described herein, n is 3, one of the Ra substituent(s) is alkyl, haloalkyl, cycloalkyl, aryl, alkoxy, alkylamino, heteroaryl or heteroalicyclic, and is at the ortho position with respect to the $NR_1$, and the two other Ra substituents are each halo.

According to some of any of the embodiments described herein, n is 3; one of the Ra substituent(s) is alkyl, haloalkyl, cycloalkyl, aryl, alkoxy, alkylamino, heteroaryl or heteroalicyclic, and is at the ortho position with respect to the $NR_1$; the two other Ra substituents are each halo; m is 1; and Rb is halo and is at the para position with respect to the $NR_1$.

According to some of any of the embodiments described herein, k is 1.

According to some of any of the embodiments described herein, $R_2$ and $R_3$ are each hydrogen.

According to some of any of the embodiments described herein, X is absent.

According to some of any of the embodiments described herein, X is O.

According to some of any of the embodiments described herein, at least one of $R_5$, $R_6$, $R_7$ and $R_8$ is independently selected from alkyl, haloalkyl and halo, and/or at least two of $R_5$, $R_6$, $R_7$ and $R_8$ form together an alicyclic ring.

According to some of any of the embodiments described herein, at least two of $R_5$, $R_6$, $R_7$ and $R_8$ are independently selected from alkyl, haloalkyl and halo.

According to some of any of the embodiments described herein, at least two of $R_5$, $R_6$, $R_7$ and $R_8$ are each independently an alkyl.

According to some of any of the embodiments described herein, q is 1 and at least one or each of $R_7$ and $R_8$ is alkyl.

According to some of any of the embodiments described herein, w is 1 or 2.

According to some of any of the embodiments described herein, $R_5$ and $R_6$ are each hydrogen.

According to some of any of the embodiments described herein, at least two of $R_5$, $R_6$, $R_7$ and $R_8$ form together an alicyclic ring.

According to some of any of the embodiments described herein, at least one of the Ra substituent(s) is selected from alkyl, haloalkyl, cycloalkyl, aryl, alkoxy, alkylamino, heteroaryl and heteroalicyclic, or, alternatively, two Ra substituents form together a cyclic ring.

According to some of any of the embodiments described herein, Y is $OR_{10}$, and $R_{10}$ is hydrogen.

According to an aspect of some embodiments of the present invention there is provided a pharmaceutical composition comprising the compound as described herein in any of the respective embodiments and any combination thereof and a pharmaceutically acceptable carrier.

According to an aspect of some embodiments of the present invention there is provided a compound or a composition, as described herein in any of the respective embodiments and any combination thereof, for use in modulating an activity of a voltage-dependent potassium channel.

According to some of any of the embodiments described herein, the potassium channel is Kv7.2/7.3.

According to some of any of the embodiments described herein, the modulating comprises opening the channel.

According to an aspect of some embodiments of the present invention there is provided a compound or a composition, as described herein in any of the respective embodiments and any combination thereof, for use in modulating an activity of TRPV1.

According to some of any of the embodiments described herein, the modulating comprises (blocking) inhibiting the activity of TRPV1.

According to an aspect of some embodiments of the present invention there is provided a compound or a composition, as described herein in any of the respective embodiments and any combination thereof, for use in modulating an activity of both a voltage-dependent potassium channel and TRPV1.

According to some of any of the embodiments described herein, modulating the activity of the voltage-dependent potassium channel comprises opening the channel and wherein modulating the activity of the TRPV1 channel comprises inhibiting an activity of the channel.

According to some of any of the embodiments described herein, the potassium channel is Kv7.2/7.3.

According to an aspect of some embodiments of the present invention there is provided a compound or a composition, as described herein in any of the respective embodiments and any combination thereof, for use in treating a medical condition associated with an activity of a voltage-dependent potassium channel and/or a TRPV1 channel.

According to some of any of the embodiments described herein, the medical condition is neuropathic pain.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 15A-C present comparative plots demonstrating the inhibition of DRG evoked spike discharge by NH91 (FIG. 15A), and the absence of any effect by NH91 (5 μM) on the inward voltage-dependent Ca2+ and Na+ current in DRG neurons (FIGS. 15B-C).

DESCRIPTION OF SPECIFIC EMBODIMENTS OF THE INVENTION

Figure 1A:
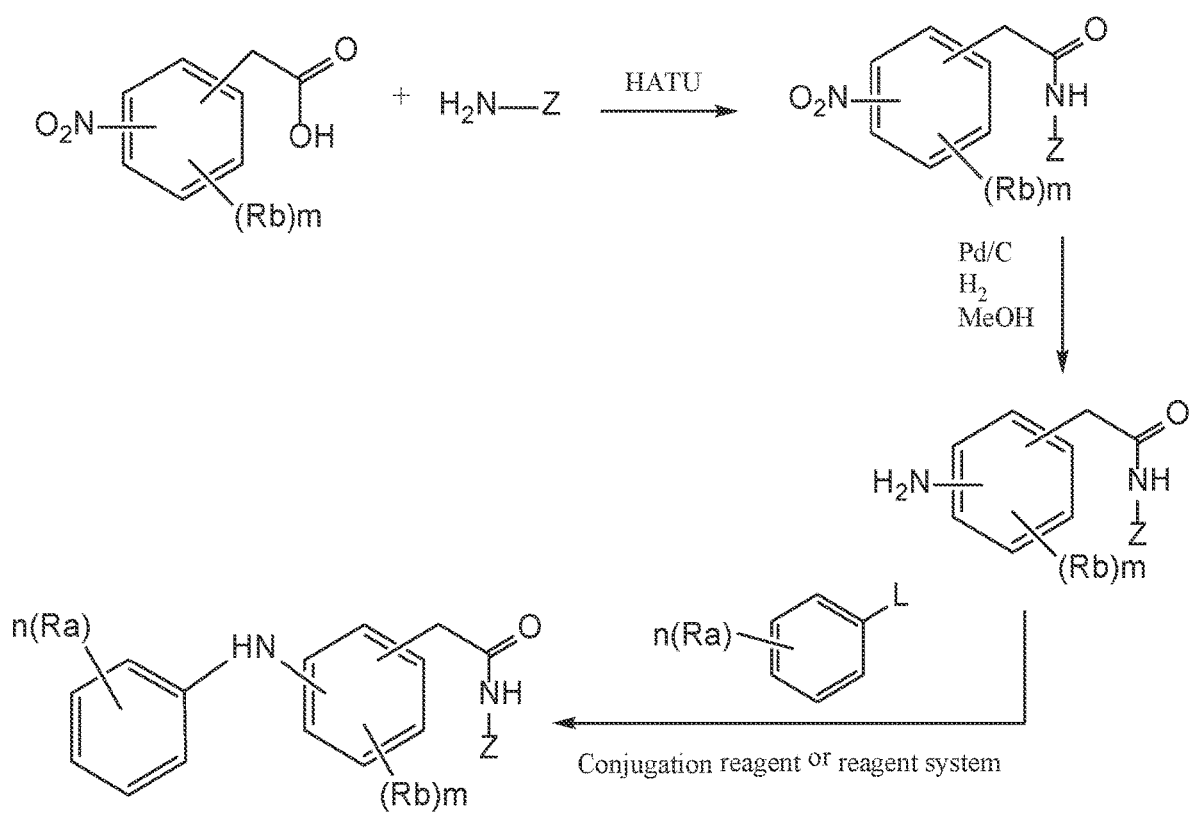
FIGS. 1A-B present exemplary general synthetic pathways used for preparing diphenylamine derivatives as presented in FIG. 20.

The present invention, in some embodiments thereof, relates to novel derivatives of diphenylamine and, more particularly, but not exclusively, to diphenylamine derivatives featuring a dual activity as modulators of both potassium ion and TRPV1 channels, which are usable in the treatment of various pathologies that are related to these channels, such as neuropathic pain.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have devised a one-two punch strategy that uses dual channel targeting, activating Kv7.2 and inhibiting TRPV1, by the same molecule to increase the potency of the drug (e.g., by additivity/synergy) and thereby allow lower dosage, which should reduce the risk of off-targets.

Embodiments of the present invention relate to newly designed compounds, having a di(aryl/heteroaryl)amide skeleton (e.g., a diphenylamine skeleton), such as represented by Formula I as described herein in any of the respective embodiments and any combination thereof, and to the use of these compounds in modulating an activity of a voltage-dependent potassium channel such as Kv7.2/7.3 and/or of TRPV1 and in treating medical conditions associated with an activity of these channels. Embodiments of the present invention further relate to processes of preparing the disclosed compounds.

According to an aspect of some embodiments of the present invention there are provided compounds, which are collectively represented by Formula I:

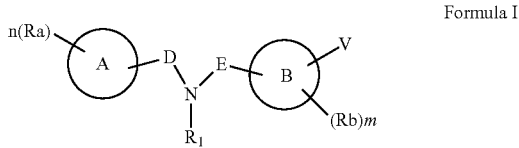

Formula I wherein:
A and B are each independently selected from an aryl and a heteroaryl;
D is $(CR_dR_e)u$;
E is $(CR_fR_g)v$;
u and v are each independently 0 or 1;
n is an integer of from 1 to 5;
m is an integer of from 0 to 5;
Re, Rd, Rf and Rg are each independently selected from hydrogen, alkyl, cycloalkyl, halo, haloalkyl, haloalkoxy, alkoxy, aryl, heteroaryl, heteroalicyclic, aryloxy, hydroxy, amine, alkylamine, thiohydroxy, thioalkoxy, thioaryloxy, cyano, carboxylate, amide, carbamate, sulphonyl and sulphonamide;
Ra and Rb are each independently a substituent selected from alkyl, cycloalkyl, halo, haloalkyl, haloalkoxy, alkoxy, aryl, heteroaryl, heteroalicyclic, aryloxy, hydroxy, amine, alkylamine, thiohydroxy, thioalkoxy, thioaryloxy, cyano, carboxylate, amide, carbamate, sulphonyl, and sulphonamide, or, alternatively, at least two of Ra substituent, Re, Rd and $R_1$ form together an alicyclic or heterocylic ring and/or at least two of Rb substituent, Rf and Rg for together an alicylic or heterocyclic ring, wherein when n is greater than 1, each Ra is the same or different substituent, and when m is greater than 1, each Rb is the same or different substituent;
$R_1$ is hydrogen, alkyl, cycloalkyl or aryl; and
V is $(CR_2R_3)k-C(=O)-NR_4-Z$, and is at the meta position with respect to the $N-R_1$, wherein:
k is an integer of from 0 to 2;
$R_2$ and $R_3$ are each independently selected from hydrogen, halo, alkyl, cycloalkyl, and aryl;
$R_4$ is hydrogen, alkyl, cycloalkyl, or aryl; and
Z is represented by Formula II:

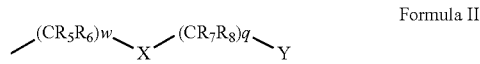

Formula II wherein:
w and q are each independently an integer of from 0 to 4, provided that w+q is at least 2;
X is selected from O and $NR_9$, or is absent;
Y is selected from $OR_{10}$ and $SR_{10}$;
$R_5$, $R_6$, $R_7$ and $R_8$ are each independently selected from hydrogen, halo, alkyl, haloalkyl, cycloalkyl, heteroalicyclic, aryl, alkylamino, alkoxy and aryloxy, or, alternatively, two of $R_4$, $R_5$, $R_6$, $R_7$, $R_8$ and $R_9$ form together an alicyclic or heteroalicyclic ring (depending on the nature of the $R_4$, $R_5$, $R_6$, $R_7$, $R_8$ and $R_9$ substituent the forms the ring); and
$R_{10}$ is selected from hydrogen, alkyl, cycloalkyl and aryl, or, alternatively, two of $R_5$, $R_6$, $R_7$, $R_8$, $R_9$ and $R_{10}$ form together an alicyclic or heteroalicyclic ring. According to some embodiments of the present invention, a compound of the present embodiments features at least one, at least two, at least three, or all of the following:
at least one of the Ra substituents is selected from alkyl, haloalkyl, cycloalkyl, aryl, alkoxy, alkylamino, heteroaryl and heteroalicyclic, or, alternatively, two Ra substituents form together a cyclic ring; and/or
at least one of the Rb substituents is halo; and/or
at least one of $R_5$, $R_6$, $R_7$ and $R_8$ is alkyl, halo, haloalkyl, cycloalkyl, heteroalicyclic or aryl; and/or
at least two of $R_5$, $R_6$, $R_7$, $R_8$ and $R_9$, and $R_{10}$, if present, form together an alicyclic or heteroalicyclic ring.

According to some embodiments of the present invention, a compound of the present embodiments features at least one, at least two, at least three, or all of the following:
at least one of the Ra substituents is at the ortho position with respect to D (if present) or to $NR_1$ (if D is absent) and this Ra substituent at the ortho position is selected from alkyl, haloalkyl, cycloalkyl, aryl, alkoxy, alkylamino, heteroaryl and heteroalicyclic, or, alternatively, the Ra substituent at the ortho position form together with another Ra substituent a cyclic ring, as described herein; and/or
at least one of the Rb substituents is halo, and is at the ortho position with respect to variable V; and/or
at least one of $R_5$, $R_6$, $R_7$ and $R_8$ is alkyl, halo, haloalkyl, cycloalkyl, heteroalicyclic or aryl; and/or
at least two of $R_5$, $R_6$, $R_7$, $R_8$ and $R_9$, and $R_{10}$, if present, form together an alicyclic or heteroalicyclic ring.

According to some embodiments of the present invention, a compound of the present embodiments features at least one, at least two, at least three, or all of the following:
at least one of the Ra substituents is at the ortho position with respect to D (if present) or to $NR_1$ (if D is absent) and this Ra substituent at the ortho position is selected from alkyl, haloalkyl, cycloalkyl and aryl; and/or
at least one of the Rb substituents is halo, preferably fluoro, and is at the ortho position with respect to variable V; and/or
at least one of $R_5$, $R_6$, $R_7$ and $R_8$ is alkyl, halo, haloalkyl, cycloalkyl, heteroalicyclic or aryl and/or at least two of $R_5$, $R_6$, $R_7$ and $R_8$ form together an alicyclic or heteroalicyclic ring.

According to some of any of the embodiments described herein, A is aryl.

According to some of any of the embodiments described herein, B is aryl.

According to some of any of the embodiments described herein, A is aryl and B is aryl or heteroaryl (for example, pyridine).

According to some of any of the embodiments described herein, A and B are each an aryl.

According to some of any of the embodiments described herein for A and/or B, the aryl is phenyl.

According to some of any of the embodiments described herein for A and/or B, the heteroaryl ring is pyridine.

Whenever one or both of A and B is/are a heteroaryl, the one or more heteroatoms of the heteroaryl can be at any position with respect to the group D-$NR_1$-E linking the two rings.

According to some of any of the embodiments described herein, A and B are each phenyl.

According to some of any of the embodiments described herein, D is (CRdRe)u, and Rd and Re are each hydrogen. Alternatively, one or both of Rd and Re is an alkyl, preferably an unsubstituted alkyl, preferably a lower alkyl, as defined herein, preferably a lower unsubstituted alkyl. In some of these embodiments, u is 1. In some embodiments, u is 0 and D is absent.

According to some of any of the embodiments described herein, E is (CRfRg)v, and Rf and Rg are each hydrogen. Alternatively, one or both of Rf and Rg is an alkyl, preferably an unsubstituted alkyl, preferably a lower alkyl, as defined herein, preferably a lower unsubstituted alkyl. In some of these embodiments, v is 1. In some embodiments, v is 0 and E is absent.

According to some of any of the embodiments described herein, each of u and v is 0, and both D and E are absent.

According to some of any of the embodiments described herein, A and B are each phenyl and D and E are both absent.

Compounds according to these embodiments are diphenylamine derivatives and can be collectively represented by Formula Ia:

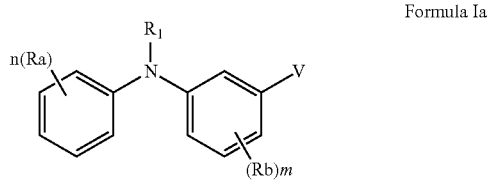

Formula Ia wherein Ra, Rb, n, m, $R_1$ and X are as described for Formula I and in any of the respective embodiments and any combination thereof.

In some of any of the embodiments described herein (e.g., for Formulae I and Ia), $R_1$ is hydrogen or an alkyl, preferably an unsubstituted alkyl, preferably a lower alkyl, as defined herein, preferably a lower unsubstituted alkyl.

In some of any of the embodiments described herein (e.g., for Formulae I and Ia), $R_1$ is hydrogen.

According to some of any of the embodiments described herein, there is at least one substituent on the B ring, such that m is other than 0 (e.g., is 1, 2, 3 or 4).

According to some of these embodiments, at least one of the Rb substituents is at the para position with respect to the -E-$NR_1$-D group, or with respect to —$NR_1$—, if E is absent, or is at the ortho position with respect to V, in Formula I or Ia.

According to some of any of the embodiments described herein, m is other than 0 and at least one of the Rb substituent(s) is halo.

According to some of any of the embodiments described herein, m is other than 0 and at least one of the Rb substituent(s) is halo, and the halo substituent is at the para position with respect to the -E-$NR_1$-D group, or with respect to —$NR_1$—, if E is absent, or is at the ortho position with respect to V, in Formula I or Ia.

According to some of any of the embodiments described herein, m is 1, such that there is one substituent on the B ring, in addition to V.

According to some of these embodiments, the Rb substituent is halo.

According to some of these embodiments, the Rb substituent is at the para position with respect to the -E-$NR_1$-D group, or with respect to —$NR_1$—, if E is absent, or is at the ortho position with respect to V, in Formula I or Ia.

According to some of any of the embodiments described herein, m is 1 and the Rb substituent is halo and is at the para position with respect to the -E-$NR_1$-D group, or with respect to —$NR_1$—, if E is absent, or is at the ortho position with respect to V, in Formula I or Ia.

According to some of any of the embodiments described herein, when m is 1 and Rb is halo, the halo is fluoro.

According to some of any of the embodiments described herein, m is 1, Rb is fluoro and is at the para position with respect to the -E-$NR_1$-D group, or with respect to —$NR_1$—, if E is absent, or is at the ortho position with respect to V, in Formula I or Ia.

According to some of any of the embodiments described herein, m is other than 0, such that there are one or more Rb substituents on the B ring, and the one or more Rb substituents can be the same or different from one another. In some of these embodiments, one of the Rb substituents is at the para position with respect to the -E-$NR_1$-D group, or with respect to —$NR_1$—, if E is absent, or is at the ortho position with respect to V, in Formula I or Ia.

In some embodiments, the one or more Rb substituents can be, for example, selected from halo, alkyl, haloalkyl, cycloalkyl, heteroalicyclic, aryl, heteroaryl, cyano, alkylamine, etc., or, two Rb substituents can form together a cyclic ring, as defined herein.

According to some embodiments of the present invention, m is 1 and the Rb substituent can be halo, alkyl, haloalkyl, cycloalkyl, heteroalicyclic, aryl, heteroaryl, cyano, alkylamine. According to some of these embodiments, the Rb substituent is at the para position with respect to the -E-$NR_1$-D group, or with respect to —$NR_1$—, if E is absent, or is at the ortho position with respect to V, in Formula I or Ia.

According to some of any of the embodiments described herein, there is at least one Ra substituent on the A ring in Formula I, such that n is 1, 2, 3, 4 or 5.

According to some of any of the embodiments described herein, at least one of the Ra substituents in at the ortho position with respect to the -D-$NR_1$-E group, or to the —$NR_1$— group in case D is absent.

According to some of any of the embodiments described herein, there are at least two Ra substituents on the A ring, such that n is 2, 3, 4 or 5. According to some of these embodiments, at least one of the Ra substituents in at the ortho position with respect to the -D-$NR_1$-E group, or to the —$NR_1$— group in case D is absent.

According to some of any of the embodiments described herein, there are at least three Ra substituents on the A ring, such that n is 3, 4 or 5. According to some of these embodiments, at least one of the Ra substituents in at the ortho position with respect to the -D-$NR_1$-E group, or to the —$NR_1$— group in case D is absent.

According to some of any of the embodiments described herein, there are three Ra substituents on the A ring, such that n is 3. According to some of these embodiments, at least one of the Ra substituents in at the ortho position with respect to the -D-$NR_1$-E group, or to the —$NR_1$— group in case D is absent.

According to some of any of the embodiments described herein, an Ra substituent can be a halo, an alkoxy, a haloalkyl, an alkyl, a cycloalkyl, an amine (preferably an alkylamine), a heteroalicyclic, an aryl and a heteroaryl, and, when n is 2, 3, 4, 5, any combination of the foregoing, or, alternatively, two Ra substituents form a cyclic ring. According to some of these embodiments, at least one of the Ra substituents in at the ortho position with respect to the -D-NR$_1$-E group, or to the —NR$_1$— group in case D is absent.

According to some of any of the embodiments described herein, when n is 2, 3, 4 or 5, and is preferably 3, two of more of the Ra substituents are selected halo and alkoxy, that is, the Ra substituents can include two halo substituents, two alkoxy substituents, or one halo substituent and one alkoxy substituent. In some of any of the embodiments described herein, when an Ra substituent is alkoxy, the alkoxy is a haloalkoxy as defined herein.

According to some of any of the embodiments described herein, n is 2, 3, 4 or 5, preferably 3, and at least two of the Ra substituents are each halo.

According to some of any of the embodiments described herein, n is 2, 3, 4 or 5, preferably 3, and at least two of the Ra substituents are each chloro. Alternatively, one or both of the halo substituents is fluoro.

According to some of any of the embodiments described herein, at least one of the Ra substituent(s) is selected from alkyl, haloalkyl, cycloalkyl, aryl, alkoxy, alkylamino, heteroaryl and heteroalicyclic, or, alternatively, two Ra substituents form together a cyclic ring.

According to some of any of the embodiments described herein, at least one of the Ra substituent(s) is selected from alkyl, haloalkyl, cycloalkyl and aryl.

According to some of any of the embodiments described herein, at least one of the Ra substituent(s) is alkyl or cycloalkyl.

According to some of any of the embodiments described herein, at least one of the Ra substituent(s) is alkyl, haloalkyl, cycloalkyl, aryl, alkoxy, alkylamino, heteroaryl or heteroalicyclic, and is at the ortho position with respect to the -D-NR$_1$-E group, or with respect to the —NR$_1$— group if D is absent.

According to some of any of the embodiments described herein, n is 3, one of the Ra substituent(s) is alkyl, haloalkyl, cycloalkyl, aryl, alkoxy, alkylamino, heteroaryl or heteroalicyclic, and is at the ortho position with respect to the -D-NR$_1$-E group, or with respect to the —NR$_1$— group if D is absent, and the two other Ra substituents are each halo (e.g., chloro).

According to some of any of the embodiments described herein, when n is 2, 3, 4 or 5, at least one of the Ra substituents is at the ortho position with respect to the -D-NR$_1$-E group, or with respect to the —NR$_1$— group if D is absent, and the other one or more substituents can be at any other position(s). In some embodiments, the other one or more substituents are at the ortho and/or para position(s) with respect to the -D-NR$_1$-E group, or with respect to the —NR$_1$— group if D is absent.

According to some of any of the embodiments described herein, when n is 3, and each of the Ra substituents is halo, for example, chloro and/or fluoro, or each is chloro.

In some of these embodiments, the halo substituents are at the ortho and para position(s) with respect to the -D-NR$_1$-E group, or with respect to the —NR$_1$— group if D is absent.

According to some of any of the embodiments described herein, n is 3; one of the Ra substituent(s) is alkyl, haloalkyl, cycloalkyl, aryl, alkoxy, alkylamino, heteroaryl or heteroalicyclic, and is at the ortho position with respect with respect to the -D-NR$_1$-E group, or with respect to the —NR$_1$— group if D is absent; and the two other Ra substituents are each halo, as described herein. In some of these embodiments, the two halo Ra substituents are at the ortho and para position(s) with respect to the -D-NR$_1$-E group, or with respect to the —NR$_1$— group if D is absent.

According to some of any of the embodiments described herein, n is 3; one of the Ra substituent(s) is alkyl, preferably a lower alkyl, or a cycloalkyl, and is at the ortho position with respect with respect to the -D-NR$_1$-E group, or with respect to the —NR$_1$— group if D is absent; and the two other Ra substituents are each halo, as described herein. In some of these embodiments, the two halo Ra substituents are at the ortho and para position(s) with respect to the -D-NR$_1$-E group, or with respect to the —NR$_1$— group if D is absent.

According to some of any of the embodiments described herein (e.g., for Formula I or Ia), n is 3; one of the Ra substituent(s) is alkyl, haloalkyl, cycloalkyl, aryl, alkoxy, alkylamino, heteroaryl or heteroalicyclic, and is at the ortho position with respect with respect to the -D-NR$_1$-E group, or with respect to the —NR$_1$— group if D is absent; the two other Ra substituents are each halo, as described herein; m is 1; and Rb is halo (e.g., fluoro) and is at the para position with respect to the -E-NR$_1$-D- group, or to —NR$_1$— is E is absent.

According to some of any of the embodiments described herein (e.g., for Formula I or Ia), n is 3; one of the Ra substituent(s) is alkyl, haloalkyl, cycloalkyl, aryl, alkoxy, alkylamino, heteroaryl or heteroalicyclic, and is at the ortho position with respect with respect to the -D-NR$_1$-E group, or with respect to the —NR$_1$— group if D is absent; the two other Ra substituents are each halo, as described herein; and m is 1 and the Rb substituent is at the para position with respect to the -E-NR$_1$-D- group, or to —NR$_1$— is E is absent.

According to some of any of the embodiments described herein (e.g., for Formula I or Ia), n is 3; one of the Ra substituent(s) is alkyl, haloalkyl, cycloalkyl, aryl, alkoxy, alkylamino, heteroaryl or heteroalicyclic, and is at the ortho position with respect with respect to the -D-NR$_1$-E group, or with respect to the —NR$_1$— group if D is absent; the two other Ra substituents are each halo, as described herein; m is 1; and the Rb substituent is halo (e.g., fluoro).

According to some of any of the embodiments described herein (e.g., for Formula I or Ia), one of the Ra substituent(s) is alkyl, haloalkyl, cycloalkyl, aryl, alkoxy, alkylamino, heteroaryl or heteroalicyclic, preferably alkyl (e.g., lower alkyl) or cycloalkyl, and is at the ortho position with respect with respect to the -D-NR$_1$-E group, or with respect to the —NR$_1$— group if D is absent; m is 1; and Rb is halo (e.g., fluoro) and is at the para position with respect to the -E-NR$_1$-D- group, or to —NR$_1$— is E is absent.

According to some of any of the embodiments described herein (e.g., for Formula I or Ia), one of the Ra substituent(s) is alkyl, haloalkyl, cycloalkyl, aryl, alkoxy, alkylamino, heteroaryl or heteroalicyclic, preferably alkyl (e.g., lower alkyl) or cycloalkyl, and is at the ortho position with respect with respect to the -D-NR$_1$-E group, or with respect to the —NR$_1$— group if D is absent; m is 1 and the Rb substituent is at the para position with respect to the -E-NR$_1$-D- group, or to —NR$_1$— is E is absent.

According to some of any of the embodiments described herein (e.g., for Formula I or Ia), one of the Ra substituent(s) is alkyl, haloalkyl, cycloalkyl, aryl, alkoxy, alkylamino, heteroaryl or heteroalicyclic, preferably alkyl (e.g., lower alkyl) or cycloalkyl; m is 1; and the Rb substituent is halo (e.g., fluoro).

In some of any of the embodiments where there are two halo Ra substituents, the two halo Ra substituents are at the ortho and para position(s) with respect to the -D-$NR_1$-E group, or with respect to the —$NR_1$— group if D is absent.

According to some of any of the embodiments described herein, k is 1. Optionally, k is 0.

According to some of any of the embodiments described herein, when k is other than 0, $R_2$ and $R_3$ are each hydrogen. Alternatively, one or both of $R_2$ and $R_3$ is an alkyl, or a haloalkyl, preferably a lower alkyl.

According to some of any of the embodiments described herein, k is 1 and $R_2$ and $R_3$ are each hydrogen.

According to some of any of the embodiments described herein, $R_4$ is hydrogen. Optionally, $R_4$ is an alkyl, preferably a lower alkyl. Further optionally, $R_4$ forms together with one or more of $R_5$, $R_6$, $R_7$ and $R_8$, or with one or more of $R_5$, $R_6$, $R_7$, $R_8$, $R_9$ (if present) and $R_{10}$ (if other than hydrogen) a heterocylic ring, preferably a heteroalicyclic ring.

According to some of any of the embodiments described herein, k is 1; $R_2$ and $R_3$ are each hydrogen; and $R_4$ is hydrogen.

According to some of any of the embodiments described herein, X is absent, such that Z is an alkylene chain or is an alicyclic ring (a cycloalkyl) substituted by Y, or is a heteroalicyclic ring in which Y and optionally $NR_4$ forms a part of the ring.

According to some of any of the embodiments described herein, X is O, such that Z is an alkylene glycol chain terminated with Y, or is an alkylene chain ($CR_5R_6$)w, linked to a heteroalicyclic ring formed between X and Y, or linked to an alicyclic ring formed between two of $R_7$, $R_8$ (e.g., in case q is more than 1).

According to some of any of the embodiments described herein, X is O and Z is an alkylene glycol chain terminated by Y. In some of these embodiments, w is 1, 2, or 3, preferably 2, and q is 1, 2, or 3, preferably 2.

According to some of any of the embodiments described herein, X is absent, and Z is an alkylene chain composed of ($CR_5R_6$)w and ($CR_7R_8$)q.

According to some of any of the embodiments described herein, X is absent and Z is an alicyclic ring (a cycloalkyl), formed of ($CR_5R_6$)w and ($CR_7R_8$)q where two or more of $R_5$, $R_6$, $R_7$ and $R_8$ form the ring, substituted by Y.

According to some of any of the embodiments described herein, the sum of w and q is at least 2, and in some embodiments it is at least 3, for example, is 3, 4, 5 or 6 or more.

According to some of any of the embodiments described herein, at least one of $R_5$, $R_6$, $R_7$ and $R_8$ is independently selected from alkyl, haloalkyl and halo, and/or at least two of $R_5$, $R_6$, $R_7$ and $R_8$ form together an alicyclic ring.

According to some of any of the embodiments described herein, at least two of $R_5$, $R_6$, $R_7$ and $R_8$ are independently selected from alkyl, haloalkyl and halo.

According to some of any of the embodiments described herein, at least two of $R_5$, $R_6$, $R_7$ and $R_8$ are each independently an alkyl, preferably a lower alkyl.

According to some of any of the embodiments described herein, q is 1 and at least one or each of $R_7$ and $R_8$ is alkyl, preferably a lower alkyl.

According to some of any of the embodiments described herein, w is 1 or 2.

According to some of any of the embodiments described herein, $R_5$ and $R_6$ are each hydrogen.

Whenever w is other than 1, it is composed of two or more ($CR_5R_6$) groups, and $R_5$ and $R_6$ is each of these groups can be the same or different.

Whenever q is other than 1, it is composed of two or more ($CR_7R_8$) groups, and $R_7$ and $R_8$ is each of these groups can be the same or different.

According to some of any of the embodiments described herein, q is 1 and w is 1 or 2.

According to some of these embodiments, at least one, and preferably both, of $R_7$ and $R_8$ is other than hydrogen, and is preferably an alkyl (e.g., a lower alkyl such as methyl). Alternatively, or in addition, at least one, and preferably both, of $R_5$ and $R_6$ in one of the ($CR_5R_6$) group(s) is other than hydrogen, and is preferably an alkyl (e.g., a lower alkyl such as methyl).

According to some of any of the embodiments described herein, q is 1 and w is 2.

According to some of any of the embodiments described herein, q is 2 and w is 2.

According to some of any of the embodiments described herein, in at least one of the ($CR_7R_8$) groups, at least one, and preferably both, of $R_7$ and $R_8$ is other than hydrogen, and is preferably an alkyl (e.g., a lower alkyl such as methyl). Alternatively, or in addition, at least one, and preferably both, of $R_5$ and $R_6$ in one of the ($CR_5R_6$) group(s) is other than hydrogen, and is preferably an alkyl (e.g., a lower alkyl such as methyl).

According to some of any of the embodiments described herein, X is absent and at least two of $R_5$, $R_6$, $R_7$ and $R_8$ form together an alicyclic ring. In some of these embodiments, w is 1 and q is 1 and $R_5$, $R_6$, $R_7$ and $R_8$ form together the alicyclic ring.

In some of these embodiments, w is 2 and q is 1, and an alicyclic ring if formed by the ($CR_5R_6$) group that not linked to $NR_4$. Alternatively, w is 1 and q is 2, and an alicyclic ring if formed by the ($CR_7R_8$) group that not linked to Y.

In some of any of the embodiments described herein, whenever Z comprises an alicylic ring, the ring is a 3-6-membered ring, or is a 5-membered ring or a 6-membered ring.

According to some of any of the embodiments described herein, X is absent and at least two of $R_5$, $R_6$, $R_7$ and $R_8$ for together an alicyclic ring (a cycloalkyl). In some of these embodiments, w and q are each 1 and in some embodiments, q is 1 and w is 1 or 2. In some of these embodiments $R_7$ and $R_8$ for together an alicyclic ring (a cycloalkyl), and in some other embodiments, all of $R_5$, $R_6$, $R_7$ and $R_8$ form together an alicyclic ring. The alicyclic ring can be of 3, 4, 5, 6 or more carbon atoms.

According to some of any of the embodiments described herein, X is O, and one or more of $R_5$, $R_6$, $R_7$ and $R_8$, preferably $R_7$ and/or $R_8$ is other than hydrogen (e.g., an alkyl, cycloalkyl, aryl).

According to some of any of the embodiments described herein, X is O, w is 2 or more and two of the $R_5$ and $R_6$ form together an alicyclic ring.

According to some of any of the embodiments described herein, X is O, q is 2 or more and two of the $R_7$ and $R_8$ form together an alicyclic ring.

According to some of any of the embodiments described herein, X is $NR_9$, and $R_9$ form together with one or more of $R_5$, $R_6$, $R_7$ and $R_8$ and heteroalicyclic ring.

In some of any of the embodiments described herein, at least one of $R_5$, $R_6$, $R_7$ and $R_8$ is independently selected from alkyl, haloalkyl and halo, and/or at least two of $R_5$, $R_6$, $R_7$ and $R_8$ form together an alicyclic ring, and at least one of the Ra substituent(s) is selected from alkyl, haloalkyl, cycloalkyl, aryl, alkoxy, alkylamino, heteroaryl and heteroalicyclic, or, alternatively, two Ra substituents form together a cyclic ring. In some of these embodiments, the Ra substituent is at the ortho position with respect to -D-$NR_1$-E- group as described herein. In some of any of these embodiments, m is 1 and the Rb substituent is halo, e.g., fluoro, as described herein in any of the respective embodiments.

In some of any of the embodiments described herein, at least one of $R_5$, $R_6$, $R_7$ and $R_8$ is independently an alkyl and/or at least two of $R_5$, $R_6$, $R_7$ and $R_8$ form together an alicyclic ring, and at least one of the Ra substituent(s) is selected from alkyl, haloalkyl, cycloalkyl, aryl, alkoxy, alkylamino, heteroaryl and heteroalicyclic, or, alternatively, two Ra substituents form together a cyclic ring. In some of these embodiments, the Ra substituent is at the ortho position with respect to -D-$NR_1$-E- group as described herein. In some of any of these embodiments, m is 1 and the Rb substituent is halo, e.g., fluoro, as described herein in any of the respective embodiments.

In some of any of the embodiments described herein, at least one of $R_5$, $R_6$, $R_7$ and $R_8$ is independently selected from alkyl, haloalkyl and halo, and/or at least two of $R_5$, $R_6$, $R_7$ and $R_8$ form together an alicyclic ring, and at least one of the Ra substituent(s) is selected from alkyl, haloalkyl and cycloalkyl. In some of these embodiments, the Ra substituent is at the ortho position with respect to -D-$NR_1$-E- group as described herein. In some of any of these embodiments, m is 1 and the Rb substituent is halo, e.g., fluoro, as described herein in any of the respective embodiments.

In some of any of the embodiments described herein, at least one of $R_5$, $R_6$, $R_7$ and $R_8$ is independently an alkyl, and/or at least two of $R_5$, $R_6$, $R_7$ and $R_8$ form together an alicyclic ring, and at least one of the Ra substituent(s) is selected from alkyl, haloalkyl, and cycloalkyl. In some of these embodiments, the Ra substituent is at the ortho position with respect to -D-$NR_1$-E- group as described herein. In some of any of these embodiments, m is 1 and the Rb substituent is halo, e.g., fluoro, as described herein in any of the respective embodiments.

According to some of any of the embodiments described herein, Y is hydroxy, such that Y is $OR_{10}$ and $R_{10}$ is hydrogen.

According to some of any of the embodiments described herein, a compound of Formula I or Ia as described herein feature a Log P value, when determined for octanol and water, of at least 3, preferably of at least 4, for example, of between 4 and 5.

Figure 19:
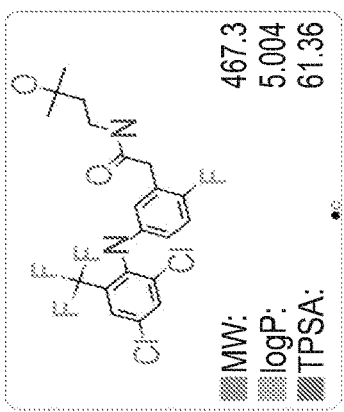
FIG. 19 presents the chemical structures and properties of exemplary compounds according to some embodiments of the present invention.
Figure 19:
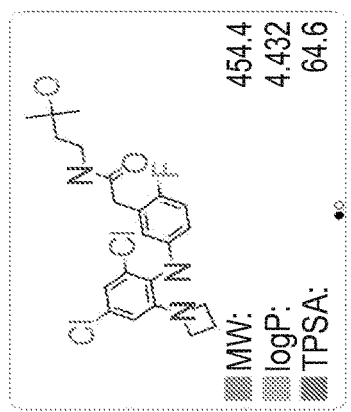
Figure 19:
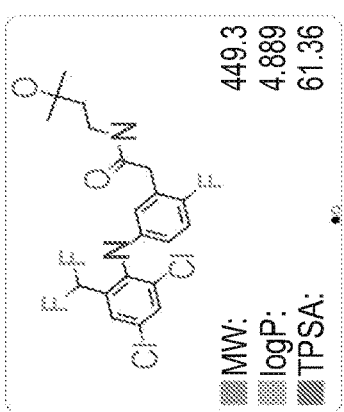
Figure 19:
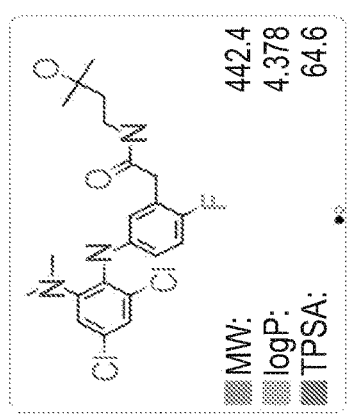
Figure 19:
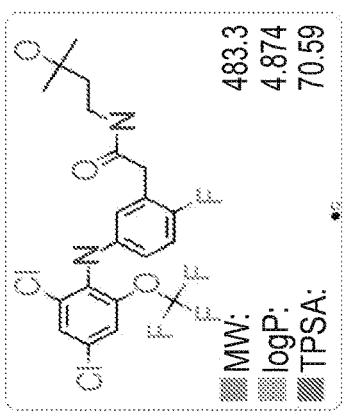
Figure 19:
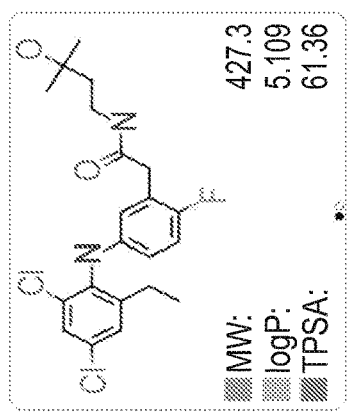
Figure 19:
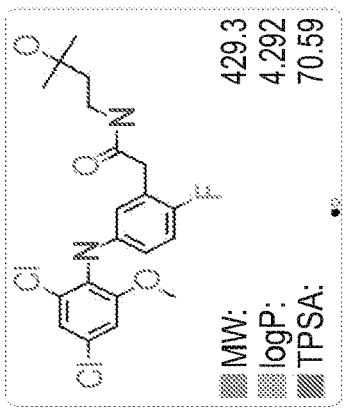
Figure 19:
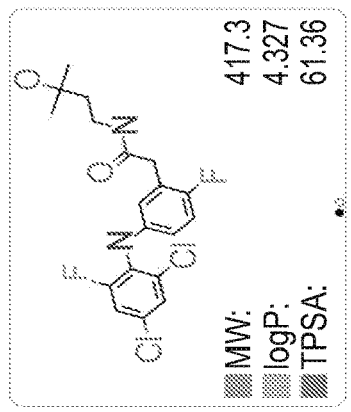
Figure 19:
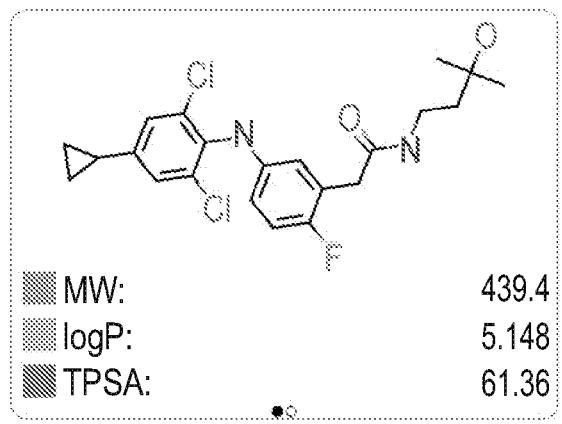
Figure 19:
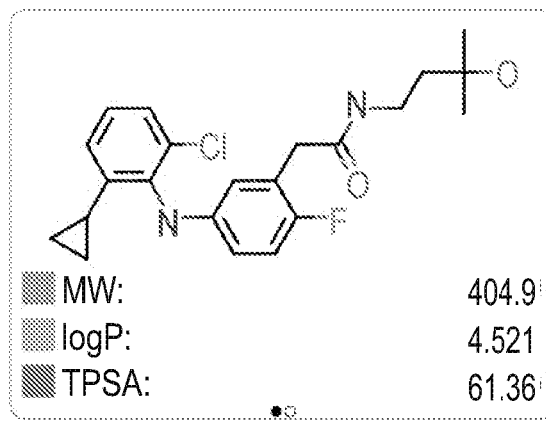
Figure 19:
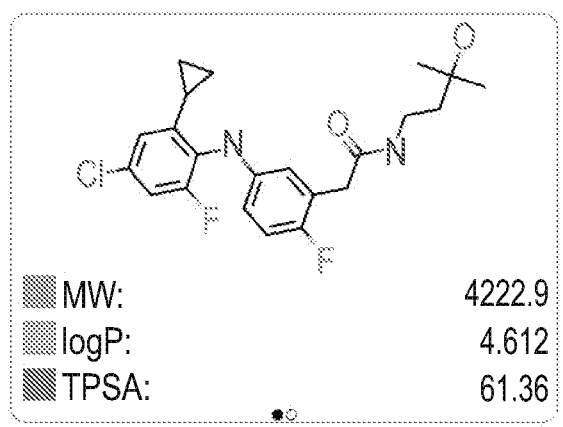
Figure 19:
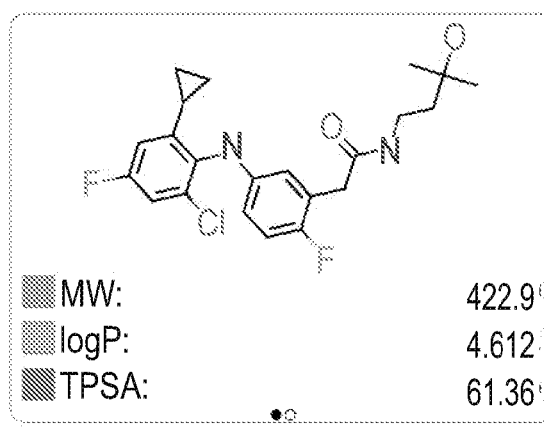
Figure 19:
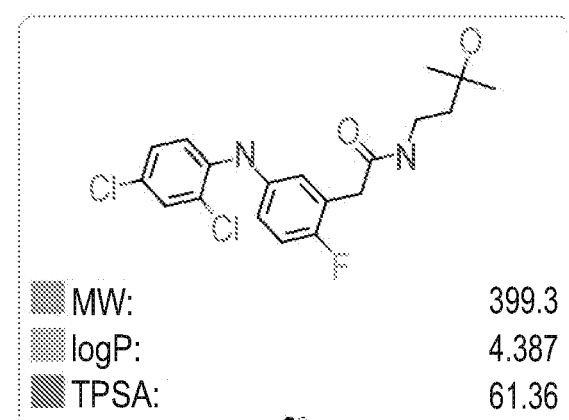
Figure 19:
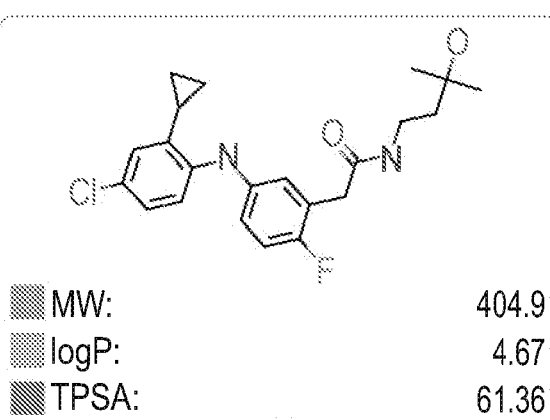
Figure 19:
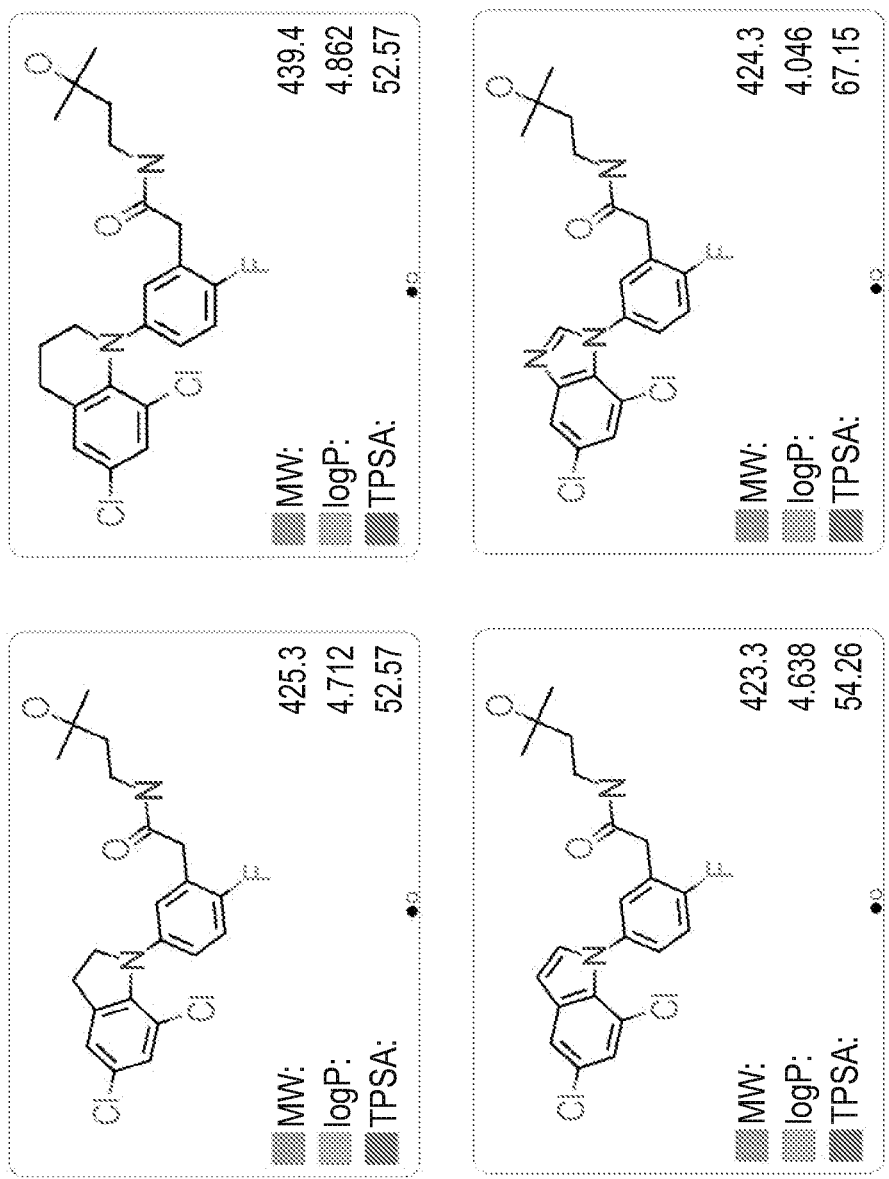
Figure 19:
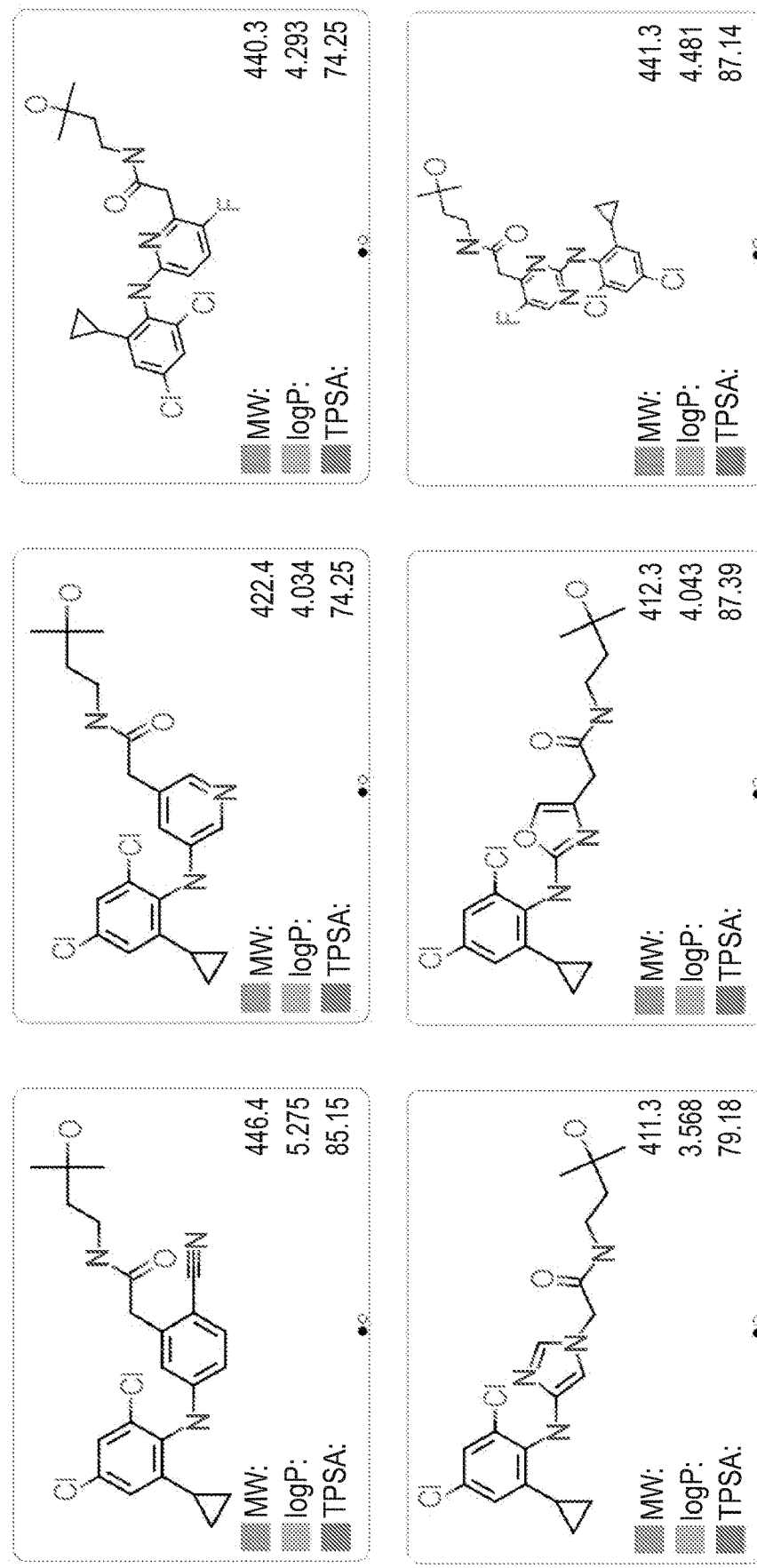
Figure 19:
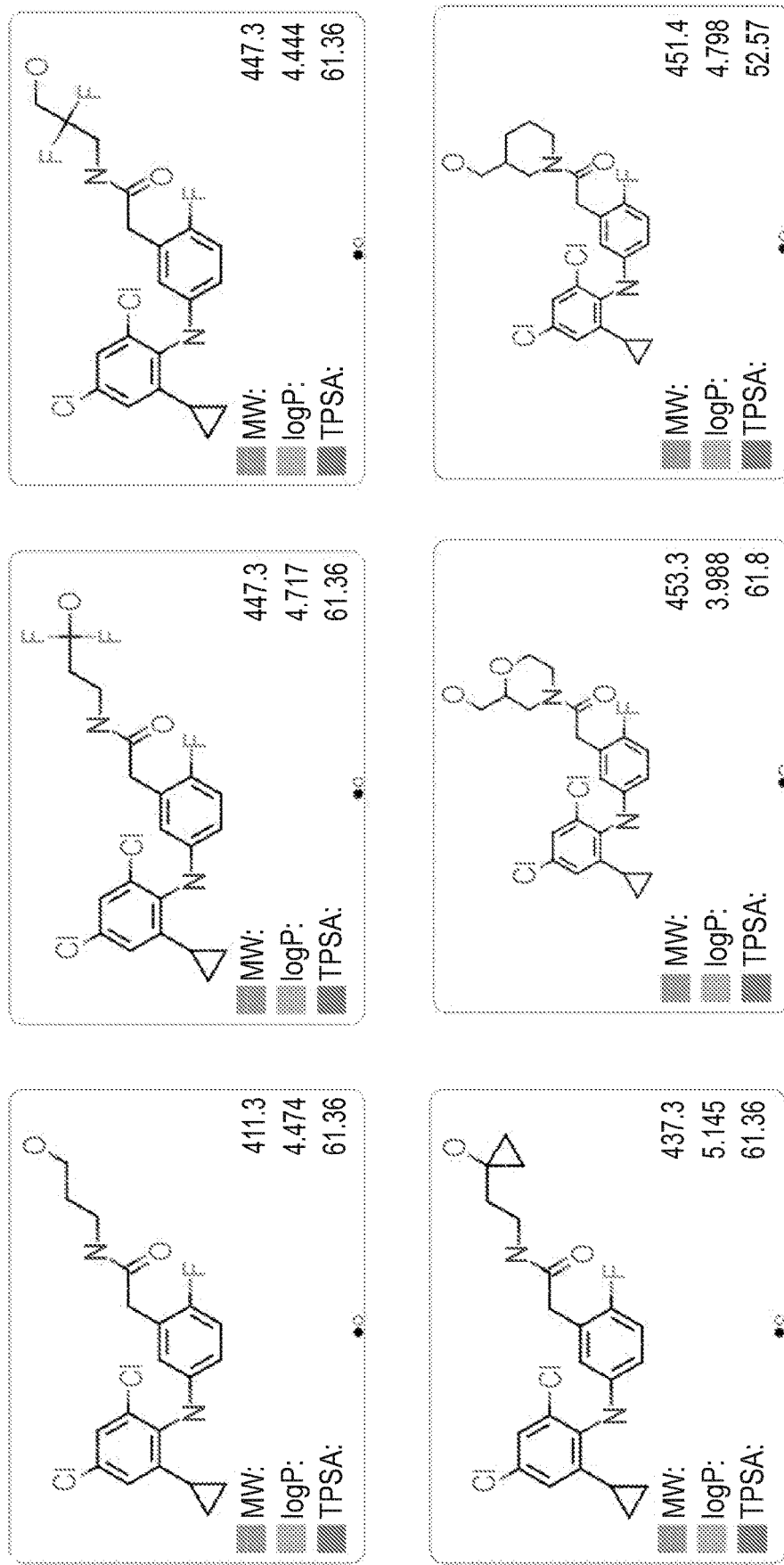
Figure 19:
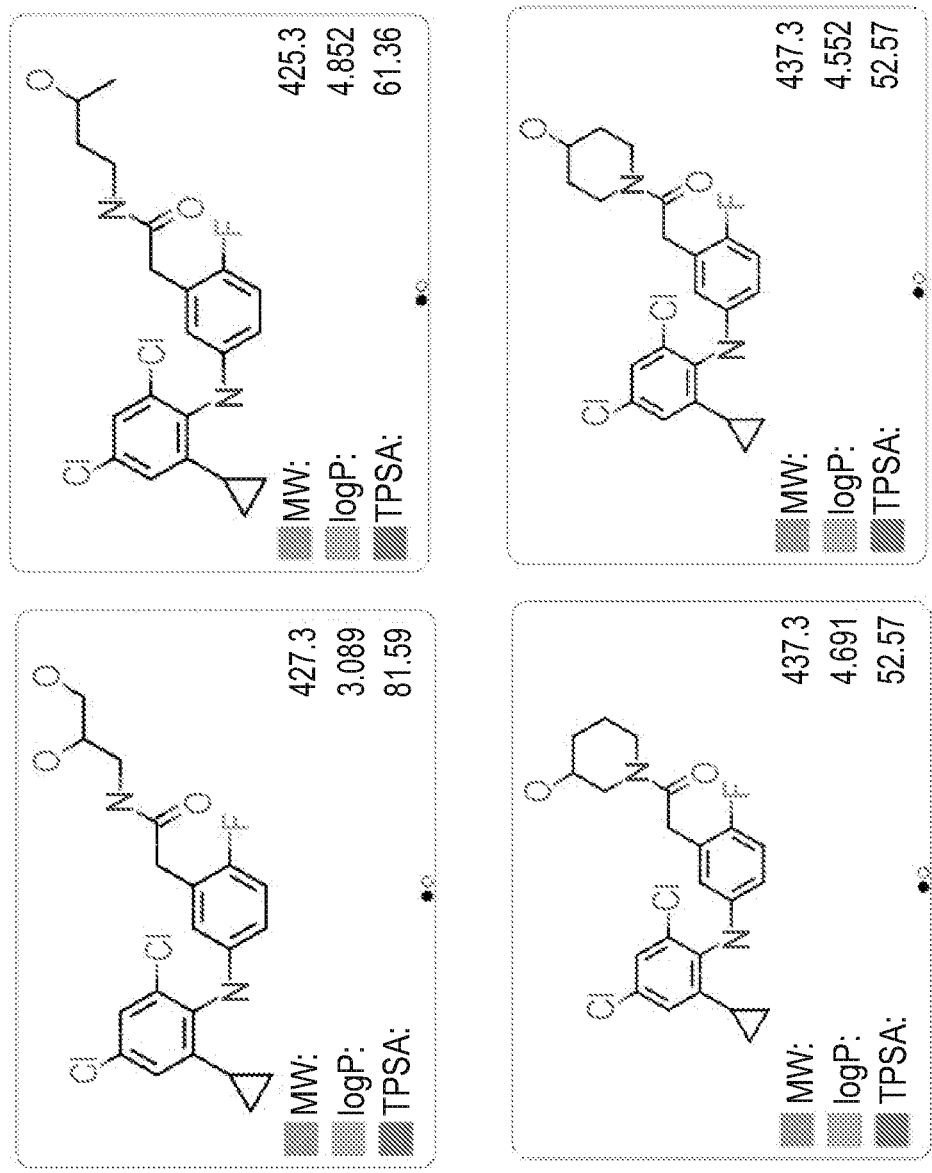

Exemplary compounds according to the present embodiments are presented in FIG. 19.

Exemplary compounds according to the present embodiments include compounds NH66, NH91, NH101, NH110, NH83.1, NH83.2, NH83.3, NH82.1, NH82.2, NH82.3 and NH160, as described herein.

Exemplary compounds according to the present embodiments include compounds NH91, NH101, NH110, NH83.1, NH83.2, NH83.3, NH82.1, NH82.2, and NH82.3, as described herein.

Exemplary compounds according to the present embodiments include compounds NH91, NH101, NH110, NH83.1, NH83.2, and NH83.3, as described herein.

Exemplary compounds according to the present embodiments include compounds NH91, NH101, and NH110, as described herein.

Exemplary compounds according to the present embodiments include compounds NH91 and NH101, as described herein.

The compounds of the present embodiments can be readily prepared by methods known in the art, typically by coupling one starting material that corresponds to ring B and one starting material that corresponds to ring A, in Formula I, while using, at suitable positions, reactive groups that can be coupled to one another and form the -D-$NR_1$-E- group.

The coupling can be performed such that the starting material that corresponds to ring B already comprises the V group as defined herein, or, alternatively, that starting material can comprise a corresponding ester or carboxylic acid instead of the amide, and coupling of a suitable amine to form the amide in V is performed after the coupling to the starting material that corresponds to ring A.

In some embodiments, when D and E are both absent, the starting material that corresponds to ring B includes an amine group at the respective position (metha to V), and the starting material that corresponds to ring A includes a leaving group, as defined herein, that can participate in a nucleophilic coupling reaction.

Exemplary synthetic pathways are described in the Examples section that follows.

For any of the embodiments described herein, and any combination thereof, the compound may be in a form of a salt, for example, a pharmaceutically acceptable salt.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or amide and/or a nitrogen atom in a heterocylic group) group of the compound which is in a positively charged form (e.g., wherein the basic group is protonated), in combination with at least one counter-ion, derived from the selected acid, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment, which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter, they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

According to an aspect of some embodiments of the present invention there is provided a pharmaceutical composition comprising the compound as described herein and a pharmaceutically acceptable carrier.

According to an aspect of some embodiments of the present invention there is provided a compound as described herein or a pharmaceutical composition as described herein, for use in modulating an activity of a voltage-dependent potassium channel.

According to an aspect of some embodiments of the present invention there is provided a method of modulating an activity of a voltage-dependent potassium channel, which comprises contacting the potassium channel with a compound or a pharmaceutical composition as described herein. The contacting can be effect in vitro, e.g., by contacting a cell, a tissue or an organ which express the channel with the compound or composition, or in vivo, by administering to a subject in need thereof a therapeutically effective amount of the compound or composition.

In some embodiments, the potassium channel is Kv7.2/7.3.

In some embodiments, the modulating comprises opening the potassium channel.

According to an aspect of some embodiments of the present invention there is provided a compound as described herein or a pharmaceutical composition as described herein, for use in modulating an activity of a TRPV1 channel.

According to an aspect of some embodiments of the present invention there is provided a method of modulating an activity of a TRPV1 channel, which comprises contacting the TRPV1 channel with a compound or a pharmaceutical composition as described herein. The contacting can be effect in vitro, e.g., by contacting a cell, a tissue or an organ which express the channel with the compound or composition, or in vivo, by administering to a subject in need thereof a therapeutically effective amount of the compound or composition.

In some embodiments, the modulating comprises inhibiting the activity of the TRPV1 channel (blocking the channel).

According to an aspect of some embodiments of the present invention there is provided a compound as described herein or a pharmaceutical composition as described herein, for use in modulating an activity of both a voltage-dependent potassium channel and a TRPV1 channel, as described herein in any of the respective embodiments.

According to an aspect of some embodiments of the present invention there is provided a method of modulating an activity of a voltage-dependent potassium channel and of a TRPV1 channel, which comprises contacting these channels with a compound or a pharmaceutical composition as described herein. The contacting can be effect in vitro, e.g., by contacting a cell, a tissue or an organ which express these channels with the compound or composition, or in vivo, by administering to a subject in need thereof a therapeutically effective amount of the compound or composition.

According to an aspect of some embodiments of the present invention there is provided a compound as described herein or a pharmaceutical composition as described herein, for use in treating a medical condition associated with an activity of a voltage-dependent potassium channel and/or of a TRPV1 channel.

According to an aspect of some embodiments of the present invention there is provided a compound as described herein or a pharmaceutical composition as described herein, for use in treating a medical condition associated with an activity of a voltage-dependent potassium channel and of a TRPV1 channel.

According to an aspect of some embodiments of the present invention there is provided a method of treating a medical condition associated with an activity of a voltage-dependent potassium channel and/or of a TRPV1 channel in a subject in need thereof, the method comprising administering to the subject a therapeutically effective amount of a compound or a pharmaceutical composition as described herein in any of the respective embodiments and any combination thereof.

According to some of any of the embodiments described herein, the medical condition is such that modulating an activity of one, and preferably both of a voltage-dependent potassium channel and a TRPV1 channel, as described herein, is beneficial.

According to some of any of the embodiments described herein, the medical condition is such that opening a voltage-dependent potassium channel and blocking (inhibiting) a TRPV1 channel, as described herein, is beneficial.

An exemplary medical condition is neuropathic pain.

Any other medical conditions (pathologies, conditions, diseases and/or disorders) that are associated with TRPV1 channel functioning and/or a voltage-dependent potassium channel as described herein are contemplated.

Exemplary medical conditions that are beneficially treatable by the TRPV1 inhibitors (blockers) described herein (compounds having general Formula I) include, but are not limited to, epilepsy, pain related conditions such as neurogenic pain, neuropathic pain, allodynia, pain associated with inflammation, and pain associated with pancreatitis, bipolar disorder, mood disorder, psychotic disorder, schizophrenia, anxiety and a motor neuron disease, bladder overactivity, urinary incontinence, persistent visceral hypersensitivity, including irritable bowel syndrome (IBD), chronic cough, and cancer (for example, squamous cell carcinoma, prostate carcinoma and pancreatic cancer).

There is much pathology, conditions and disorders that is associated with defective potassium channel functioning. Just as other potassium channel opening compounds, the compounds described herein are for use within the framework of a treatment for pathologies, conditions, disease and disorders associated with defective potassium channel functioning, so as to treat, ameliorate, prevent, inhibit, or limit the effects of the conditions and pathologies in animals including humans.

Exemplary medical conditions that are beneficially treatable by the potassium channel openers described herein include, but are not limited to, central or peripheral nervous system disorders such as ischemic stroke, migraine, ataxia, Parkinson's disease, bipolar disorders, trigeminal neuralgia, spasticity, mood disorders, brain tumors, psychotic disorders, schizophrenia, myokymia, neurogenic pain, neuropathic pain, seizures, epilepsy, hearing and vision loss, anxiety and motor neuron diseases. The compounds described herein can further be beneficially used as neuroprotective agents (e.g., to prevent stroke and the like). The compounds described herein are also useful in treating disease states such as gastroesophogeal reflux disorder and gastrointestinal hypomotility disorders.

The compounds disclosed herein can also be used as potent candidates for treating a variety of medical conditions wherein depressing the cortical and/or peripheral neuron activity is beneficial, such as, for example, epilepsy, ischemic stroke, migraine, ataxia, myokymia, neurogenic pain, neuropathic pain, Parkinson's disease, bipolar disorder, trigeminal neuralgia, spasticity, mood disorder, psychotic disorder, schizophrenia, brain tumor, hearing and vision loss, anxiety and a motor neuron disease.

According to an aspect of some embodiments of the present invention, the compound or the composition as described herein is for use in depressing a cortical and/or peripheral neuron activity and/or in treating a condition in which depressing a cortical and/or peripheral neuron activity in a subject is beneficial, as described herein.

As used herein a "pharmaceutical composition" refers to a preparation of one or more of the compounds of the present invention (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject.

The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations, which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions, which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

In some embodiments of the present invention, the amount of the composition to be administered required to achieve a therapeutic effect (e.g., a dosage or a therapeutically effective amount of the compound as described herein) is lower than an amount of previously described compounds known to exhibit the same therapeutic effect by at least 20%, or at least 30%.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an SRI of the invention formulated in a compatible pharmaceutical carrier may also be prepared, placed in an appropriate container, and labeled for treatment of a particular medical condition, disease or disorder, as is detailed hereinabove.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine, and/or an additional agent usable in treating a medical condition, disease or disorder as described herein.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it means that the group, in this case the alkyl group, may contain 1 carbon atom, 2 carbon atoms, 3 carbon atoms, etc., up to and including 20 carbon atoms. More preferably, it is a medium size alkyl having 1 to 10 carbon atoms. Most preferably, it is a lower alkyl having 1 to 4 carbon atoms. The alkyl group may be substituted or unsubstituted. When substituted, the substituent group can be, for example, cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or $NR_aR_b$, wherein $R_a$ and $R_b$ are each independently hydrogen, alkyl, cycloalkyl, aryl, carbonyl, sulfonyl, trihalomethysulfonyl and, combined, a five- or six-member heteroalicyclic ring.

A "haloalkyl" groups describes an alkyl, as defined herein, substituted by one or more halo substituents, as defined herein. In some embodiments, the haloalkyl is an alkyl substituted by two or more, or three of more, halo substituents. In some embodiments, each of the halo substituents is fluoro. In some embodiments, a haloalkyl is —$CF_3$ or —$CF_2H$.

A "cycloalkyl" group refers to an all-carbon monocyclic or fused ring (i.e., rings which share an adjacent pair of carbon atoms) group wherein one of more of the rings does not have a completely conjugated pi-electron system (an alicyclic ring). Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamyl, N-carbamyl, C-amido, N-amido, nitro, amino and $NR_aR_b$ as defined above.

An "alkenyl" group refers to an alkyl group, which consists of at least two carbon atoms and at least one carbon-carbon double bond.

An "alkynyl" group refers to an alkyl group, which consists of at least two carbon atoms and at least one carbon-carbon triple bond.

In some embodiments, whenever an alkyl substituent is indicated, it can be replaced by an alkynyl or an alkynyl, as defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $NR_aR_b$ as defined above.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino or $NR_aR_b$ as defined above.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $NR_aR_b$ as defined above.

As used herein, a "cyclic group" describes an alicyclic group (a cycloalkyl), an aryl, a heteroaryl or an heteroalicyclic.

A "hydroxy" group refers to an —OH group.

An "azido" group refers to a —N=N group.

An "alkoxy" group refers to both an —O-alkyl and an —O-cycloalkyl group, as defined herein.

A "haloalkoxy" group describes an O-alkyl group where the alkyl is a haloalkyl as described herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, cycloalkyl, aryl, heteroaryl (bonded through a ring carbon) or heteroalicyclic (bonded through a ring carbon) as defined herein.

An "aldehyde" group refers to a carbonyl group, where R' is hydrogen.

A "thiocarbonyl" group refers to a —C(=S)—R' group, where R' is as defined herein.

The term "carboxylate" encompasses C-carbocylate and O-carboxylate.

A "C-carboxy" group refers to a —C(=O)—O—R' groups, where R' is as defined herein.

An "O-carboxy" group refers to an R'C(=O)—O— group, where R' is as defined herein.

A "carboxylic acid" group refers to a C-carboxyl group in which R' is hydrogen.

A "halo" group refers to fluorine, chlorine, bromine or iodine.

A "trihalomethyl" group refers to a —$CX_3$ group wherein X is a halo group as defined herein.

A "trihalomethanesulfonyl" group refers to an $X_3CS(=O)_2$— group wherein X is a halo group as defined herein.

A "sulfinyl" group refers to an —S(=O)—R' group, where R' is as defined herein.

A "sulfonyl" group refers to an —S(=O)$_2$—R' group, where R' is as defined herein.

The term "sulfonylamide" encompasses S-sulfonylamide and N-sulfonylamido.

An "S-sulfonamido" group refers to a —S(=O)$_2$—NR'R" group, with R' is as defined herein and R" is as defined for R'.

An "N-sulfonamido" group refers to an R'S(=O)$_2$—NR" group, where R' and R" are as defined herein.

A "trihalomethanesulfonamido" group refers to an $X_3CS(=O)_2NR'$— group, where R' and X are as defined herein.

The term "carbamate" encompasses O-carbamyl and N-carbamyl.

An "O-carbamyl" group refers to an —OC(=O)—NR'R" group, where R' and R" are as defined herein.

An "N-carbamyl" group refers to an R'OC(=O)—NR"— group, where R' and R" are as defined herein.

The term "thiocarbamate" encompasses O-thiocarbamyl and N-thiocarbamyl.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —NR'R" group, where R' and R" are as defined herein.

An "alkylamino" group refers to an amine group is which one of R' and R" is alkyl (monoalkylamine) or in which both R' and R" are each independently an alkyl (dialkylamine).

The term "amide" encompasses C-amido and N-amido.

A "C-amido" group refers to a —C(=O)—NR'R" group, where R' and R" are as defined herein.

An "N-amido" group refers to an R'C(=O)—NR" group, where R' and R" are as defined herein.

A "quaternary ammonium" group refers to an —NHR'R"'+ group, wherein R' and R" are independently alkyl, cycloalkyl, aryl or heteroaryl.

An "ureido" group refers to an —NR'C(=O)—NR"R"' group, where R' and R" are as defined herein and R"' is defined as either R' or R".

A "guanidine" group refers to an —R'NC(=N)—NR"R"' group, where R', R" and R"' are as defined herein.

A "guanyl" group refers to an R'R"NC(=N)— group, where R' and R" are as defined herein.

A "nitro" group refers to an —NO$_2$ group.

A "cyano" group refers to a —C≡N group.

A "silyl" group refers to a —SiR'R"R"', where R', R" and R"' are as defined herein.

A "leaving group" as used herein and in the art describes a labile atom, group or chemical moiety that readily undergoes detachment from an organic molecule during a chemical reaction, while the detachment is typically facilitated by the relative stability of the leaving atom, group or moiety thereupon. Typically, any group that is the conjugate base of a strong acid can act as a leaving group. Representative examples of suitable leaving groups according to some of the present embodiments include, without limitation, trichloroacetimidate, acetate, tosylate, triflate, sulfonate, azide, halide (halo, preferably bromo or iodo), hydroxy, thiohydroxy, alkoxy, cyanate, thiocyanate, nitro and cyano.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Structure Activity Relation Study—Chemical Syntheses

The present inventors have designed and synthesized a library of nearly 50 di(aryl/heteroaryl)amine derivatives in order to screen these compounds for their activity in vitro on recombinant Kv7.2/3 and TRPV1 channels expressed in CHO cells.

The compounds library was designed based on general Formula A:

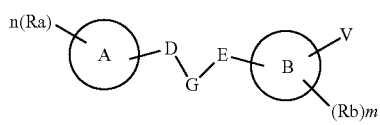

Formula A wherein:

A and B are each independently selected from an aryl and a heteroaryl;

D and E are each independently (CRdRe)u, wherein Rd and Re are each independently hydrogen, alkyl, cycloalkyl, haloalkyl, halo, etc., and u is independently 0 or 1 (preferably Rd and Re are each hydrogen);

n is an integer of from 1 to 5;

m is an integer of from 0 to 5;

Ra and Rb as defined for Formula I or are each independently selected from alkyl, cycloalkyl, halo, haloalkyl, haloalkoxy, alkoxy, aryl, aryloxy, hydroxy, amine, alkylamine, thiohydroxy, thioalkoxy, thioaryloxy, cyano, carboxylate, amide, carbamate, sulphonyl, and sulphonamide, (preferably from hydrogen, alkyl, halo, haloalkyl and haloalkoxy), wherein when n is greater than 1, each substituent Ra is the same or different and when m is greater than 2, each substituent Rb is the same or different;

G is selected from NR$_1$ and O;

R$_1$ is hydrogen, alkyl, cycloalkyl or aryl (preferably hydrogen); and

V is (CR$_2$R$_3$)k-C(=O)—NR$_4$—Z, and is at the ortho, meta or para position with respect to G, wherein:

k is an integer of from 0 to 2;

R$_2$ and R$_3$ are each independently selected from hydrogen, halo, alkyl, cycloalkyl, and aryl (preferably hydrogen or alkyl);

R$_4$ is hydrogen, alkyl, cycloalkyl, or aryl (preferably hydrogen, or an alkyl that forms a heteroalicyclic ring with R$_5$, R$_6$, R$_7$ and R$_8$, as described below); and Z is represented by Formula II:

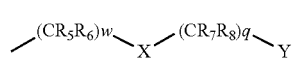

Formula II wherein:

w and q are each independently an integer of from 0 to 8, or from 0 to 6, or from 0 to 4, provided that w+q equals at least 2 (e.g., 2, 3 or 4);

X is selected from O and NR$_9$, or is absent;

Y is selected from OR$_{10}$, SR$_{10}$ and NR$_{10}$R$_{11}$;

R$_5$, R$_6$, R$_7$ and R$_8$ are each independently selected from hydrogen, halo, alkyl, cycloalkyl, heteroalicyclic, aryl, alkylamino, alkoxy, and aryloxy (preferably hydrogen or alkyl), or, alternatively, two of R$_5$, R$_6$, R$_7$, R$_8$ and R$_9$ form together an alicyclic or heteroalicyclic ring; and R$_{10}$ and R$_{11}$ are each independently hydrogen or alkyl, or, alternatively, two of R$_5$, R$_6$, R$_7$, R$_8$, R$_9$, R$_{10}$ and R$_{11}$ form together an alicyclic or heteroalicyclic ring.

The library was designed such that the screened compounds differ from one another by one or more of the following structural features:

The position of variable V with respect to G;

The nature of G;

The presence or absence or D and/or E;

The number and nature of the Ra substituent(s) and the position thereof;

The presence or absence of the Rb substituent(s) and the nature and position thereof;

The nature of the A and B rings; and

The chemical structure of the variable V.

Figure 20:
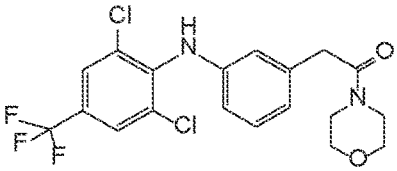
FIG. 20 presents the chemical structures and molecular weights of compounds tested in the screening assay as described in Examples 1 and 2 hereinbelow.
Figure 20:
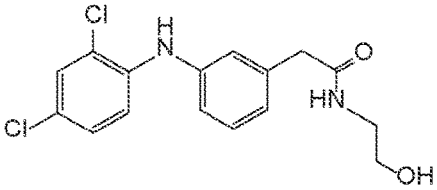
Figure 20:
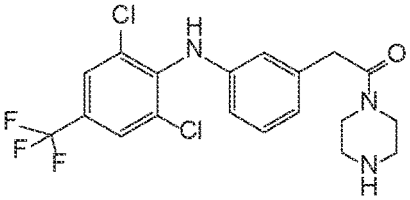
Figure 20:
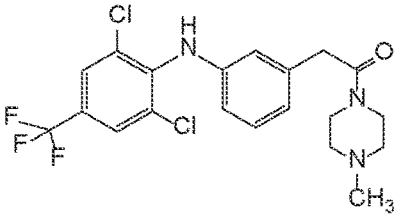
Figure 20:
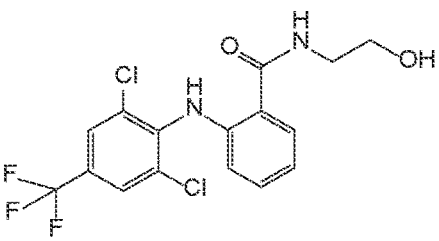
Figure 20:
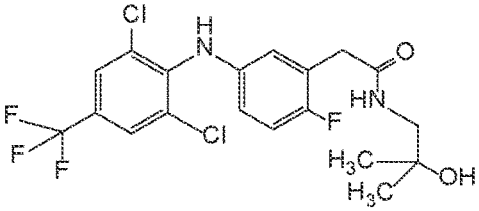

The chemical structures of exemplary compounds in the designed library are presented in FIG. 20.

As can be seen, most compounds feature phenyl rings as the A and B rings; the D and E groups are absent, and G is NR₁, with R₁ being hydrogen. Such compounds are also referred to herein as diphenylamine compounds or derivatives.

Figure 1B:
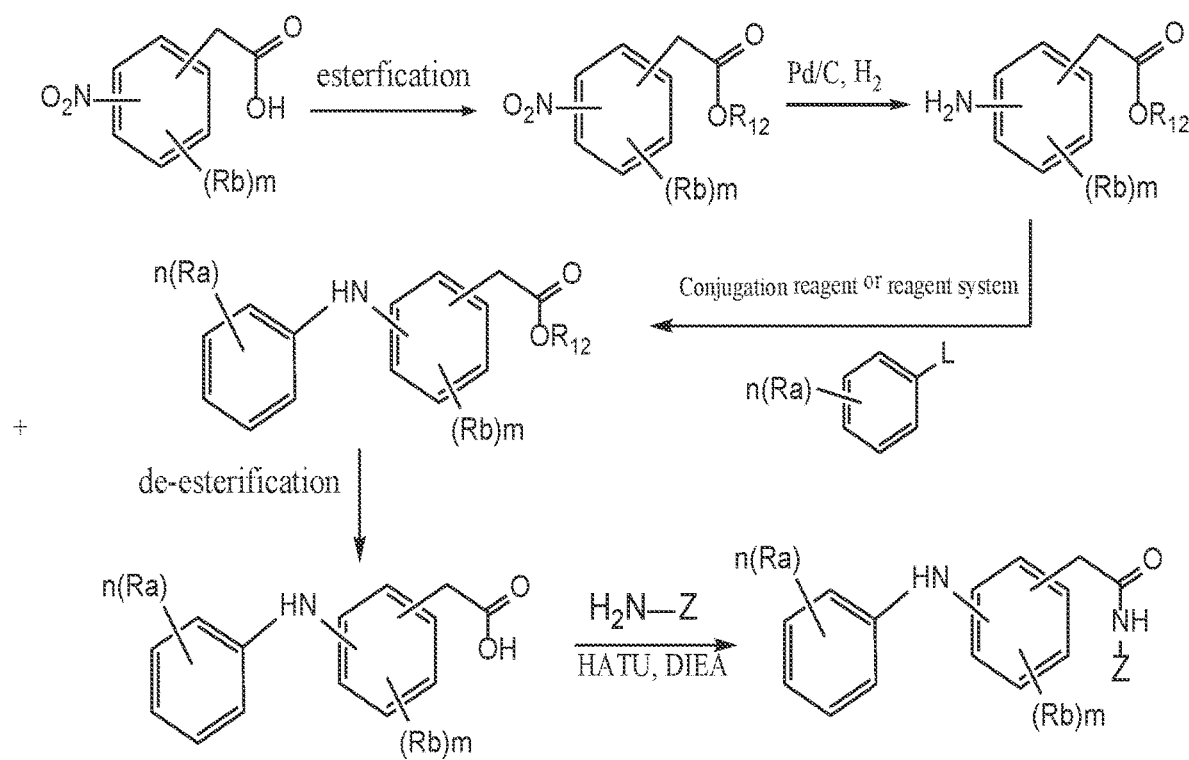

FIGS. 1A-B present exemplary general synthetic pathways used for preparing diphenylamine derivatives as presented in FIG. 20.

In FIG. 1A, an exemplary synthetic pathway starts by coupling a respective amine to a carboxylic acid derivative of a phenyl substituted by (Rb)m as defined in Formula A and further by a nitro group at a position respective to the position of group NR1 with respect to variable V is Formula A (e.g., ortho or metha). Any reagent or reagent system usable in forming an amide bond can be used for effecting this coupling. An exemplary, non-limiting reagent is HATU, but any other coupling reagent or reagent system (e.g., for peptide coupling) is contemplated. The synthesis proceeds to converting the nitro group to an amine group, using a reducing agent or system. An exemplary reducing system comprises hydrogen gas, Pd/C and optionally an alcoholic solvent such as methanol, however, any other reducing agent or system suitable for converting nitro to amine is contemplated. The synthesis then proceeds to coupling the respective amine with a phenyl ring substituted by (Ra)n as defined for Formula A, further substituted by a leaving group (denoted as L in FIG. 1A). The coupling is effect by a nucleophilic reaction, in the presence of suitable coupling reagent or system as known in the art. An exemplary system comprises Pd(dba)₃, Xant-phos, K₂CO₃, dioxane, and heat (e.g., microwave heating at 160° C.), however, any other reagent or reagent system is contemplated.

In FIG. 1B, an exemplary synthetic pathway starts by esterification of a carboxylic acid derivative of a phenyl substituted by (Rb)m as defined in Formula A and further by a nitro group at a position respective to the position of group NR1 with respect to variable V is Formula A (e.g., ortho or metha). Any reagent or reagent system usable in esterification is contemplated. An exemplary esterification is performed using an acid such as sulfuric acid. The synthesis proceeds by reducing the nitro group to an amine group and coupling the obtained amine with a phenyl ring substituted by (Ra)n as defined for Formula A, further substituted by a leaving group, as described for FIG. 1A. This is followed by de-esterification of the formed compound using methods and reagents known in the art and coupling the obtained carboxylic acid with a respective amine to form the amide of variable V is Formula A, as described for FIG. 1A.

By selecting starting materials and reagents featuring certain substituent(s) on the aryl rings (corresponding to variables Ra and Rb in Formula A) and/or of the amide (corresponding to variable V in Formula A), respective diphenylamine compounds of Formula A were prepared.

Figure 2:
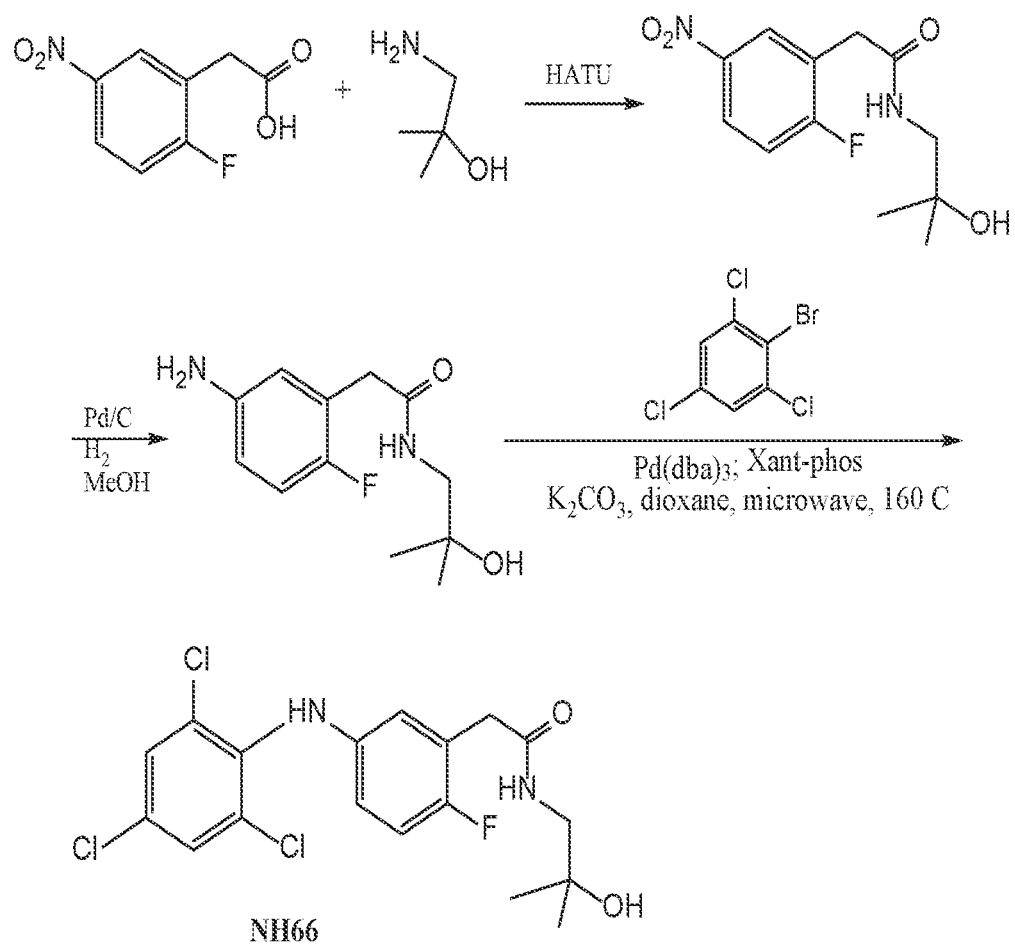
FIG. 2 presents an exemplary synthesis of NH66.
Figure 3:
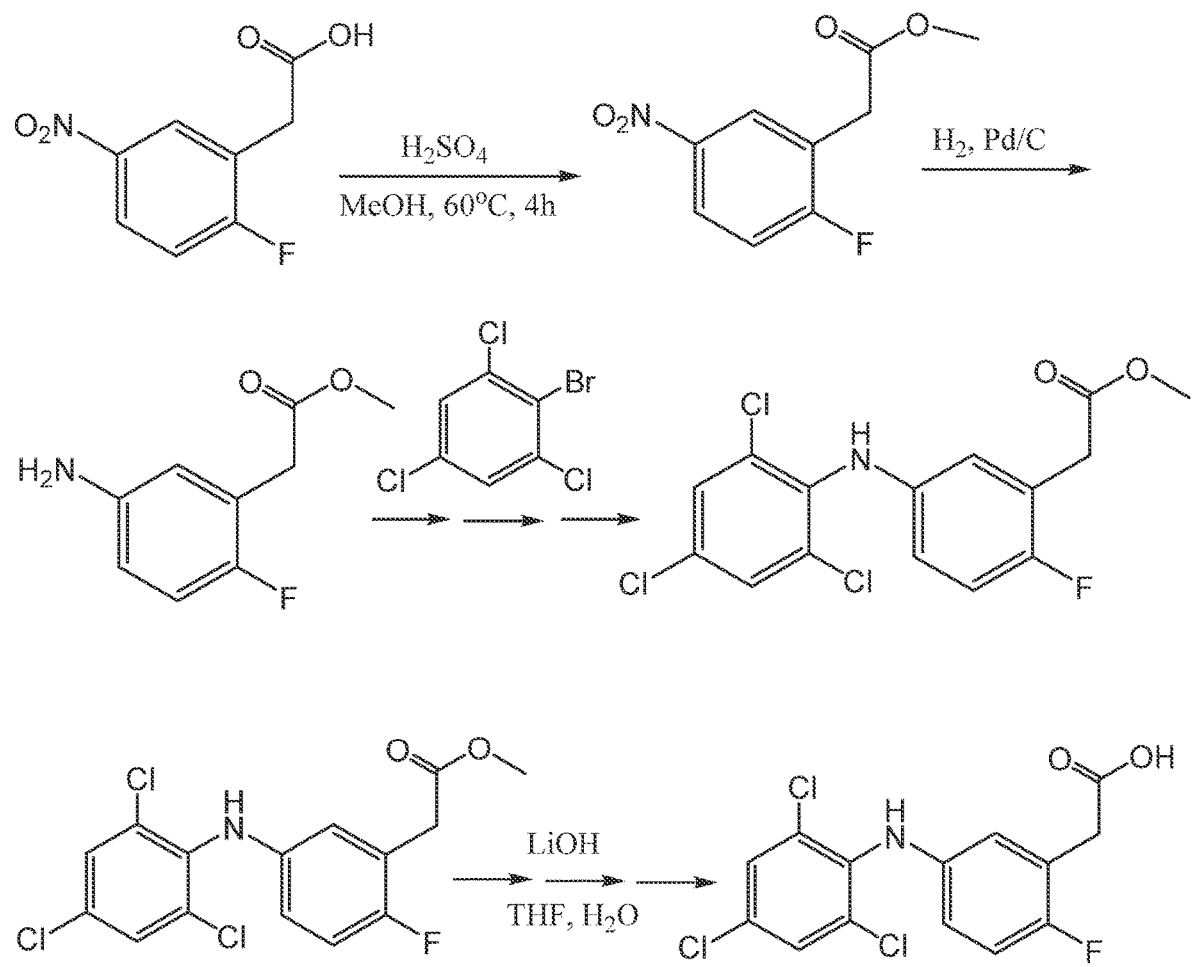
FIG. 3 presents exemplary syntheses of NH82 and NH83.
Figure 3:
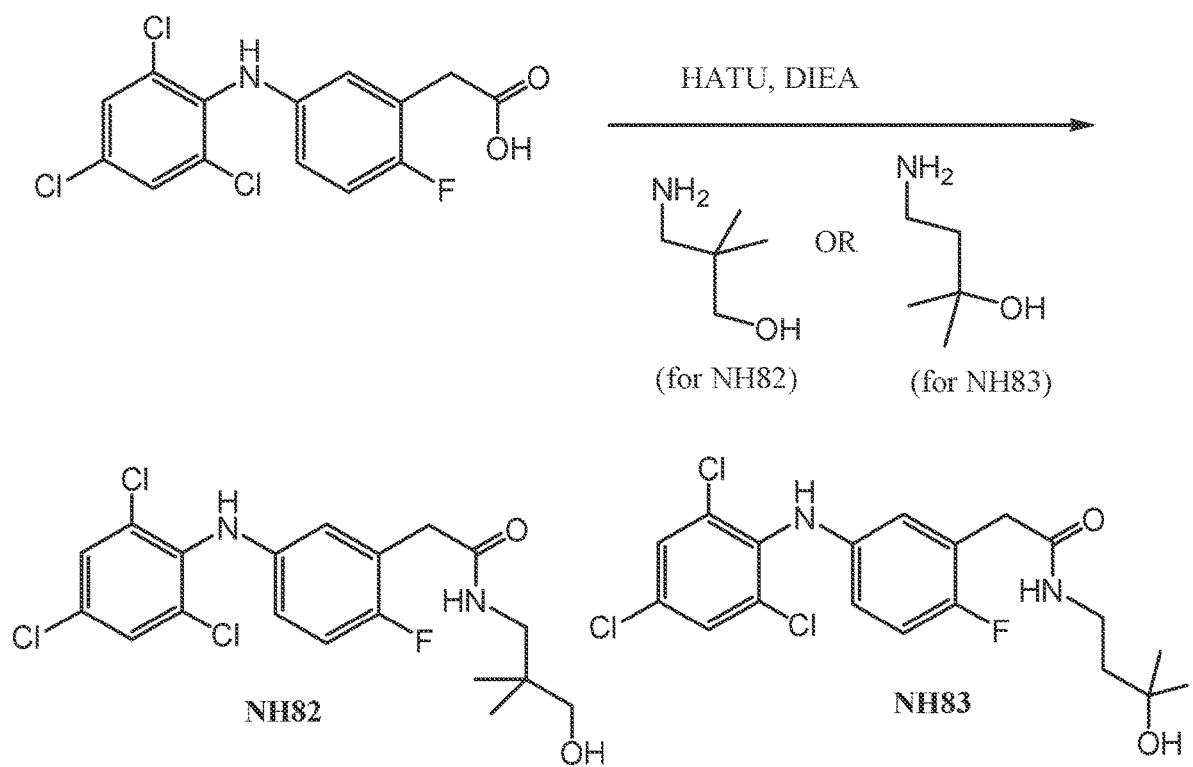
Figure 4:
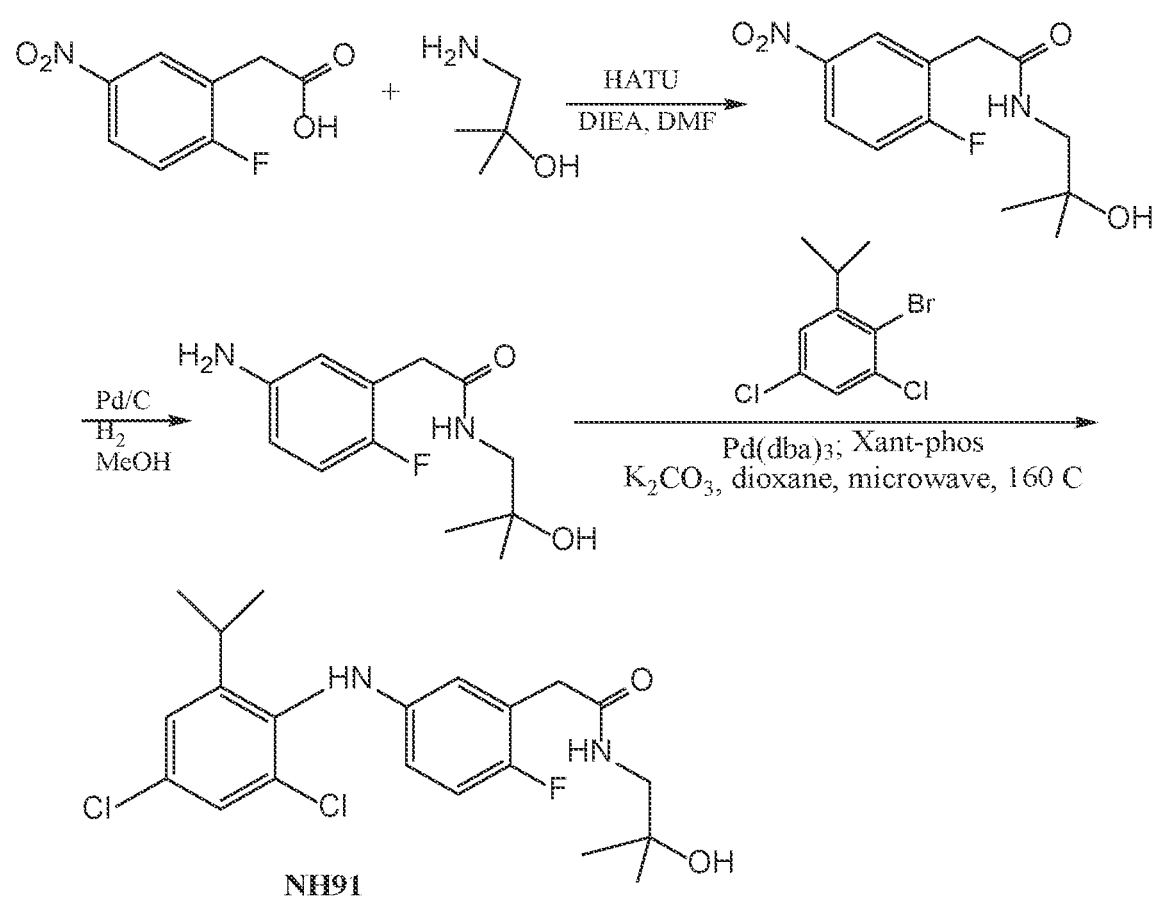
FIG. 4 presents an exemplary synthesis of NH91.
Figure 5:
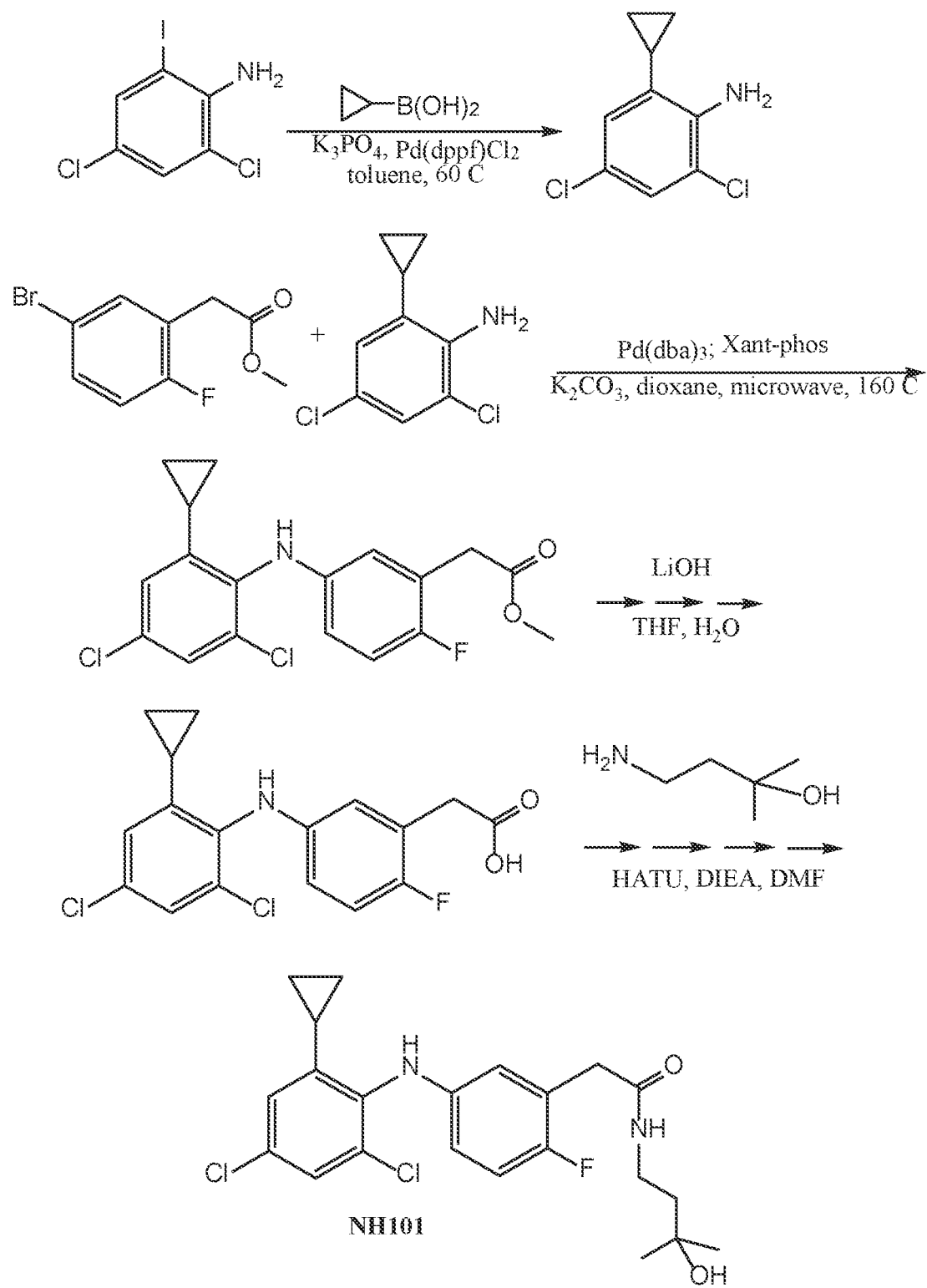
FIG. 5 presents an exemplary synthesis of NH101.
Figure 6:
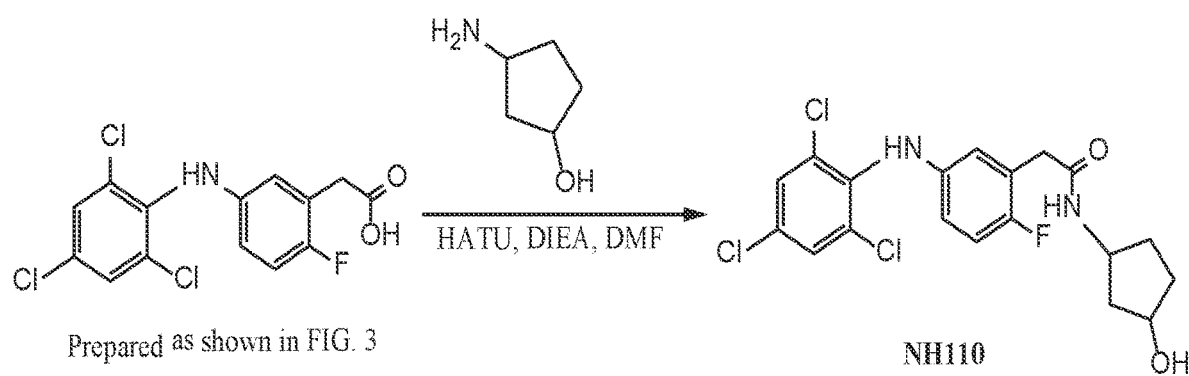
FIG. 6 presents an exemplary synthesis of NH110.

FIGS. 2-6 present exemplary syntheses of representative diphenylamine derivatives: NH66 (FIG. 2); NH82 and NH82 (FIG. 3); NH91 (FIG. 4), HN101 (FIG. 5) and NH110 (FIG. 6).

Using similar synthetic pathways, the following compounds are prepared:

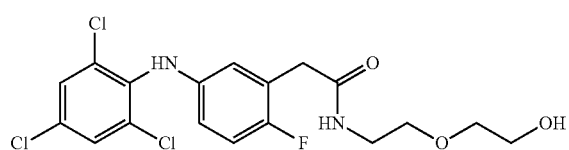

NH82.1

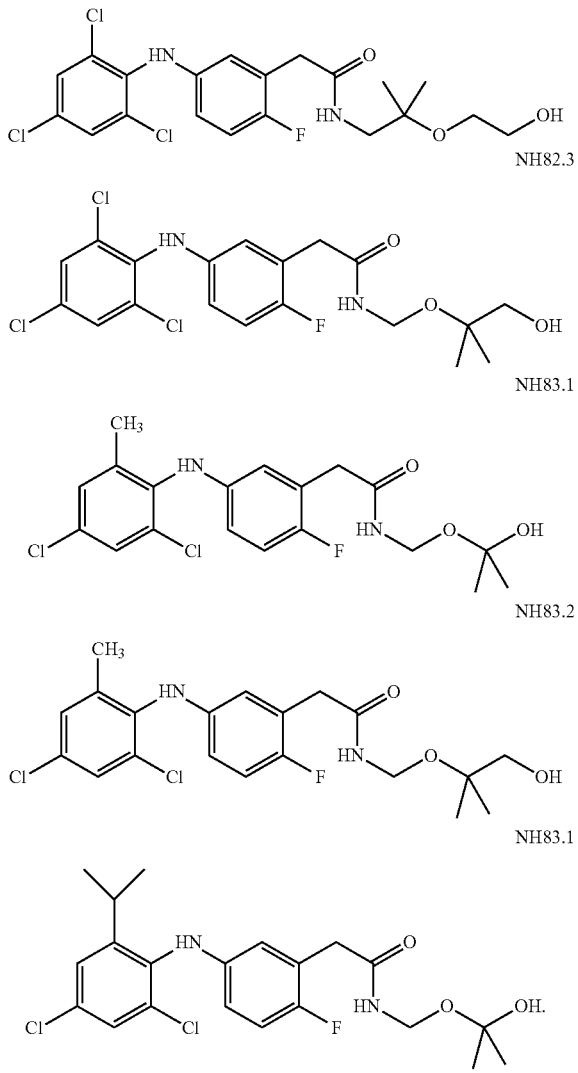

NH82.2

NH82.3

NH83.1

NH83.2

NH83.1

Compounds featuring a heteroaryl as one of rings A and B in Formula A and/or a variable G other than NH and/or variables D and/or E which are present were prepared by slightly modifying these pathways.

Figure 7:
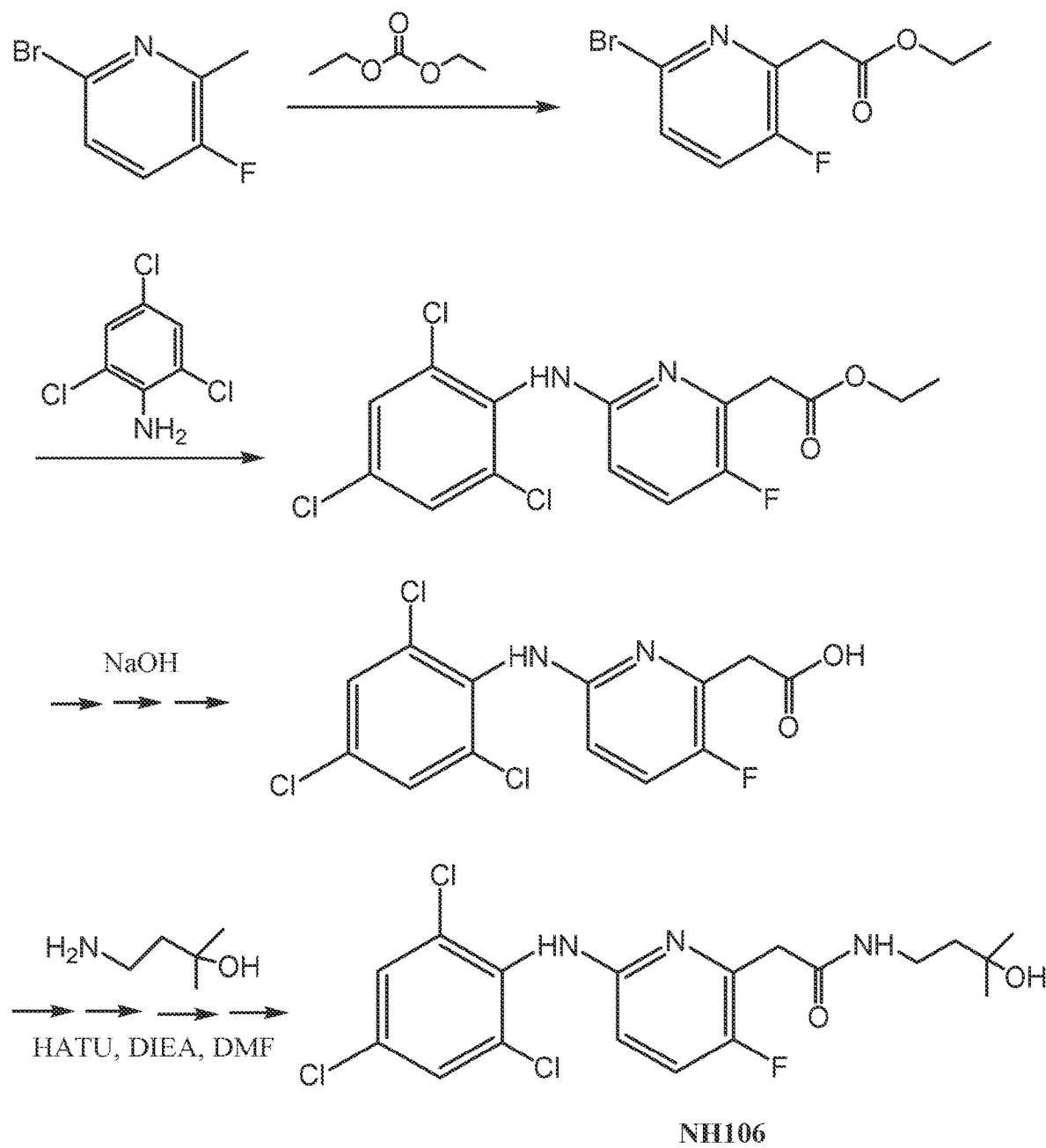
FIG. 7 presents an exemplary synthesis of NH106.

FIG. 7 presents a synthetic pathway for preparing an exemplary compound featuring a heteroaryl as ring B, denoted NH106.

Example 2

Structure Activity Relation Study

The dual activity of the compounds described in Example 1 in modulating the potassium Kv7.2/3 and the TRPV1 channels was tested using the following protocols:

Chinese hamster ovary CHO cells were grown in Dulbecco's modified Eagle's medium supplemented with 2 mM glutamine, 10% fetal calf serum, and antibiotics. In brief, 40,000 cells seeded on poly-D-lysine-coated glass coverslips (13 mm in diameter) in a 24-multiwell plate were transfected with pIRES-CD8 (0.3 μg) as a marker for transfection with 0.5 μg Kv7.2 and 0.5 μg Kv7.3. Transfection was performed using 3.6 µl of X-tremeGENE 9 (Roche) according to the manufacturer's protocol. For electrophysiology, transfected cells were visualized approximately 40 h after transfection, using the anti-CD8 antibody coated beads method.

For Kv7.2 potassium current recordings, the patch pipettes were pulled from borosilicate glass (Warner Instrument Corp) with a resistance of 3-7 MΩ, and were filled with (in mM): 130 KCl, 5 Mg ATP, 5 EGTA, 10 HEPES, pH 7.3 (adjusted with KOH), and sucrose was added to adjust osmolarity to 290 mOsmol. The external solution contained (in mM): 140 NaCl, 4 KCl, 1.2 MgCl2, 1.8 CaCl2, 11 glucose, 5.5 HEPES, pH 7.3 (adjusted with NaOH), and sucrose was added to adjust osmolarity to 310 mOsmol. Cells were held at −90 mV and stepped for 1.5 s from −70 mV to +30 mV in 10 mV increments and repolarized at −60 mV. For TRPV1 current recordings, the solutions were the same as those used for Kv7.2, except that the extracellular solution contained no $CaCl_2$ to limit desensitization and included 1 mM EGTA and 1 mM $MgCl_2$.

Following analysis of the obtained data, some structural features that render certain di(aryl/heteroaryl)amine derivatives as potential drugs that exhibit a dual channel targeting, activating Kv7.2 and inhibiting TRPV1 were identified, as follows:

Having an amide substituent (variable V in Formula A) of an aryl/heteroaryl ring B of Formula A at the meta position to the group bridging the two aryl/heteroaryl rings (variable G in Formula A);

Introducing an alkyl or cycloalkyl functionality (as one or more of $R_5$, $R_6$, $R_7$ and $R_8$) to a hydroxyalkyl or alkylene glycol substituent of the amide (variable Z in Formula A);

Introducing an alkyl or cycloalkyl substituent (as an Ra substituent) at the ortho position with respect to group G of an aryl/heteroaryl ring not bearing the amide substituent (ring A in Formula A); and/or Introducing a halo (e.g., fluoro) substituent (as an Rb substituent) to ring B of Formula A at an ortho position with respect to the amide substituent (variable V in Formula A).

In addition, compounds other than diphenylamine derivatives as defined herein, featuring other groups for variables A, B, D, E and G in Formula A, were shown to be inferior to diphenylamine derivatives.

The following compounds were found to be the most potent in exhibiting a dual channel targeting, activating Kv7.2 and inhibiting TRPV1 (see, FIG. 20): NH66, NH82, NH83, NH91, NH101 and NH110, and were subjected to further comparative studies.

Example 3

Activity Assays

Chinese hamster ovary CHO cells were grown in Dulbecco's modified Eagle's medium supplemented with 2 mM glutamine, 10% fetal calf serum, and antibiotics. In brief, 40,000 cells seeded on poly-D-lysine-coated glass coverslips (13 mm in diameter) in a 24-multiwell plate were transfected with pIRES-CD8 (0.3 µg) as a marker for transfection with 0.5 µg of Kv7.2 and Kv7.3 cDNA plasmids. Transfection was performed using 3.6 µl of X-tremeGENE 9 (Roche) according to the manufacturer's protocol. For electrophysiology, transfected cells were visualized approximately 40 h after transfection, using the anti-CD8 antibody coated beads method. Recordings were performed using the whole cell configuration of the patch clamp technique. Signals were amplified using an Axopatch 200B patch-clamp amplifier (Axon Instruments), sampled at 5 kHz and filtered at 2.4 kHz via a four pole Bessel low pass filter. Data were acquired using pClamp 10.5 software in conjunction with a DigiData 1440A interface. The patch pipettes were pulled from borosilicate glass (Harvard Apparatus) with a resistance of 3-7 megaohms. The intracellular pipette solution contained 130 mM KCl, 5 mM K2-ATP, 5 mM EGTA (or 5 mM BAPTA when indicated), 10 mM HEPES, pH 7.3 (adjusted with KOH), CaCl2 (as needed for different values of free Ca2+ concentration according to MAXCHELATOR software, with sucrose added to adjust osmolarity to 290 mosmol. The external solution contained 140 mM NaCl, 4 mM KCl, 1.8 mM CaCl2, 1.2 mM MgCl2, 11 mM glucose, 5.5 mM HEPES, adjusted with NaOH to pH 7.3 (310 mOsM). Series resistances were compensated (75-90%) and periodically monitored. Data analysis was performed using the Clampfit program (pClamp 10.5; Axon Instruments), Microsoft Excel (Microsoft, Redmond, Wash.), and Prism 5.0 (GraphPad Software, Inc., San Diego, Calif.). Leak subtraction was performed off-line, using the Clampfit program of the pClamp 10.5 software. Cells were held at −90 mV, were stepped from −70 mV to +30 mV in 10 mV increments and repolarized at −60 mV.

The normalized conductance was plotted as a function of the test voltages, for cells in the absence and presence of the drug. Chord conductance (G) was calculated by using the following equation: G=I/(V−Vrev), where I corresponds to the current amplitude measured at the end of the pulse, and Vrev is the calculated reversal potential assumed to be −90 mV in CHO cells. G was estimated at various test voltages (V) and then normalized to a maximal conductance value, Gmax. Activation curves were fitted by one Boltzmann distribution: G/Gmax=1/{1+exp[(V50−V)/s]}, where V50 is the voltage at which the current is half-activated and s is the slope factor.

Inhibition of recombinant TRPV1 channel was tested as described in Example 2 hereinabove.

TRPV1 whole-cell currents were activated by exposing transfected CHO cells to 0.5 µM capsaicin at a holding potential of −60 mV.

Cardiac channel Herg current recordings were performed as follows:

Cells were held at −90 mV and stepped for 1.5 s from −70 mV to +30 mV in 10 mV increments and repolarized at −60 mV.

Inhibition of the evoked spike discharge of nociceptive dorsal root (DRG) sensory neurons was tested as follows:

For current-clamp recordings in DRG neurons, the patch pipettes were filled with (in mM): 135 KCl, 1 $K_2ATP$, 1 MgATP, 2 EGTA, 1.1 $CaCl_2$, 5 glucose (free $[Ca^{2+}]_i$=87 nM), 10 HEPES, adjusted with KOH at pH 7.4 (315 mOsm). The external solution contained (in mM): 150 NaCl, 2.5 KCl, 2 $CaCl_2$, 2 $MgCl_2$, 15 glucose, 10 HEPES, adjusted with NaOH at pH 7.4 (325 mOsm). Drug exposure was evoked by rapid application using a fast perfusion system (AutoMate Scientific).

Figure 8B:
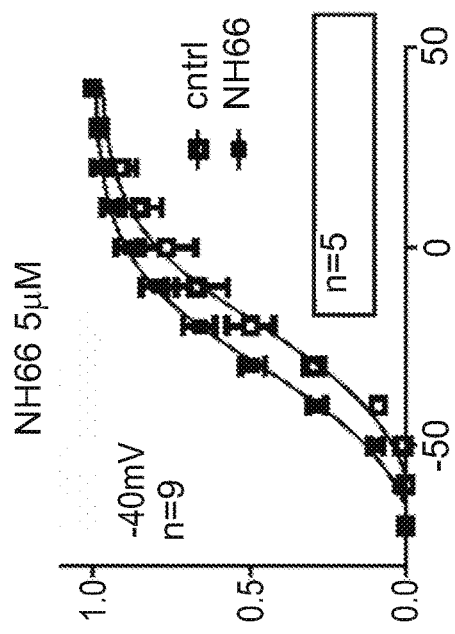
FIGS. 8A-C present comparative plots showing the effect of 5 μM NH66 on the amplitude (FIG. 8A) and the voltage-dependence (FIG. 8B) of recombinant Kv7.2/3 currents, and the effect of the previously described diphenylamine compound NH43 (FIG. 8C).
Figure 8A:
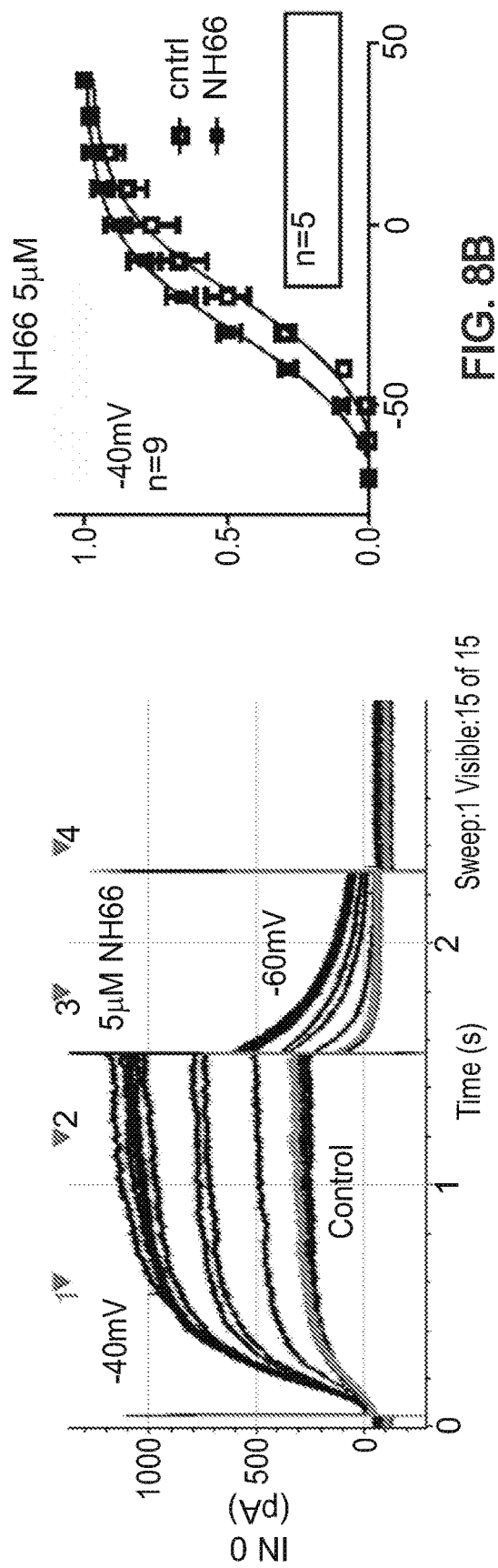
Figure 8C:
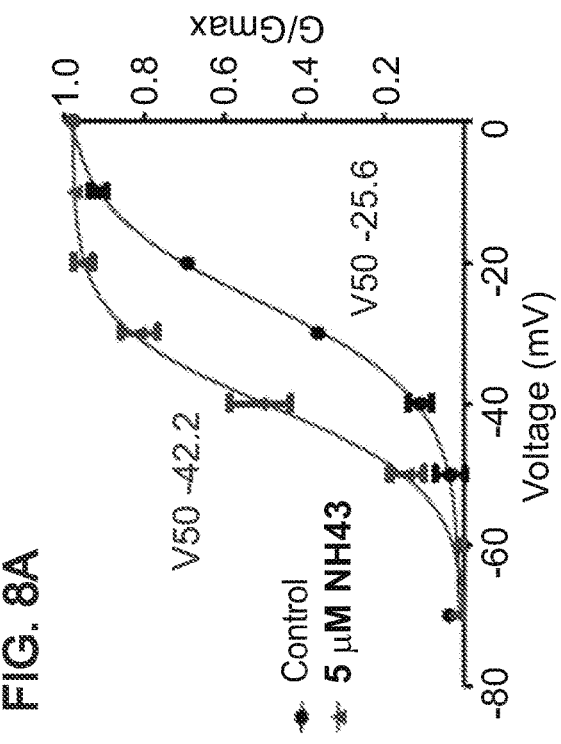

Results:

FIGS. 8A-C present the effect of 5 µM NH66 on the amplitude (FIG. 8A) and the voltage-dependence of recombinant Kv7.2/3 currents, and the effect of the previously described diphenylamine compound NH43 (FIG. 8C).

As shown therein, at 5 µM, NH43 and NH66 increase the amplitude of recombinant Kv7.2/3 currents expressed in CHO cells by about 3.5-fold at −40 mV and left-shift their voltage-dependence by more than −10 mV.

Figure 9:
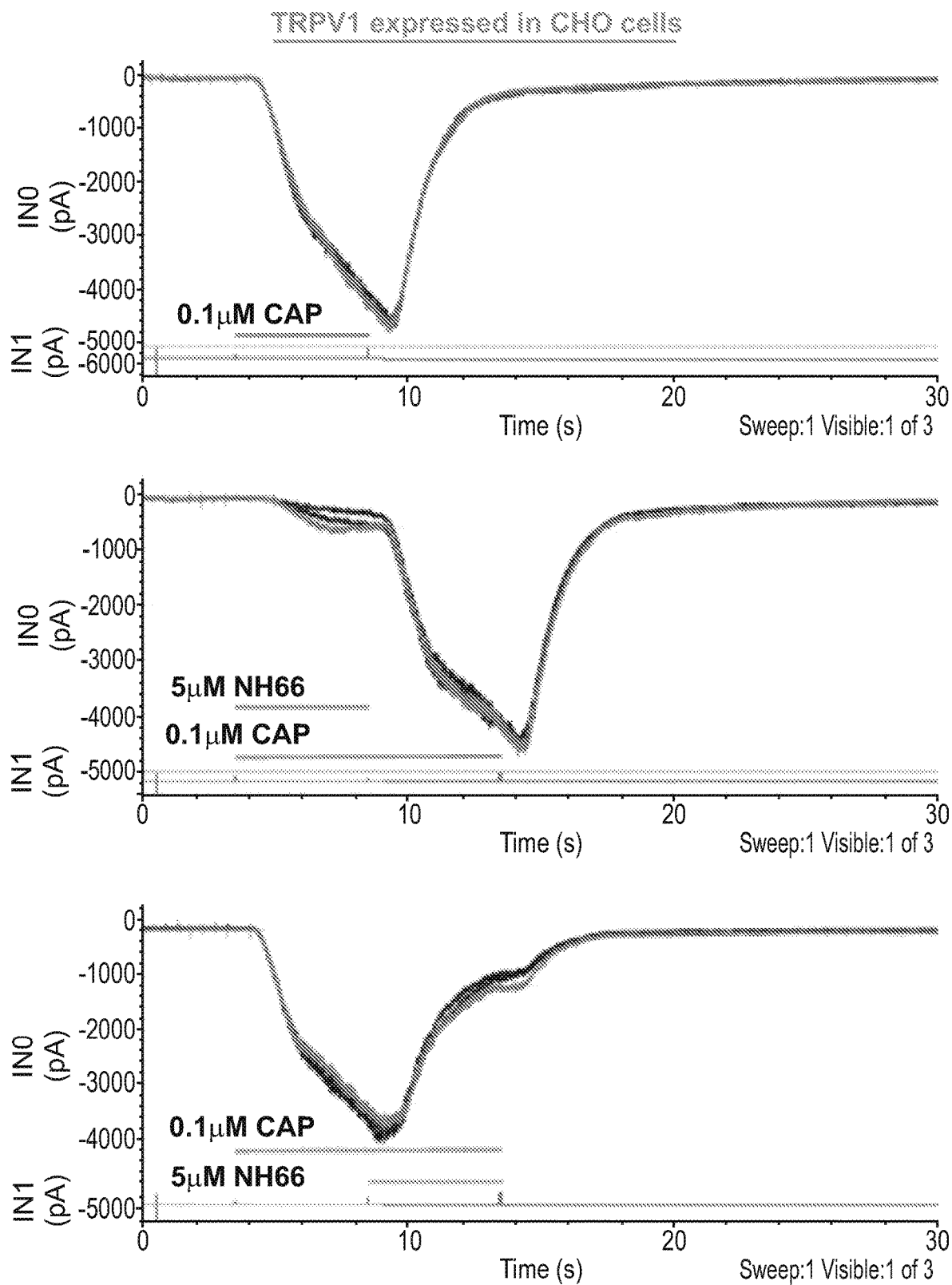
FIG. 9 presents plots showing the effect of 5 μM NH66 on recombinant TRPV1 currents activated by 0.1 μM capsaicin (CAP).

FIG. 9 presents the effect of 5 µM NH66 on recombinant TRPV1 currents activated by 0.1 µM capsaicin (CAP). In FIG. 9 are shown the TRPV1 currents evoked by application of 0.1 μM capsaicin to transfected CHO cells. In the upper panel are shown the currents only evoked by application of 0.1 μM capsaicin; in the middle panel, are shown the currents first evoked by application of 0.1 μM capsaicin+5 μM NH66, then by 0.1 μM capsaicin only. The lower panel shows currents evoked first by 0.1 μM capsaicin, then by 0.1 μM capsaicin+5 μM NH66.

As shown therein, like NH43, NH66 inhibits the recombinant TRPV1 currents activated by 0.1 μM capsaicin with an $IC_{50}$ of 0.3 μM.

Figure 10A:
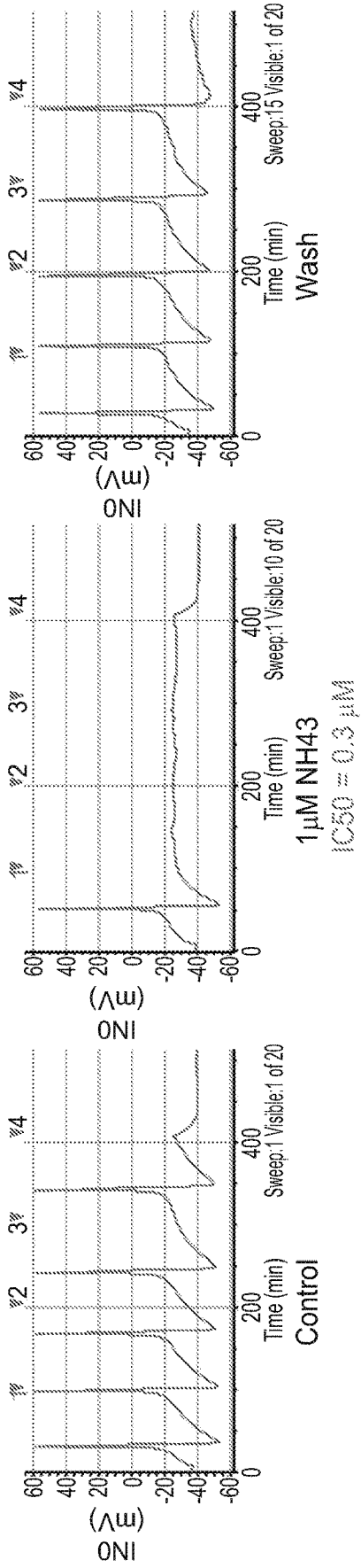
FIGS. 10A-B present plots showing the effect of 1 μM NH43 (FIG. 10A) and 1 μM NH66 (FIG. 10B) on evoked spike discharge of rat DRG neurons.
Figure 10B:
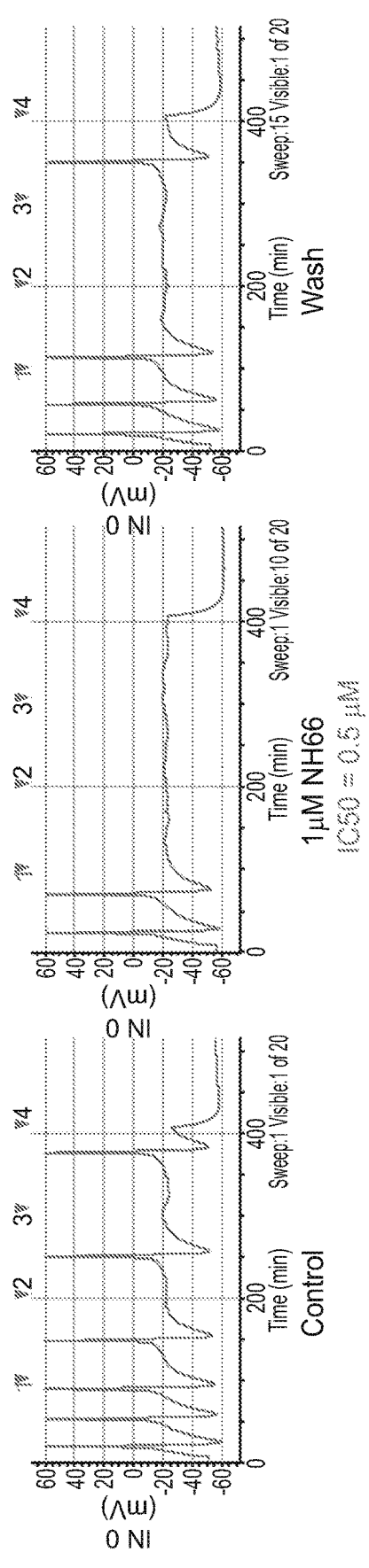

FIGS. 10A-B present the effects of 1 μM NH43 (FIG. 10A) and 1 μM NH66 (FIG. 10B) on evoked spike discharge of rat DRG neurons.

As shown therein, NH43 and NH66 inhibit the evoked spike discharge of nociceptive dorsal root (DRG) sensory neurons with $IC_{50}$s of 0.3 μM and 0.5 μM, respectively.

Figure 11A:
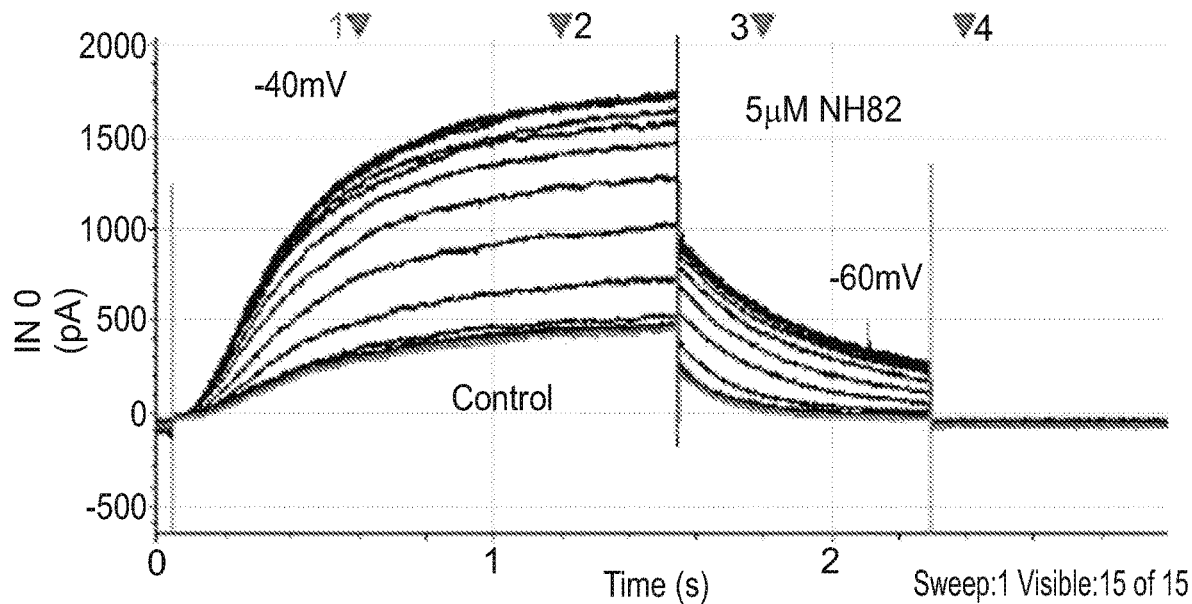
FIGS. 11A-D present comparative plots showing the effect of NH82 on the amplitude (FIG. 11A) and voltage-dependence (FIG. 11B) of recombinant Kv7.2/3, and the effect of NH82 (FIG. 11C) and NH83 (FIG. 11D) on DRG evoked spike discharge.
Figure 11B:
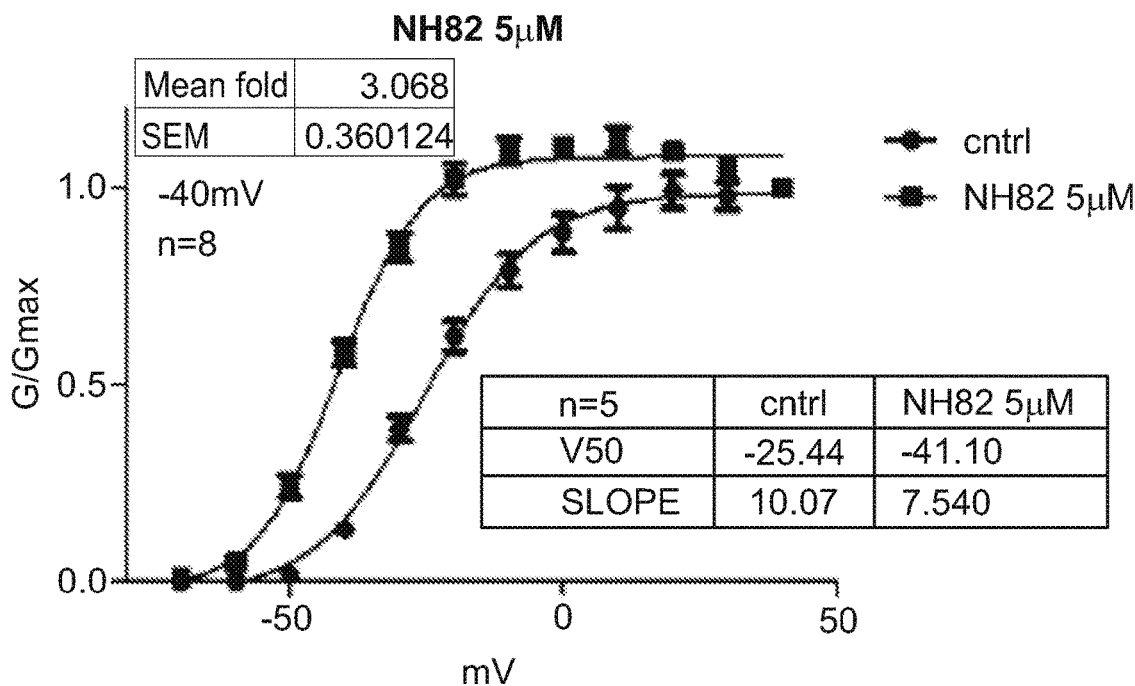

FIGS. 11A-B present the effect of NH82 on the amplitude (FIG. 11A) and voltage-dependence (FIG. 11B) of recombinant Kv7.2/3.

Figure 11C:
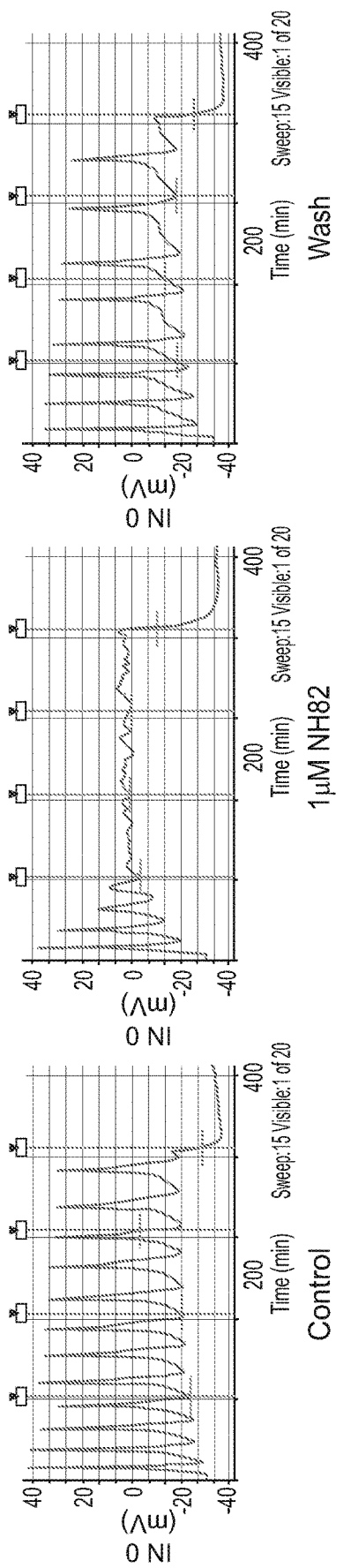
Figure 11D:
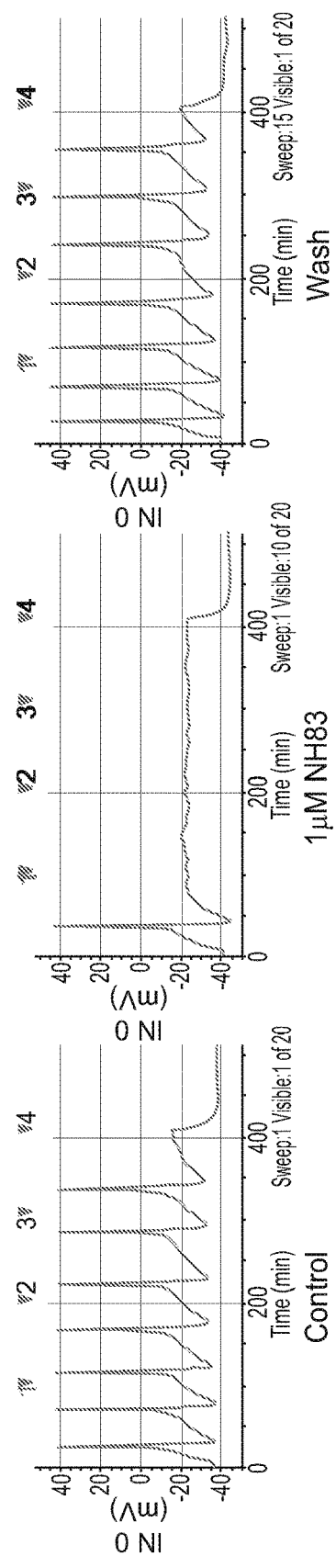

FIGS. 11C-D present the effect of NH82 (FIG. 11C) and NH83 (FIG. 11D) on DRG evoked spike discharge. As shown therein, NH82 affects both recombinant Kv7.2/3 and TRPV1 channels and the DRG evoked spike discharge, and NH83 exhibits a slightly improved activity on the DRG evoked spike discharge. In additional assays, NH91, NH101 and NH110 were identified as the most potent compounds tested both on recombinant channels and on DRG evoked spike discharge.

Figure 12A:
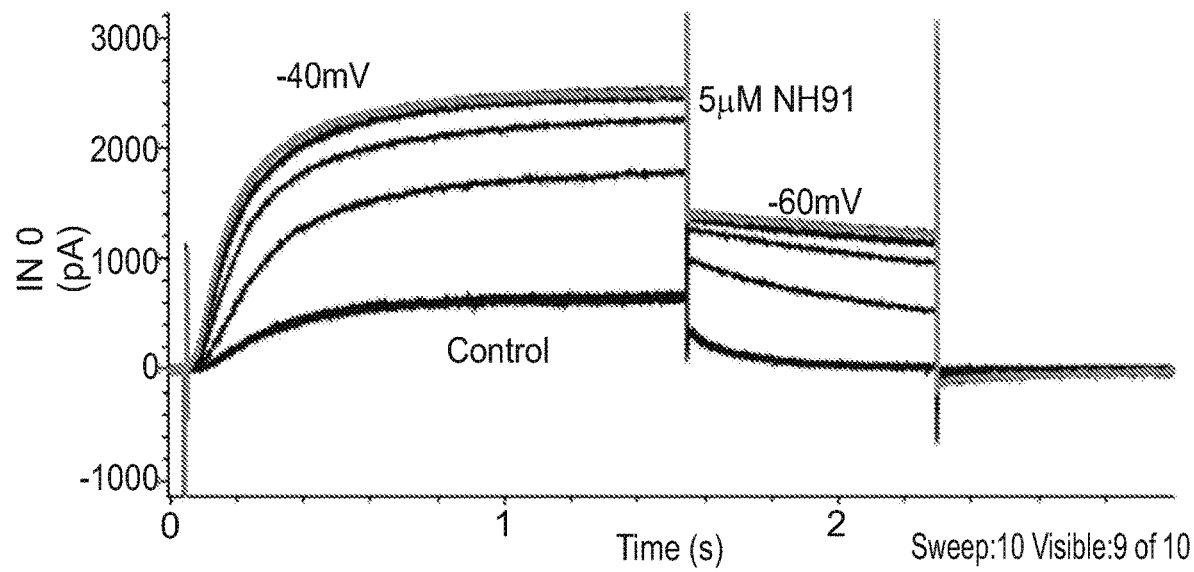
FIGS. 12A-B present comparative plots showing the effect of NH91 on the amplitude at −40 mV (FIG. 12A) and voltage-dependence (FIG. 12B) of recombinant Kv7.2/3 channels.
Figure 12B:
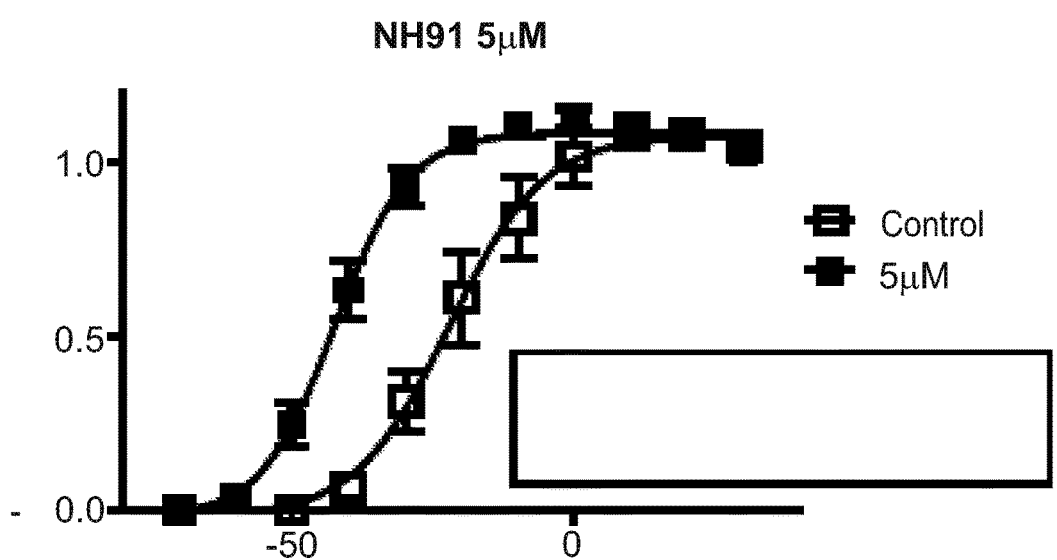
Figure 13A:
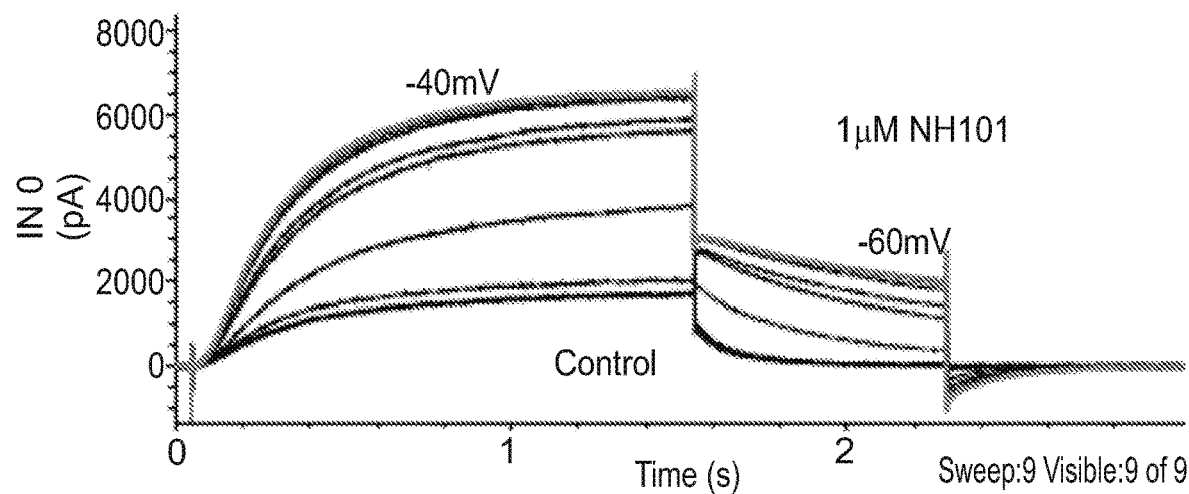
FIGS. 13A-C present comparative plots showing the effect of NH101 on the amplitude at −40 mV (FIG. 13A) and voltage-dependence (FIGS. 13B and 13C) of recombinant Kv7.2/3 channels.
Figure 13B:
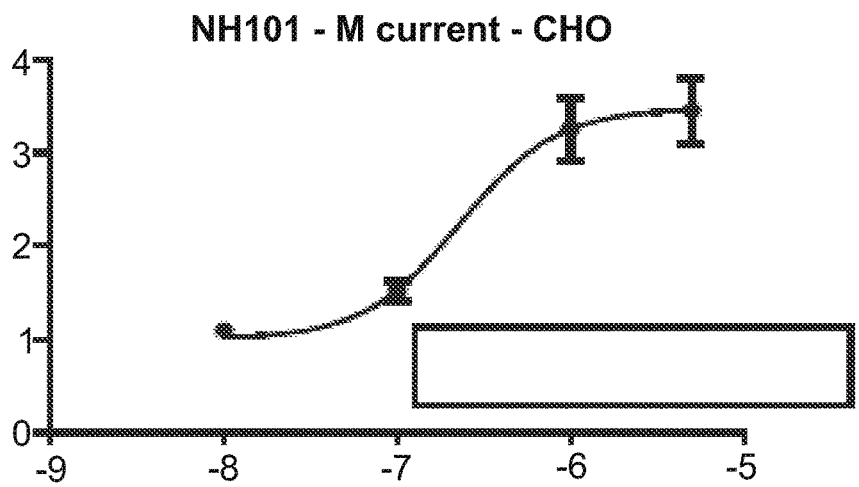
Figure 13C:
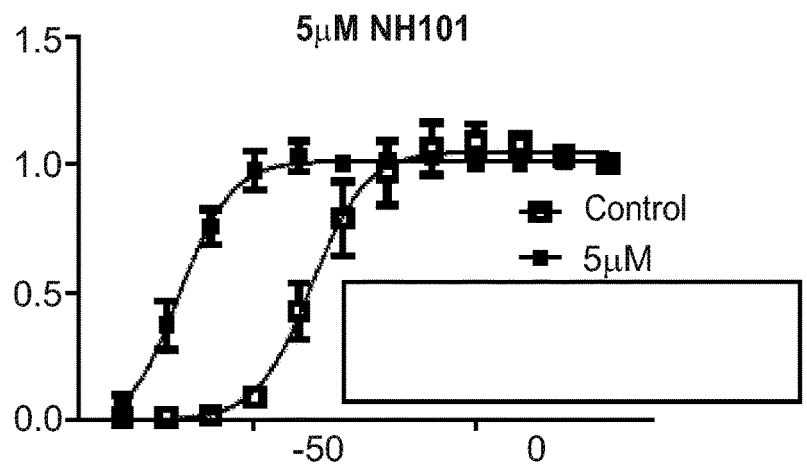
Figure 14A:
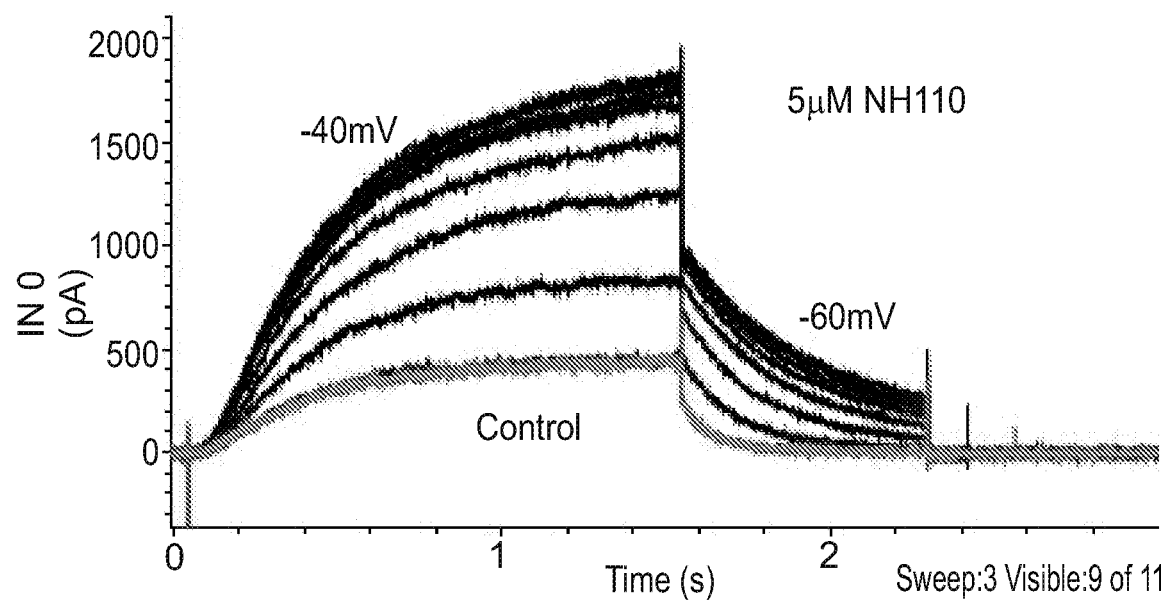
FIGS. 14A-B present comparative plots showing the effect of NH110 on the amplitude at −40 mV (FIG. 14A) and voltage-dependence (FIG. 14B) of recombinant Kv7.2/3 channels.
Figure 14B:
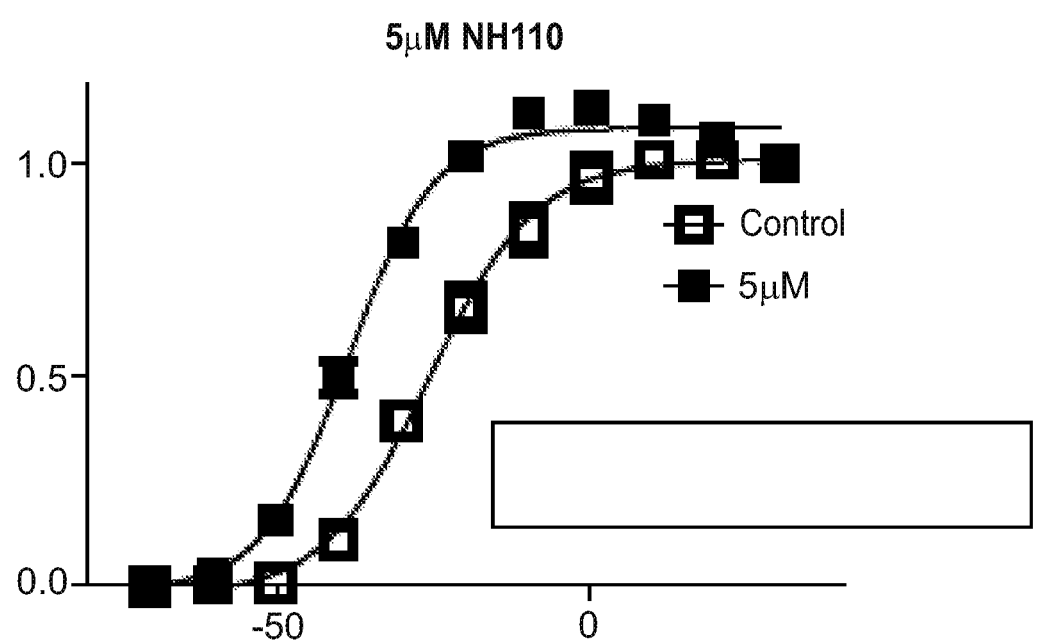

FIGS. 12A-B, 13A-C and 14A-B show the effect of NH91, NH101 and NH110, respectively, on the amplitude at −40 mV (FIGS. 12A, 13A and 14A and voltage-dependence (FIGS. 12B, 13B-C and 14B) of Kv7.2/3 channels, and show that these compounds potently increase the amplitude left-shift the voltage-dependence of activation.

FIG. 15A shows that NH91 prominently inhibits the DRG evoked spike discharge. FIGS. 15B-C show that NH91 (5 μM) did not affect the inward voltage-dependent Ca2+ and Na+ current in DRG neurons, showing its specificity for Kv7.2/3 and TRPV1 currents.

Figure 16:
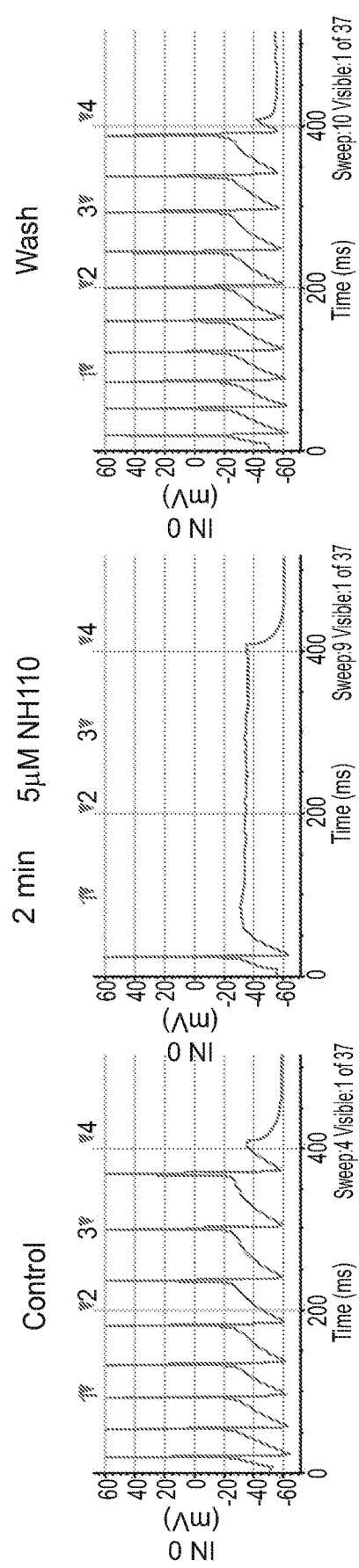
FIG. 16 presents comparative plots showing the inhibition of the DRG evoked spike discharge by NH110.

FIG. 16 show that NH110 also inhibits the DRG evoked spike discharge.

The dual targeting and the synergistic effect of NH91 is further illustrated in FIGS. 17A-B and 18A-B, by its effect on the DRG neuron spike discharge triggered by the activation of TRPV1 channels by 1 μM capsaicin.

Figure 17A:
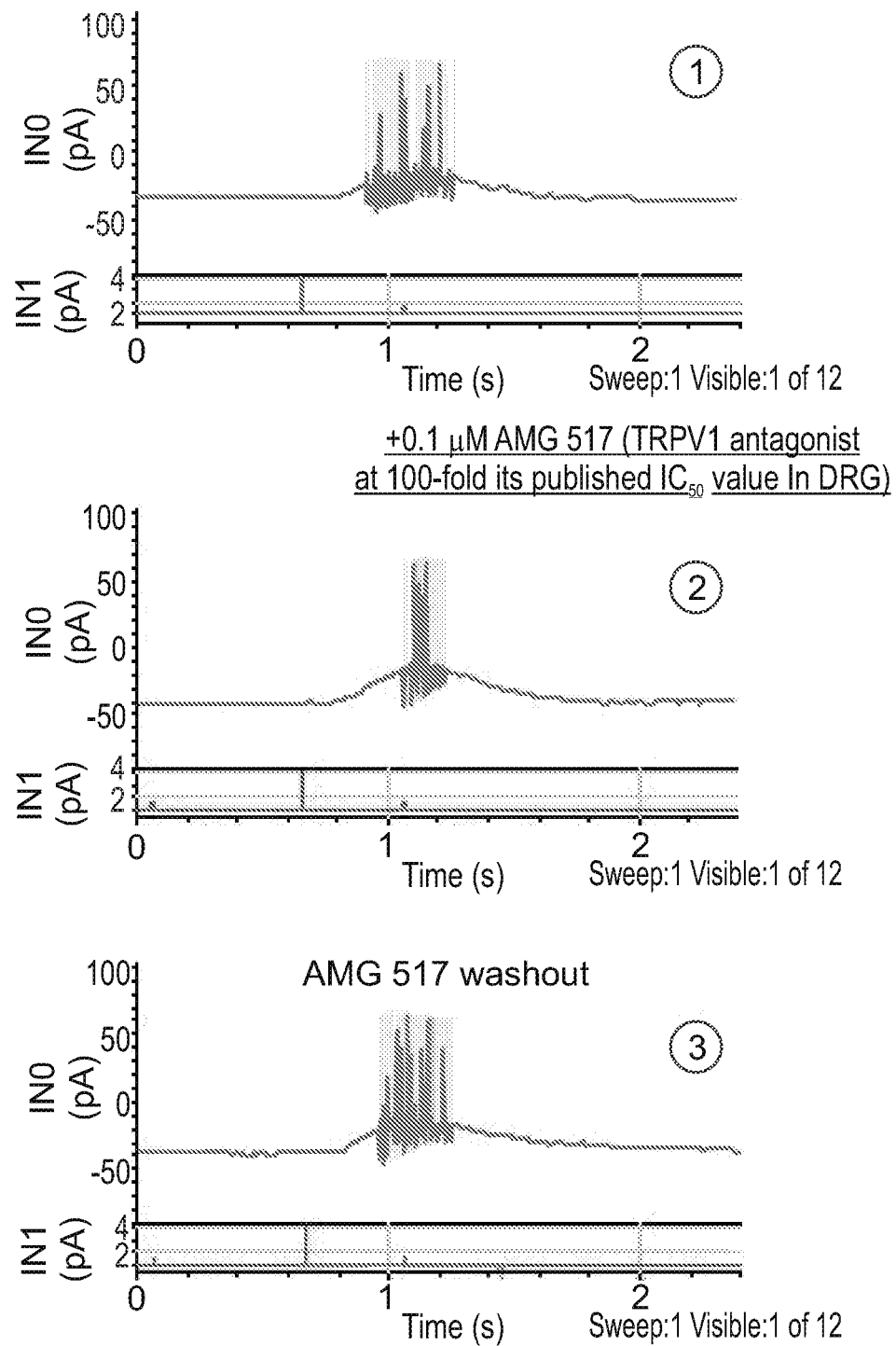
FIGS. 17A-B present comparative plots (FIG. 17A) and a bar graph (FIG. 17B) showing that NH91 produced a significantly more potent inhibition of the capsaicin-evoked DRG spikes, compared to the known TRPV1 antagonist AMG517.
Figure 17A:
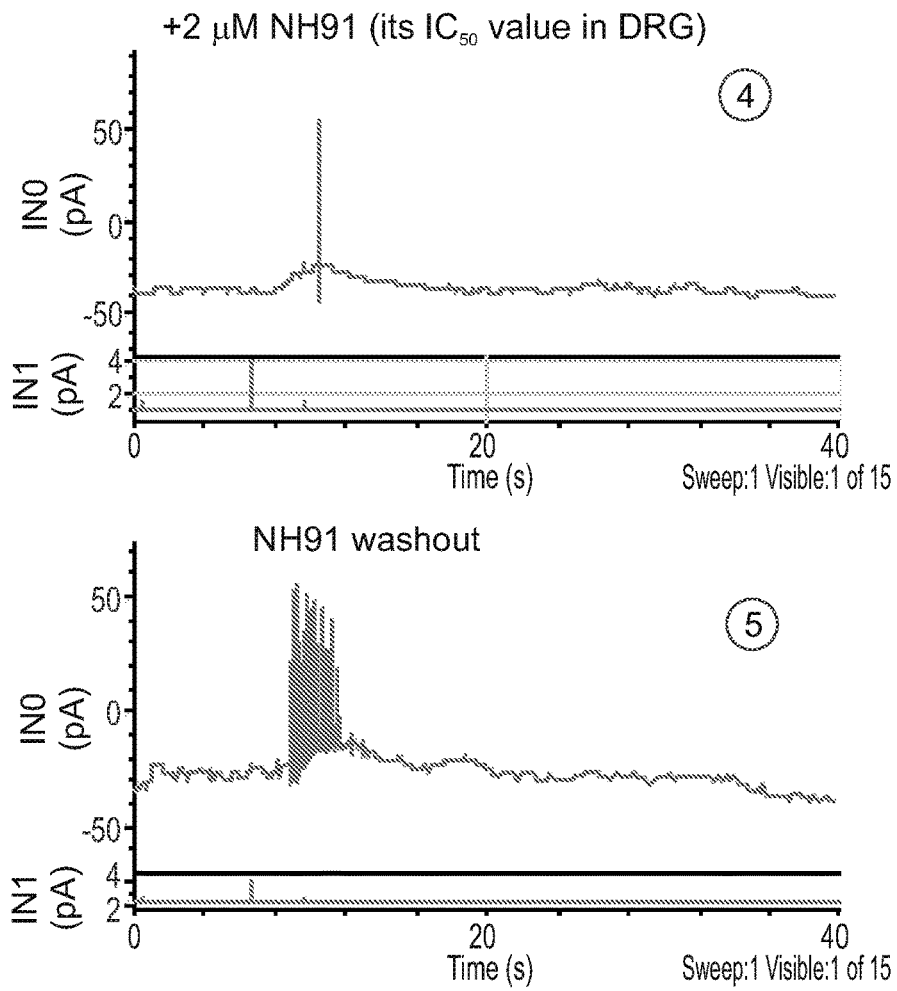
Figure 17B:
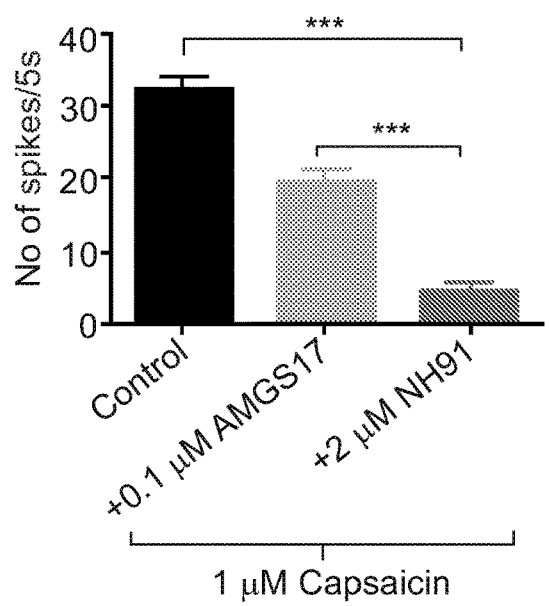

FIGS. 17A and 17B shows that NH91 produced a significantly more potent inhibition of the capsaicin-evoked DRG spikes, compared to the known TRPV1 antagonist AMG517.

While the TRPV1 antagonist AMG 517 (0.1 μM, at 100-fold its IC50) inhibited by 42% the capsaicin-evoked DRG spikes (n=11, one way ANOVA, P<0.0001), NH91 produced a significant more potent inhibition of 88% (n=10, one way ANOVA, P<0.0001). These data show that NH91 exhibits a clear synergistic effect in DRG, compared to a typical high affinity gold standard TRPV1 antagonist like AMG 517. This suggests a synergistic action of NH91 due to its inhibition of TRPV1 channels and to its activation of Kv7.2/3 channels.

Figure 18A:
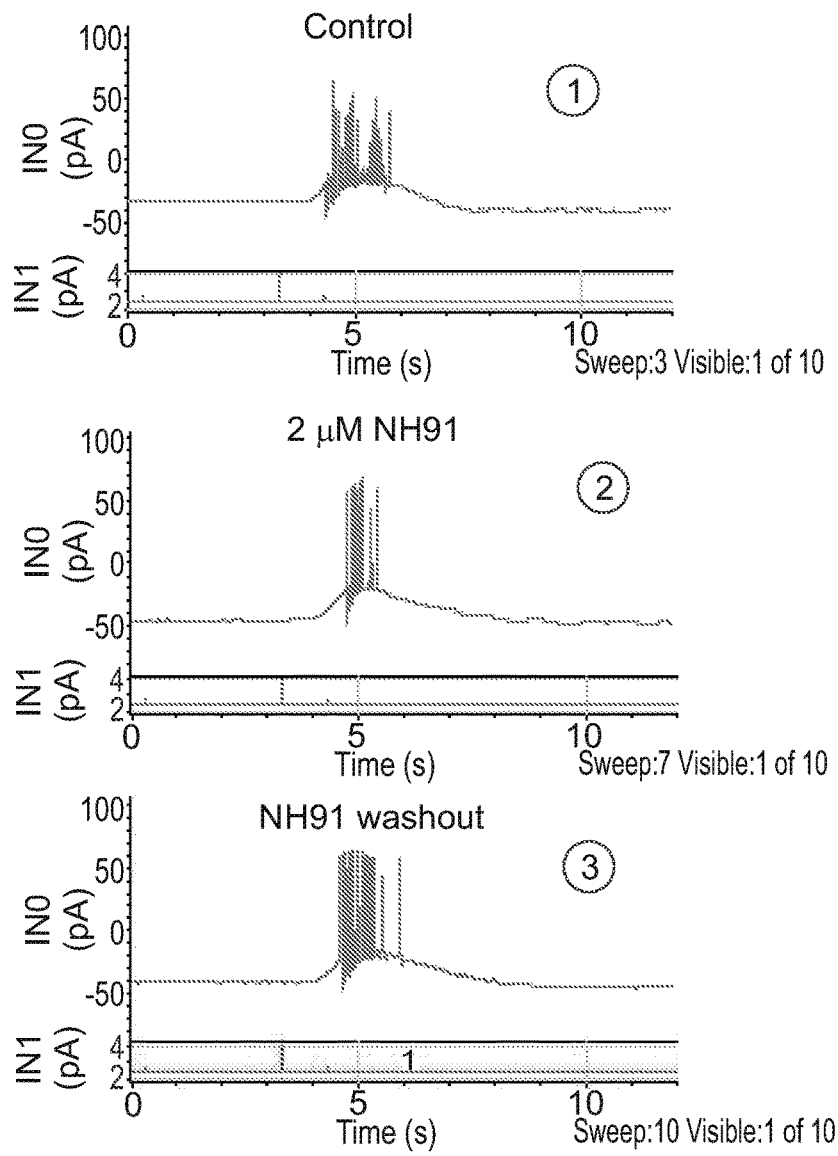
FIGS. 18A-B present comparative plots (FIG. 18A) and a bar graph (FIG. 18B) demonstrating that NH91 inhibits (50%) capsaicin-evoked DRG spike discharge in the presence of the Kv7.2/3 channel blocker XE991 (10 μM).
Figure 18B:
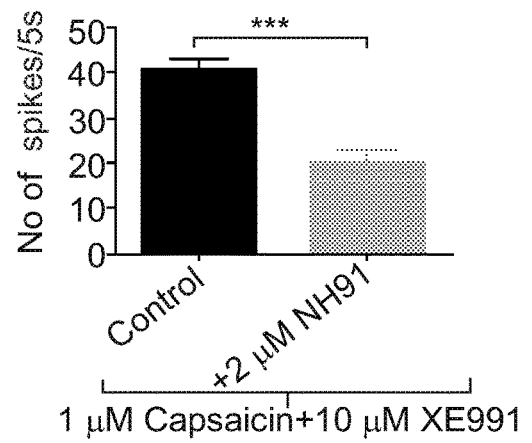

A further support for this contention is shown in FIGS. 18A-B, by the inhibition by NH91 (50%) of capsaicin-evoked DRG spike discharge even in the presence of the Kv7.2/3 channel blocker XE991 (10 μM), revealing its potent inhibition of TRPV1 channels as well (n=11, two-tailed unpaired t-test, P<0.0001).

The lead compounds were further tested for their affinity to the cardiac off target Herg, in order to evaluate a possible adverse effect on this cardiac channel.

Table 1 below summarizes the main parameters demonstrated in the in vitro studies. Starting with two initial hits NH29 and NH34 exhibiting dual channel targeting (openers of Kv7.2/3 and blocker of TRPV1), the SAR studies underlying the present invention have led to the identification of a set of potential leads out of a rational chemistry design of about 50 NCEs.

In contrast to the initial hits, which displayed rather low affinities for the two targets (Kv7.2/3 and TRPV1) and micromolar affinity for the cardiac off target Herg, the potential lead compounds exhibit significantly higher affinity for the targets (0.2-1 μM) and very low affinity (35-135 μM $IC_{50}$s) for the cardiac Herg channels, providing good cardiac safety values, improved efficacy of these compounds, and overall an improved therapeutic index.

The optimized NCEs exhibit a dual channel targeting, activating Kv7.2 and inhibiting TRPV1.

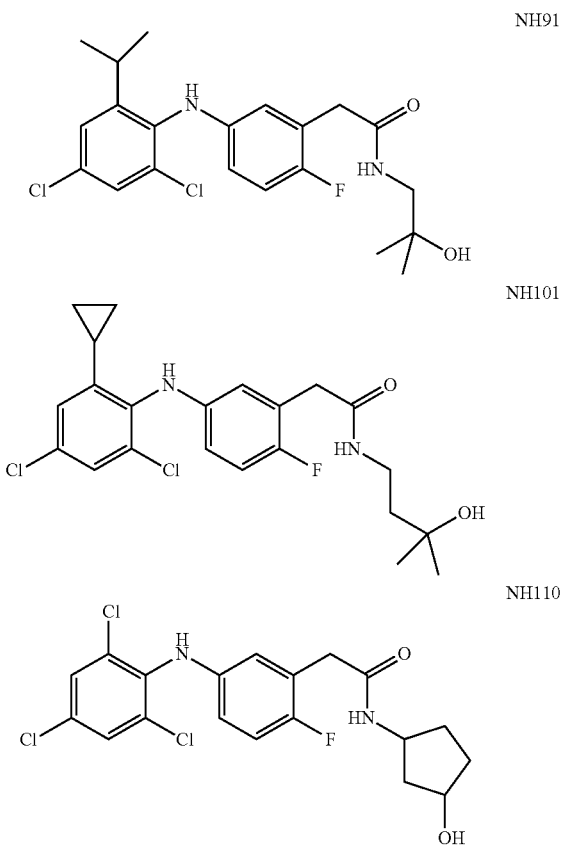

TABLE 1

| Compound | IC$_{50}$ on inhibition of evoked spike discharge in DRG sensory neurons (μM); N = 5-10 | V$_{50}$ (parameter of potency for Kv7.2/3 At 5 μM (mV); N = 5-12 | EC$_{50}$ on Kv7.2/3 (μM) N = 5-10 | IC$_{50}$ on TRPV1 (μM) N = 5-10 | IC$_{50}$ on cardiac Herg channel (μM); N = 5-8 |
|---|---|---|---|---|---|
| NH29 | 18 | −27.4 | 14 | 4.2 | 5 |
| NH34 | 25 | −28.1 | 17.5 | 55 | 35 |
| NH43 | 0.3 | −42.0 | 0.6 | 0.4 | >60 |
| NH66 | 0.5 | −30.3 | 1 | 0.3 | >60 |
| NH82 | 0.5 | −41.1 | 0.5 | 0.4 | >100 |
| NH83 | 0.2 | −37.3 | 0.6 | 0.8 | TBD |
| NH91 | 1 | −42.4 | 2 | 0.1 | >60 |
| NH101 | 0.2 | −67.4 | 0.2 | 0.1 | >50 |
| NH110 | 0.2 | −38.5 | 7.3 | ND* | ND* |
| Retigabine (RTG gold standard) | 5 | −30.4 | 2 | No effect at 30 | >30 |

*ND = not determined

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound represented by Formula Ia:

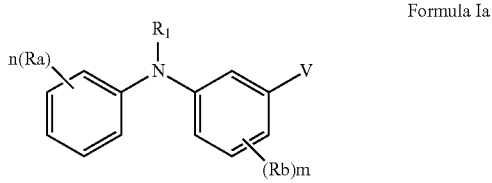

Formula Ia wherein:

n is an integer of from 1 to 5;

m is an integer of from 0 to 5;

Ra and Rb are each independently a substituent selected from alkyl, cycloalkyl, halo, haloalkyl, haloalkoxy, alkoxy, aryl, heteroaryl, heteroalicyclic, aryloxy, hydroxy, amine, alkylamine, thiohydroxy, thioalkoxy, thioaryloxy, cyano, carboxylate, amide, carbamate, sulphonyl, and sulphonamide, or, alternatively, an Ra substituent and R$^1$ form together an alicyclic or heterocyclic ring, wherein when n is greater than 1, each Ra is the same or different substituent, and/or at least two Ra substituents form together an alicyclic or heterocylic ring, and when m is greater than 1, each Rb is the same or different substituent and/or at least two Rb substituents form together an alicyclic or heterocylic ring;

R$_1$ is hydrogen, alkyl, cycloalkyl or aryl; and

V is (CR$_2$R$_3$)k-C(=O)—NR$_4$—Z, and is at the meta position with respect to said N—R$_1$, wherein:

k is an integer of from 0 to 2;

R$_2$ and R$_3$ are each independently selected from hydrogen, halo, alkyl, cycloalkyl, and aryl;

R$_4$ is hydrogen, alkyl, cycloalkyl, or aryl; and

Z is represented by Formula II:

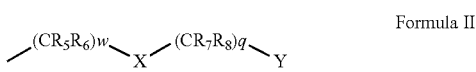

Formula II wherein:

w and q are each independently an integer of from 0 to 4, provided that w+q is at least 2;

X is O or is absent;

Y is selected from OR$_{10}$ and SR$_{10}$;

R$_5$, R$_6$, R$_7$ and R$_8$ are each independently selected from hydrogen, halo, alkyl, haloalkyl, cycloalkyl, heteroalicyclic, aryl, alkylamino, alkoxy, haloalkoxy and aryloxy, or, alternatively, two or R$_5$, R$_6$, R$_7$, and R$_8$ form together an alicyclic or heteroalicyclic ring; and R$_{10}$ is selected from hydrogen, alkyl, cycloalkyl and aryl, or, alternatively, two of R$_5$, R$_6$, R$_7$, R$_8$ and R$_{10}$ form together an alicyclic or heteroalicyclic ring, wherein at least one of the Ra substituents is selected from alkyl, haloalkyl, cycloalkyl and aryl and is at the ortho position with respect to said NR$_1$.

2. The compound of claim 1, wherein:

R$_1$ is hydrogen.

3. The compound of claim 1, wherein m is other than 0 and at least one of said Rb substituent(s) is halo.

4. The compound of claim 3, wherein said halo is at the para position with respect to said NR$_1$.

5. The compound of claim 1, wherein n is 3, 4 or 5.

6. The compound of claim 5, wherein at least two of said Ra substituents other that said Ra at the ortho position with respect to said NR$_1$ are selected from halo and alkoxy.

7. The compound of claim 1, wherein n is 3, one of said Ra substituent(s) is said alkyl, haloalkyl, cycloalkyl or aryl, at the ortho position with respect to said NR$_1$, and the two other Ra substituents are each halo.

8. The compound of claim 1, wherein:
n is 3;
the two other Ra substituents are each halo;
m is 1; and
Rb is halo and is at the para position with respect to said NR₁.

9. The compound of claim 2, wherein:
n is 3;
the two other Ra substituents are each halo;
m is 1; and
Rb is halo and is at the para position with respect to said NR₁.

10. The compound of claim 1, wherein k is 1.

11. The compound of claim 1, wherein at least one of $R_5$, $R_6$, $R_7$ and $R_8$ is independently selected from alkyl, haloalkyl and halo, and/or at least two of $R_5$, $R_6$, $R_7$ and $R_8$ form together an alicyclic ring.

12. The compound of claim 1, wherein q is 1 and at least one or each of $R_7$ and $R_8$ is alkyl.

13. The compound of claim 1, wherein Y is $OR_{10}$, and $R_{10}$ is hydrogen.

14. A compound selected from:

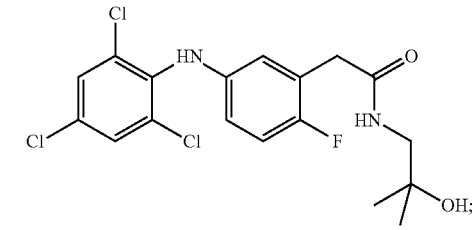
NH66

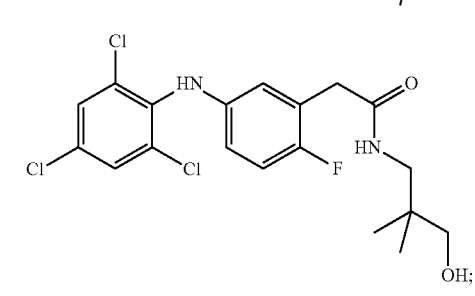
NH82

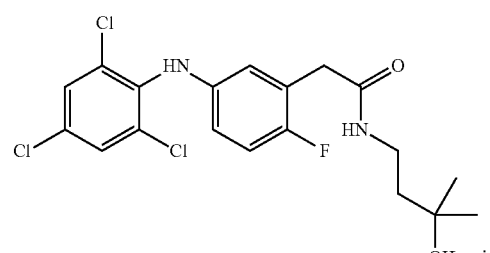
NH83

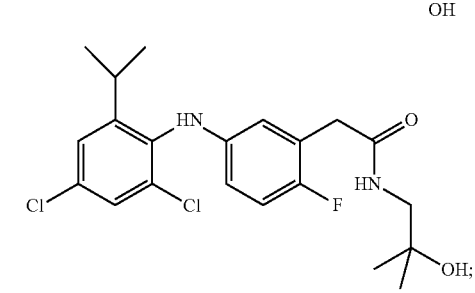
NH91

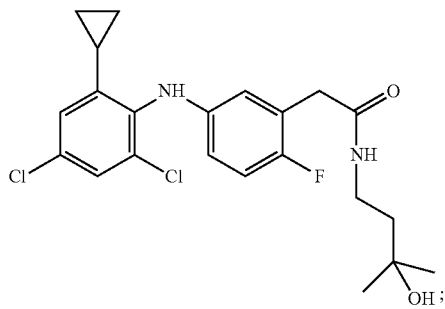
NH101

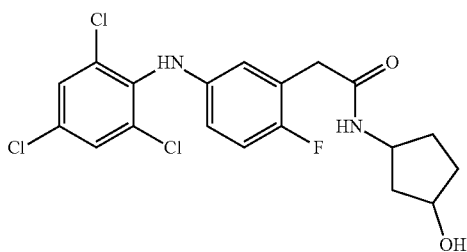
NH110

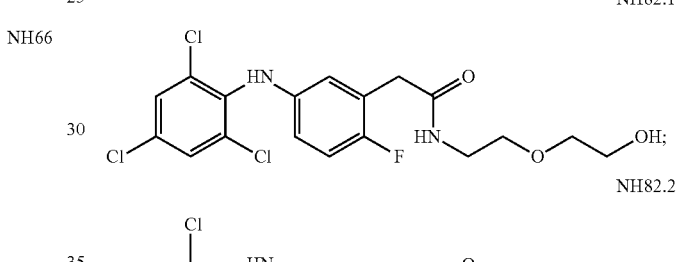
NH82.1

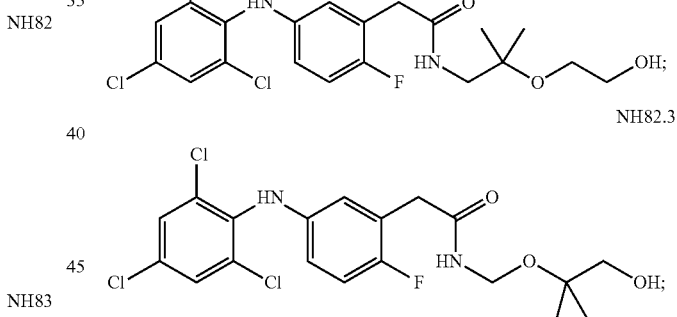
NH82.2

NH82.3

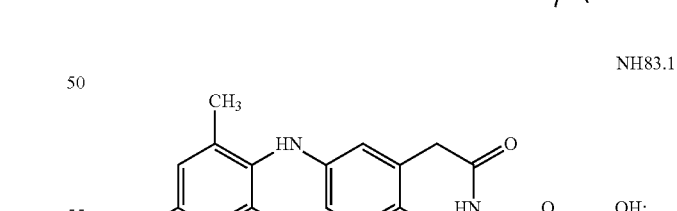

NH83.1

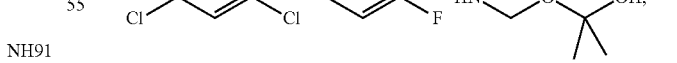

NH83.2

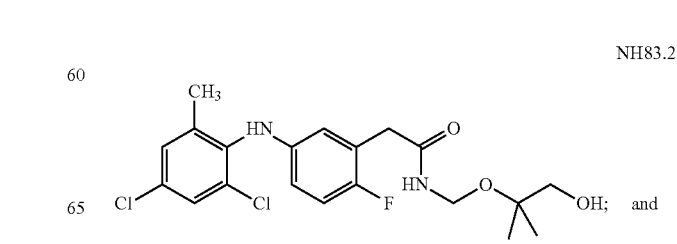
and

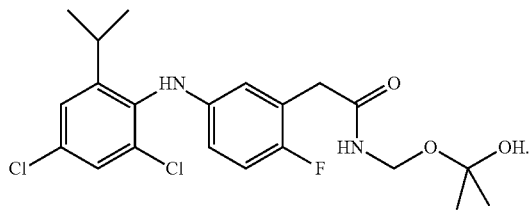

NH83.1

15. A pharmaceutical composition comprising the compound of claim 1 and a pharmaceutically acceptable carrier.

16. The compound of claim 1, capable of opening a voltage-dependent Kv7.2/7.3 potassium channel.

17. The compound of claim 1, capable of modulating inhibiting an activity of TRPV1.

18. The compound of claim 1, capable of of opening a voltage-dependent Kv7.2/7.3 potassium channel and of inhibiting an activity of TRPV1.

19. A method of treating a medical condition which is such that opening a voltage-dependent Kv7.2/7.3 potassium channel and inhibiting an activity of a TRPV1 channel is beneficial to a subject having said medical condition, the method comprising administering to the subject in need thereof a therapeutically effective amount of a compound of claim 1.

20. The method of claim 19, wherein said medical condition is neuropathic pain.

21. A pharmaceutical composition comprising the compound of claim 14 and a pharmaceutically acceptable carrier.

22. A method of treating a medical condition which is such that opening a voltage-dependent Kv7.2/7.3 potassium channel and inhibiting an activity of a TRPV1 channel is beneficial to a subject having said medical condition, the method comprising administering to the subject in need thereof a therapeutically effective amount of a compound of claim 14.

23. The method of claim 22, wherein said medical condition is neuropathic pain.

* * * * *